United States Patent
Uckun et al.

(10) Patent No.: US 6,743,786 B2
(45) Date of Patent: *Jun. 1, 2004

(54) VANADIUM COMPOUNDS FOR TREATING CANCER

(75) Inventors: Fatih M. Uckun, White Bear Lake, MN (US); Yanhong Dong, Moundsview, MN (US); Phalguni Gosh, Shoreview, MN (US)

(73) Assignee: Parker Hughes Institute, St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 10/142,305

(22) Filed: May 8, 2002

(65) Prior Publication Data

US 2003/0073678 A1 Apr. 17, 2003

Related U.S. Application Data

(60) Division of application No. 09/378,531, filed on Aug. 20, 1999, now Pat. No. 6,432,941, and a continuation-in-part of application No. 09/187,115, filed on Nov. 5, 1998, now Pat. No. 6,245,808, and a continuation-in-part of application No. 09/008,898, filed on Jan. 20, 1998, now Pat. No. 6,051,603.

(60) Provisional application No. 60/097,377, filed on Aug. 21, 1998.

(51) Int. Cl.$^7$ ............... A61K 31/444; A61K 31/506; A61K 31/28; A61P 35/00; C07F 9/00

(52) U.S. Cl. .............. 514/184; 514/185; 514/188; 514/186; 514/187; 546/2; 546/6; 546/10; 546/88; 546/255; 549/206; 549/210; 549/212; 544/225

(58) Field of Search .............. 546/2, 6, 10, 255, 546/88; 544/225; 514/185, 184, 188

(56) References Cited

U.S. PATENT DOCUMENTS

| | | |
|---|---|---|
| 4,297,341 A | 10/1981 | Waller et al. |
| 4,322,399 A | 3/1982 | Ahmad et al. |
| 4,368,186 A | 1/1983 | Vickery et al. |
| 4,432,967 A | 2/1984 | Szymanski |
| 4,559,157 A | 12/1985 | Smith et al. |
| 4,588,581 A | 5/1986 | Schmolka |
| 4,608,387 A | 8/1986 | Kopf et al. |
| 4,608,392 A | 8/1986 | Jacquet et al. |
| 4,613,497 A | 9/1986 | Chavkin |
| 4,707,362 A | 11/1987 | Nuwayser |
| 4,795,425 A | 1/1989 | Pugh |
| 4,820,508 A | 4/1989 | Wortzman |
| 4,917,901 A | 4/1990 | Bourbon et al. |
| 4,938,949 A | 7/1990 | Borch et al. |
| 4,992,478 A | 2/1991 | Geria |
| 4,999,342 A | 3/1991 | Ahmad et al. |
| 5,013,544 A | 5/1991 | Chantler et al. |
| 5,021,595 A | 6/1991 | Datta |
| 5,069,906 A | 12/1991 | Cohen et al. |
| 5,300,496 A | 4/1994 | McNeill et al. |
| 5,387,611 A | 2/1995 | Rubinstein |
| 5,407,919 A | 4/1995 | Brode et al. |
| 5,512,289 A | 4/1996 | Tseng et al. |
| 5,595,980 A | 1/1997 | Brode et al. |
| 5,877,210 A | 3/1999 | Schieven |
| 6,245,808 B1 * | 6/2001 | Uckun et al. ............ 514/492 |

FOREIGN PATENT DOCUMENTS

| | | |
|---|---|---|
| DE | 293 495 A5 | 9/1991 |
| EP | 0 407 804 A1 | 6/1990 |
| WO | WO 97/47296 | 12/1997 |

OTHER PUBLICATIONS

Aistars, A. et al., 1997, *Organometallics*, vol. 16, pp. 1994–1996 "Convenient Synthesis of Dichloro(oxo)(pentamethylcyclopentadienyl)vanadium(V), ($\eta$–$C_5Me_5$)V(O)Cl$_2$".

Aitken, et al., 1989, *Biol Reprod*, 40:183–197 "Generation of Reactive Oxygen Species, Lipid Peroxidation and Human Sperm Function".

Aitken, et al., 1993, *J Reprod Fertil*, 97:441–450 "Use of a Xanthine Oxidase Free Radical Generating System to Investigate the Cytotoxic Effects of Reactive Oxygen Species on Human Spermatozoa".

Aitken, et al., 1994, *Bio Essays*, 16:259–267 "Reactive Oxygen Species Generation and Human Spermatozoa: The Balance of Benefit and Risk".

Aitken, et al., 1995, *Reprod. Fertil. Dev.*, 7:659–668 "Free Radicals, Lipid Peroxidation and Sperm Function".

Albini, A. et al., 1987 *Cancer Research*, vol. 47, pp. 3239–3245 (Jun. 15, 1987) "A Rapid In Vitro Assay for Quantitating the invasive Potential of Tumor Cells".

Altamirano–Lozano, et al., 1997, *Med. Sci. Rev.*, 25:147–150 "Effect of some metal compounds on sperm motility in vitro".

Altamirano–Lozano, et al., 1996, *Teratogenesis, Carcinogenesis, and Mutagenesis*, 16:7–17 "Reprotoxic and Genotoxic Studies of Vanadium Pentoxide in Male Mice".

Alvarez, et al., 1987, *J. Androl*, 8:338–348 "Spontaneous Lipid Peroxidation and Production of Hydrogen Peroxide and Superoxide in Human Spermatozoa".

Asami, S. et al., 1996, *Cancer Res.*, 56:2546–2549 "Increase of a type of oxidative DNA damage, 8–hydroxyguanine, and its repair activity in human leukocytes by cigarette smoking".

Aubrecht, J. et al., 1999, *Toxicology and Applied Pharmacology*, vol. 154, No. 3, pp. 228–235 (Feb. 1, 1999) "Molecular and Genotoxicity Profiles of Apoptosis–Inducing Vanadocene Complexes".

(List continued on next page.)

*Primary Examiner*—Evelyn Mei Huang
(74) *Attorney, Agent, or Firm*—Merchant & Gould, P.C.

(57) ABSTRACT

The invention provides methods for treating cancer and compounds that are useful for the treatment of tumors, as well as pharmaceutical compositions comprising the compounds, and synthetic methods and intermediates useful for preparing the compounds.

18 Claims, 9 Drawing Sheets

OTHER PUBLICATIONS

Biggers, et al., 1971, *Methods in Mammalian Embryology,* Daniel, JC Jr. (ed.), San Francisco: Freeman, pp. 86–116 "The Culture of Mouse Embryos in vitro".

Bourinbalar, et al., 1994, *Life Sci,* 54:PL 5–9 "Anti–HIV Effects of Gramicidin in vitro: Potential for Spermicidal Use".

Burkman, L.J., 1991, *Fertil. Steril,* 55:363–371 "Discrimination Between Nonhyperactivated and Classical Hyperactivated Motility Patterns In Human Spermatozoa Using Computerized Analysis".

Butler A., et al., 1989, *Inorganica Chimica Acta,* 163:1–3 "Reactivation of Vanadate–Inhibited Enzymes with Deferoxamine B, a Vanadium (V) Chelator".

Byczkowski, et al., 1988, *Bull Environ Contam Toxicol,* 41:696–703 "Vanadium–Mediated Lipid Peroxidation In Microsomes from Human Term Placenta".

Carmichael A.J., 1990, *FEBS Lett.,* 261:165–170 "Vanadyl–Induced Fenton Like Reaction in RNA: an ESR and a Spin Trapping Study".

Casey, A. T. et al., 1974, *Aust. J. Chem,* vol. 27, pp. 757–768 "Dithiochelates of the Bix($\eta$–cyclopentadienyl)vanadium(IV) Moiety. II N,N–Dialkyldithiocarbamate and O,O'–Dialkyldithiophosphate Complexes".

Chen, D. et al., 1992, *Bopuxue Zazhi,* vol. 9 No. 1, pp. 25–44 "ESR studies on the oxovanadium phenathroline complexes" (Abstract only).

Chen, D. et al., 1993, *Yingyong Huaxue,* vol. 10, No. 3, pp. 68–71 "ESR Spectroscopic Study of Oxovanadium Complexes with His and $\pi$–Acceptor Ligands".

Chen, D. et al., 1993, *Chinese Journal of Magnetic Resonance,* vol. 10, No. 3, pp. 287–294 (Sep. 1993) "Structure and ESR spectra of oxovanadium ternary complexes with aspartic acid and pl.–acceptor ligands".

Chen, D. et al., 1995, *Chines Journal of Applied Chemistry,* vol. 12, No. 2, pp. 59–62 (Apr. 1995) "Study on Structures and Spectra on Oxovanadium Complexes with Glu and Phen Ligands".

Chen, D. et al., 1999, *Journal of Magnetic Resonance,* vol. 16, No. 1, pp. 53–58 (Feb. 1999) "Structures and spectra of VO(II)–Met–Phen complexes".

Chou P., 1999, *Photochemistry and Photobiology,* vol. 70, No. 5, pp. 745–750 "Direct Spectroscopic Evidence for 1$\Delta$gO$_2$ Production from the Photolysis of Vanadium-(V)–Peroxo Complexes in Adqueous Solution".

Choukroun, R. et al., 1995, *Organometallics,* vol. 14, pp. 4471–4473 "Redox Properties of Cationic Vanadium (IV): [Cp$_2$VCH$_3$(CH$_3$CN)][BPh$_4$]".

Cossarizza, A. et al., 1993, *Biochem. Biophys. Res. Commun.,* 197:40–45 A new method for the cytofluorometric analysis of mitochondrial membrane potential using the J–aggregrate forming lipophilic cations 5,5', 6,6'–tetrachloro–1,1', 3,3'–tetraethylbenzimidazolcarbocyanine.

D'Cruz, O.J. et al., 1992, *Fertil. Steril.,* 53:633–636 "Flow cytometric quantitation of the expression of membrane cofactor protein as a marker for the human sperm acrosome reaction".

D'Cruz, et al., 1995, *Biol. Reprod,* 53:1118–1130 "$\delta_2$–Integrin (CD11b/CD18) is the Primary Adhesive Glycoprotein Complex Involved in Neutrophil–Mediated Immune Injury to Human Sperm".

D'Cruz, O.J. et al., 1996, *Biol. Reprod.,* 54:1217–1228 "Recombinant soluble human complement receptor type 1 inhibits antisperm antibody–and neutrophil–mediated injury to human sperm".

D'Cruz, O.J. et al., 1998, *Mol. Hum. Reprod.,* 4:683–693 "Spermicidal activity of chelated complexes of bis(cyclopentadienyl)vanadium(IV)".

D'Cruz, O. et al., 1998, *Biol. Reprod.,* 58:1515–1526 & *Chemical Abstracts,* 129, Abstract No. 76657x:1page "Spermicidal activity of metallocene complexes containing vanadium(IV) in humans".

D'Cruz, O. et al., Copyright 1999, *Chemical Abstracts,* 130, Abstract No. 262258:1page "Spermicidal activity of oxovanadium(IV) complexes of 1, 10–phenanthroline, 2,2'–bipyridyl, 5'–bromo–2'–hydroxyacetophenone and derivatives in humans".

D'Cruz, O.J. et al., 1993, *Fertil. Steril.,* 59:876–884 "The expression of complement regulators CD46, CD55, and CD59 by human sperm does not protect them from antisperm antibody– and complement–mediated injury".

D'Cruz, O.J. et al., 1998, *Book of Abstracts,* See 336, XP002106511 "Vanadium (IV)–Containing Metallocene Induce Cytotoxicity and Apoptosis in Human Testicular Cancer Cell Lines".

D'Cruz, O.J. et al., 1998, *Adv. Reprod.,* ; 1:102–123 "Vandocenes as a new class of effective spermicides".

de Lamirande et al., 1993, *Fertil. Steril.* 59:1291–1295 "Human sperm hyperactivation in whole semen and its association with low superoxide scavenging capacity in seminal plasma".

Demsar, A. et al., 1984, *Journal of Fluorine Chemistry,* vol. 24, No. 3, pp. 369–375 (Mar. 1984) "Synthesis and the molecular and crystal structure of aquadifluorooxo (1, 10–phenanthrolino)vanadium(IV), [VOF$_2$(H$_2$O) (1,10–phenanthroline)]".

Djordjevic, 2995, *Metal Ions In Biological Systems,* Ref. 89, 31:595–615 "Antitumor Activity of Vanadium Compounds".

Dorer, et al., 1997, *Collect Czech Chem Commun,* 62:265–277 "ansa–Vanadocene Complexes—Syntheses, Structures and Ligand Exchange Reactions".

Doyle, et al., 1958, *Inorg. Chem,* 7:2479–2484 "Pseudohalide and Chelate Complexes of Bis(cyclopentadienyl)vanadium(IV)".

Edelman, G., 1994, *Progress in Brain Research,* vol. 101, Chapter 1, pp. 1–14 "Adhesion and counteradhesion: morphogenetic functions of the cell surface".

Eliopoulos,A. et al., 1995, *Biochemical Pharmacology,* vol. 50, No. 1, pp. 33–38 "Induction of the c–myc But Not the cH–ras Promoter by Platinum Compounds".

Erlandsen, et al., 1989, *Scanning,* 11:169–175 "Membrane Fixation for High–Resolution Low–Voltage SEM: Studies on Giardia, Rat Spermatozoa, and Mouse Macrophages".

Filgueiras, C. et al., 1981, *Transition Met. Chem.,* vol. 6, pp. 258–260 "Complexes of Oxovanadium (IV) with Cyclic Nitrogen–Containing Ligands".

Gavrieli, et al., 1992, *J Cell Biol,* 119:493–501 "Identification of Programmed Cell Death in situ via Specific Labelling of Nuclear DNA Fragmentation".

Ghosh, P. et al., 1998, *J. Inorg. Biochem.* (in press) "Structural and biological characterization of a novel spermicidal vandium(IV) complex: Bis($\pi$–cylopentadienyl)–,N,N–diethyl dithiocarbamato vandadium(IV) tetrafluoro borate, [VCp$_2$(DeDtc)(BF$_4$)]".

Gibbons, et al., 1978, *Proc Natl Acad Sci USA*, 75:2220–2224 "Potent Inhibition of Dynein Adenosinetriphosphatase and of the Motility of Cilia and Sperma Flagella by Vanadate".

Heffetz, D. et al., 1990, *J. Biol. Chem.*, vol. 265, vol. 5, pp. 2896–2902 (Feb. 15, 1990) "The insulinomimetic Agents $H_2O_2$ and Vanadate Stimulate Protein Tyrosine Phosphorylation in Intact Cells".

Hiort, C. et al., 1996, *Biochemistry*, 35:12354–12362 "Cleavage of DNA by the insulin–mimetic compound, $NH_4$ [$VO(O_2)_2$(phen)]".

Hirao, T., 1997, *Chemical Rev.* 97:2707–2724 "Vanadium in modern organic synthesis".

Holmes, L., Jr. 1961, Ph.D. Thesis, LSU "Physical Chemical Studies on Inorganic Coordination Compounds. I. Metallic Complexes of Dimethylsulfoxide. II. Preparation and Spectral Studies of Vanadyl Complexes".

Hyslop, P.A. et al., 1988, *The Journal of Biological Chemistry*, 263(4):1665–1675 "Mechanisms of Oxidant–mediated Cell Injury".

Islam, M. et al., 1992, *Journal of the Bangladesh Chemical Society*, vol. 5, No. 2, pp. 115–120 "Mixed Ligand Complexes of Phthalic Acid and Amine Bases".

Jones, et al., 1979, *Fertil Steril*, 31:531–537 "Peroxidative Breakdown of Phospholipids in Human Spermatozoa: Spermicidal Effects of Fatty Acid Peroxides and Protective Action of Seminal Plasma".

Keller, R.J. et al., 1988, *Archiv. Biochem. Biophys.*, 265:524–533 Vanadium and lipid peroxidation: evidence for involvement of vanadyl and hydroxyl.

Kessopoulou, E. et al., 1992, *J. Reprod. Fert.*, 94:463–470 "Origin of reactive oxygen species in human semen: spermatozoa or leucocytes?".

Klebanoff, S.J. et al., 1992, *Infect. Dis.*, 165:19–25 "Effects of the spermicidal agent nonoxynol–9 on vaginal microbial flora".

King, B., 1965, *Academic Press, Inc.*, vol. 1, pp. 75–76 "Organometallic Syntheses".

Kopf–Maier, et al., 1981, *Eur J Cancer*, 17:665–669 "Tumor Inhibition by Metallocenes: Activity Against Leukemias and Detection of the Systematic Effect".

Kofp–Maier, et al., 1981, *Cancer Chemother Pharmacol*, 5:237–241 "In vitro Cell Growth Inhibition by Metallocene Dichlorides".

Kofp–Maier, et al., 1983, *Chem Biol Interactions*, 44:317–328 "Tumor Inhibition by Metallocenes: Ultrastructural Localization of Titanium and Vanadium in Treated Tumor Cells by Electron Energy Loss Spectroscopy".

Kofp–Maier, et al., 1983, *J Cancer Res Clin Oncol*, 106:44–52 "Induction of Cell Arrest at $G_1$/S and in $G_2$ After Treatment of Ehrlich Ascites Tumor Cells with Metallocene Dichlorides and cis–Platinum in vitro".

Kofp–Maier, et al., 1984, *Virchows Arch [Cell Pathol]*, 47:107–122 "Cytologic Observations on the Effects of Metallocene Dichlorides on Human Fibroblasts Cultivated in vitro".

Kopf–Maier, et al., 1984, *Eur. J. Med. Chem.—Chim. Ther.*, vol. 19, No. 4, pp. 347–352 "Tumorhemmung durch Metallocene: Titan–Komplexe des Typs [$TiCp_2XY$] und [$TiCp_2XY$]".

Kopf–Maier, P., 1987, *J. Cancer Res Clin Oncol*, vol. 113, pp. 342–348 "Tumor Inhibition by titanocene complexes: Influence upon two xenografted human lung carcinomas".

Kofp–Maier, P. et al., 1987, *Chem. Rev.*, 87:1137–1152 Non–platinum–group metal antitumor agents: history, current status, and perspectives.

Kopf–Maier, P. et al., 1987, *Arzneim.–Forsch./Drug Res.* vol. 37, pp. 532–534 "Tumor Inhibition by Titanocene Complexes".

Kopf–Maier, et al., 1988, *Structure and Bonding*, 70:103–185 "Transition and Main–Group Metal Cyclopentadienyl Complexes: Preclinical Studies on a Series of Antitumor Agents of Different Structural Type".

Kopf–Maier, et al., 1993, In: Kepper BK (ed.), *Metal Complexes in Cancer Chemotherapy*, New York: VCH Publishers, pp. 259–296 "Antitumor bis(cyclopentadienyl) Metal Complexes".

Kuo et al., 1996, In: Sigel H. (ed.), *Metal Ions in Biological Systems*, pp. 53–85 "Metallocene Interactions with DNA and DNA–Processing Enzymes".

Macara I.G., 1980, Trends Biochem Sci, 5:92–94 "Vanadium—An Element in Search of a Role".

Martin, et al., 1995, *J Exp Med*, 182:1545–1556 "Early Redistribution of Plasma Membrane Phosphotidylserine is a General Feature of Apoptosis Regardless of the Initialing Stimulus: Inhibition by Overexpression of Bcl–2 and Abl".

McLaughlin, et al., 1990, *J Am Chem Soc*, 112:8949–8952 "DNA–Metal Binding by Antitumor–Active Metallocene Dichlorides from Inductively Coupled Plasma Spectroscopy Analysis: Titanocene Dichloride Forms DNA–$Cp_2$ Ti or DNA–CpTi Adducts Depending on pH".

Meirim, M. et al., 1984, *Transition Met. Chem.*, vol. 9, No. 9, pp. 337–338 (Sep. 1984) "A Chlorotltanocene Tetrachloroferrate Complex Stabilized by Acetonitrile Coordination".

Moebus, et al., 1997, *Anticancer Res.*, 17:615–822 "Antitumor Activity of New Organometallic Compounds in Human Ovarian Cancer Cell Lines and Comparison to Platin Derivatives".

Moran, et al., 1985, *J. Organometallic Chemistry*, 291:311–319 "Synthesis and Characterization of Halogen and Pseudohalogen Derivatives of Substituted Vanadocenes".

Mosmann, T., 1983, *Journal of Immunological Methods*, vol. 65, pp. 55–63 "Rapid Colorimetric Assay for Cellular Growth and Survival: Application to Proliferation and Cytotoxicity Assays".

Murthy, et al., 1988, *Inorg. Chemica Acta*, 152:117–124 "Antitumor and Toxicologic Properties of the Organometallic Anticancer Agent Vanadocene Dichloride".

Narla, R. et al., 1988, *Clinical Cancer Research*, vol. 4, pp. 1405–1414 (Jun. 1998) 4–(3'Bromo–4'hydroxylphenyl)–amino–6,7–dimethoxyquinazoline: A Novel Quinazoline Derivative with potent Cytotoxic Activity against Human Glioblastoma Cells.

Narla, R. et al., 1988, *Clinical Cancer Research*, vol. 4, pp. 2463–2471 (Oct. 1998) "Inhibition of Human Glioblastoma and Cell Adhesion and Invasion by 4–(4'–Hydroxylphenyl)–amino–6,7–dimethoxyquinazoline (WHI–P131) and 4–(3'–Bromo–4"–hydroxylphenyl)–amino–6,7–dimethoxyquinazoline (WHI–P154)".

Nechay, B.R., 1984, *Annu. Rev. Pharmacol Toxicol.* 24:501–524 "Mechanisms of action of vanadium".

Niruthisard, et al., 1991, *Sex Transm Dis*, 18:176–179 "The Effects of Frequent Nonoxynol–9 Use on the Vaginal and Cervical Mucosa".

Orvig, C. et al., 1995, *metel ions in biological systems*, vol. 31, Ch. 17, pp. 595–616 "Vanadium Compounds as Insulin Mimics".

Ozawa, et al., 1989, *Chem. Pharma Bull*, 37:1407–1409 "ESR Evidence for the Formation of Hydroxyl Radicals During the Reaction of Vanadyl Ions with Hydrogen Peroxide".

Petersen, et al., 1975, *J Am Chem Soc*, 97:6422–6433 "Synthesis and Structural Characterization by X–ray Diffraction and Electron Paramagnetic Resonance Single–Crystal Techniques of $V(O^5-C_5H_4CH_3)_2Cl_2$. A Study of the Spatial Distribution of the Unpaired Electron in a $V(O_5-C_5H_5)_2L_2$–type Complex".

Perentesis, J. 1997, *Clinical Cancer Research*, vol. 3, pp. 347–355 (Mar. 1997) "Induction of Apoptosis in Multidrug–resistant and Radiation–resistant Acute Myeloid Leukemia Cells by a Recombinant Fusion Toxin Directed against the Human Granulocyte Macrophage Colony–stimulating Factor Receptor".

Quilitzsch, U. et al., 1979, *Inorganic Chemistry*, vol. 18, No. 3, pp. 869–871 "Kinetics of the Diperoxovanadate(V)–Monoperoxovanadate(V) Conversion in Percholoric Acid Media".

Rao, B. et al., 1989, *Gamete Res.*, 24:127–134 "Lipid peroxidation in human spermatozoa as related to midpiece abnormalities and motility".

Rehder, D., 1991, *Angew Chem Int Ed Engl*, 39:148–167 "The Bioinorganic Chemistry of Vanadium".

Roddy, et al., 1993, *Int. J Std AIDS*, 4:165–170.

"A Dosing of Nonoxynol–9 and Genital Irritation" Roshchin, et al. 1980, *Gig. Tr. Prof. Zabol.*, 5:49–51 (Abstract only) "Effect of *vanadium* on the generative function of laboratory animals".

Sakurai, et al., 1992, *Biochemical and Biophysical Research Communications*, 189:1090–1095 "DNA Cleavage by Hydroxyl Radicals Generated in a Vanadyl Ion–Hydrogen Peroxide System".

Sakurai, et al., 1995, *Biochem Biophys Res Commun*, 206:133–137 "Mechanism for a New Antitumor Vanadium Complex: Hydroxyl Radical–Dependent DNA–Cleavage by 1, 10–Phenanthroline–Vanadyl Complex in the Presence of Hydrogen Peroxide".

Savostina, V. M. et al., 1979, *Zh. Neorg. Khim.*, vol. 24, No. 1, pp. 41–45 "Study of the reaction on vanadium(III), vanadium(IV), and vanadium(V) with 1, 10–phenanthroline".

Selbin, J., 1985, *Chemical Reviews*, vol. 65, No. 2, pp. 153–175 (Mar. 25, 1965) The Chemistry of Oxovanadium(IV).

Sharma C.L. et al., 1986, *Synth. React. Inorg. Met.–Org. Chem.*, vol. 16, No. 9, pp. 1261–1271 Preparation and Characterisation of Mixed Ligand Complexes of Titanium (III) and Vanadium (IV) with Imides and Heterocyclic Amines.

Shi, et al., 1996, *Annals of Clinical and Laboratory Science*, 26:39–49 "Vanadium(IV) Causes 2'–Deoxyguanosine Hydroxylation and Deoxyribonucleic Acid and Damage Via Free Radical Reaction".

Smiley, S.T. et al., 1991, *Proc. Natl. Acad. Sci. USA*, 88:3671–3675 "Intracellular heterogeneity in mitochondrial membrane potentials revealed by J–aggregate–forming lipophilic cation JC–1".

Sofina, Goldin and Belousova, Dec. 1980, *National Cancer Institute Monograph*, No. 50 Experimental Evaluation of Antitumor Drugs in the USA and USSR and Clinical Correlations.

Stern, A. et al., 1993, *Biochem. Cell Biol.*, vol. 71, Nos. 3 & 4, pp. 103–112 (Mar.–Apr. 1993) "Vanadium as a modulator of cellular regulatory cascades and oncogene expression".

Stoffel, et al., *Molecular Reprod Develop* 1993; 34:175–182 "Improved Preservation of Rat Epididymal Sperm for High–Resolution Low–Voltage Scanning Electron Microscopy (HR–LVSEM)".

Teebor, G.W. et al., 1988, *Int. J. Radiat. Biol.*, 54:131–150 "The repairability of oxidative free radical mediated damage to DNA: a review".

Thewalt, U. et al., 1986, *Journal of Organometallic Chemistry*, vol. 302, pp. 193–200 "Kationische Komplexe Mit Der $(\eta^5-C_5H_5)_2Ti^{IV}$–Baugruppe: Darstellung Und Strukter von $[\eta^5-C_5H_5)_2$ Ti(bipy)]$^{2+}$(CF$_3$SO$_3$–)$_2$ Und $[(\eta^5C_5H_5)_2Ti(phen)]^{2+}(CF_3SO_3-)_2$".

Thewalt, et al., 1995, *Transition Metal Chem*, 10:393–395 "The Crystal and Molecular Structure of Acetonitrilechlorodicyclopentadienyltitanium Tetrachloroferrate (III). Some Mössbauer and X–Ray Photoelectron Spectroscopic Data".

Toney, et al., 1985, *J Am Chem Soc*, 107:947–953 "Hydrolysis Chemistry of the Metallocene Dichlorides $(M(O^5-C_5H_5)_2Cl_2$, M=Ti, V, Zr. Aqueous Kinetics, Equilibria, and Mechanistic Implications for a new Class of Antitumor Agents".

Toney, J. et al., 1986, *J. Am. Chem. Soc.* 108:7263–7274 "Aqueous Coordination Chemistry of Vanadocene Dichloride, (V( $\eta^5-C^5H^5$)xCl$_2$, with Nucleotides and Phosphoesters. Mechanistic Implications for a new Class of Antitumor Agents".

Tryphonas, et al., 1984, *Toxicol* Lett, 20:289–295 "Morphologic Evidence for Vaginal Toxicity of Delfen Contraceptive Cream in the Rat".

Tryphonas, et al., 1986, *Toxicol*, 39:177–186 "Effects of the Spermicide Nonoxynol–9 on the Pregnant Uterus and the Conceptus of Rat".

Tsiani, E. et al., 1997, *Trends in Endocrinol Metab.*, vol. 8, No. 2 (Mar. 1997) "Vanadium Componds, Biological Actions and Potential as Pharmacological Agents".

Uckun, F.M. et al., 1995 *Science*, vol. 267, No. 5199, pp. 856–891 (Feb. 10, 1995) "Biotherapy of B–Cell Precursor Leukemia by Targeting Genistein to CD 19–Associated Tyrosine Kinases".

Uckun, F. et al., 1998, *Clinical Cancer Research*, vol. 4, pp. 901–912 (Apr. 1998) "Cytotoxic Activity of Epidermal Growth Factor–Genistein against Breast Cancer Cells".

van Engeland, M. et al., 1998, *Cytometry*, 31:1–9 "Annexin V–affinity assay: A review on an apoptosis detection system based on phosphatidylserine exposure".

Vassilev, A., 1999, *Journal of Biological Chemistry*, vol. 274, No. 3, pp. 1646–1656 (Jan. 15, 1999) "Bruton's Tyrosine Kinase as an Inhibitor of the Fas/CD95 Death–inducing Signaling Complex".

Vermes, et al ., 1995, *J. Immunol Meth*, 184:39–51.

"A Novel Assay for Apoptosis. Flow Cytometric Detection of Phosphatidylserine Expression on Early Apoptotic Cells Using Fluorescein Labelled Annexin V".

Vinklárek, J. et al., *Metal–Based Drugs*, vol. 4, No. 4, pp. 207–219 (1997) "Behaviour of the Antitumor Agent Vanadocene Dichloride in Physiological and Therapeutic Media, Blood Plasma and Human Blood—An EPR Study".

Waurzyniak, B. et al., 1997, *Clinical Cancer Research,* vol. 3, pp. 881–890 (Jun. 1997) "In Vivo Toxicity, Pharmacokinetics, and Antileukemic Activity of tXU (Anti–CD7)–Pokeweed Antiviral Protein Immunotoxin".

Wilborn, et al. ,1983, *Fertil. Steril,* 39:717–719 "Scanning Electron Microscopy of Human spermatozoa After Incubation with the Spermicide Nonoxynol–9".

Wilkinson, et al., 1954, *J Am Chem Soc,* 76:4281–4284 "Bis–cyclopentadienyl Compounds of Ti, Zr, V, Nb, and Ta".

Wilkinson, G. 1982, *Comprehensive Organometallic Chemistry,* New York, Pergamon, 3:554–646 "Zirconium and Hafnium: Introduction".

Wu, C., 1998, *Science News,* 6:359 "New spermicides stop cell gently".

Younes, et al., 1991, *Toxicology,* 66:63–74 "Vanadate–Induced Toxicity Towards Isolated Perfused Rat Livers: The Role of Lipid Peroxidation".

Zamzani, N. et al., 1995, *J. Exp. Med.,* 181:1661–1672 "Reduction in mitochondrial potential constitutes an early irreversible step of programmed lymphocyte death in vivo".

U.S. patent application Ser. No. 09/008/898, filed Jan. 29, 1998.

\* cited by examiner

VANADIUM COMPOUNDS FOR TREATING CANCER

PRIORITY OF INVENTION

This application is a divisional of U.S. patent application Ser. No. 09/378,531 filed on Aug. 20, 1999, now U.S. Pat. No. 6,432,941 which claims priority to U.S. Provisional Application Serial No. 60/097,377 filed Aug. 21, 1998 and is a continuation-in-part of U.S. application Ser. No. 09/187,115 filed Nov. 5, 1998 now U.S. Pat. No. 6,245,808 and a continuation-in-part of U.S. application Ser. No. 09/008,898 filed on Jan. 20, 1998 now U.S. Pat. No. 6,051,603.

FIELD OF THE INVENTION

The present invention relates to Vanadium (IV) compounds effective for treating tumor cells and particularly effective to induce apoptosis in leukemia cells, breast cancer cells, prostate cancer cells, and brain cancer cells.

BACKGROUND OF THE INVENTION

Cancer is a major disease that continues as one of the leading causes of death at any age. In the United States alone, it is anticipated that more than half a million Americans will die of cancer in 1999. Currently, radiotherapy and chemotherapy are two important methods used in the treatment of cancer.

Considerable efforts are underway to develop new chemotherapeutic agents for more potent and specific anti-cancer therapy, presenting effective and efficient cytotoxicity against tumor cells, with minimal interference with normal cell function. Accordingly, there is an urgent need for the development and analysis of novel, effective anti-cancer agents.

A single vanadocene (IV) compound (e.g., $VCp_2Cl_2$) is reported as having biological activity.

Sakurai, et. al, BBRC, Vol. 206, p. 133 (1995) discloses an oxovanadium compound (e.g., $[VO(Phen)(H_2O)_2](SO_4)$) that is active against pharyngonasal cancer as determined by a single assay.

Holmes, Ph.D. Thesis, LSU (1961) discloses oxovanadium compounds (e.g., $[VO(SO_4)(Phen)_2]$ and $[VO(ClO_4)(Bpy)_2]$) but does not disclose biological data for the compounds.

Selbin, Chem. Rev., Vol. 65, p. 155 (1965) discloses oxovanadium compounds (e.g., $[VO(SO_4)(Phen)_2]$ and $[VO(ClO_4)(Bpy)_2]$) but does not disclose biological data for the compounds.

SUMMARY OF THE INVENTION

The invention provides a method for treating cancer in a mammal comprising administering to the mammal in need of such treatment an effective amount of a vanadium (IV) compound; or a parmaceutically acceptable salt thereof; with the proviso that the vanadium (IV) compound is not $VCp_2Cl_2$ or $[VO(Phen)(H_2O)_2](SO_4)$.

The invention also provides a method for treating a mammal inflicted with cancer comprising administering to the mammal in need of such treatment an effective amount of an oxovanadium compound; or a pharmaceutically acceptable salt thereof; with the proviso that the cancer is not pharyngonasal cancer.

The invention also provides a method for treating a mammal inflicted with cancer comprising administering to the mammal in need of such treatment an effective amount of a vanadocene compound; or a pharmaceutically acceptable salt thereof; with the proviso that the vanadocene compound is not $VCp_2Cl_2$.

The invention also provides a compound of formula II:

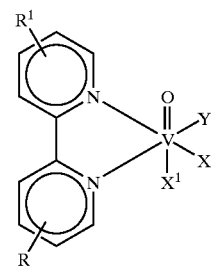

(II)

wherein R and $R^1$ are each independently H, (C1–C3)alkyl, halogen, (C1–C3)alkoxy, halo(C1–C3)alkyl, cyano, $(C_2-C_6)$alkanoyloxy or nitro; X and $X^1$ are each independently a monodentate or bidentate ligand, or no ligand is present on $X^1$; and Y is a monodentate ligand; or a pharmaceutically acceptable salt thereof.

The invention also provides a compound of formula III:

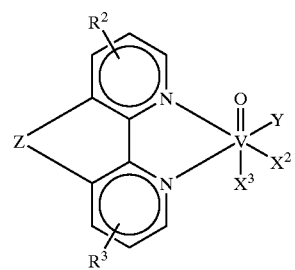

(III)

wherein $R^2$ and $R^3$ are each independently H, (C1–C3)alkyl, halogen, (C1–C3)alkoxy, halo(C1–C3)alkyl, cyano, $(C_2-C_6)$alkanoyloxy or nitro; $X^2$ and $X^3$ are each independently a monodentate or bidentate ligand, or no ligand is present on $X^3$; and Z is O, $CH_2$, $CH_2$—$CH_2$ or CH=CH; or a pharmaceutically acceptable salt thereof; with the proviso that the compound is not $[VO(Phen)(H_2O)_2](SO_4)$ or $[VO(SO_4)(Phen)_2]$.

The invention also provides a compound of formula IV:

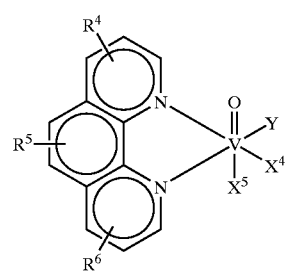

(IV)

wherein $R^4$, $R^5$ and $R^6$ are each independently H, (C1–C3)alkyl, halogen, (C1–C3)alkoxy, halo(C1–C3)alkyl, cyano, $(C_2-C_6)$alkanoyloxy or nitro; $X^4$ and $X^5$ are each independently a monodentate or bidentate ligand, or no ligand is present on $X^5$; Y is a monodentate ligand, or no ligand is present on $X^5$; and Y is a monodentate ligand; or a pharmaceutically acceptable salt thereof; with the proviso that the compound is not $[VO(Phen)(H_2O)_2](SO_4)$ or $[VO(SO_4)(Phen)_2]$.

The invention also provides a compound of formula V:

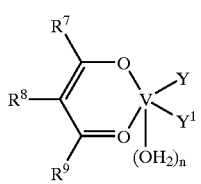
(V)

wherein $R^7$ and $R^9$ are each independently H, (C1–C3)alkyl, (C1–C3)alkoxy, or halo(C1–C3)alkyl; $R^8$ is H, (C1–C3) alkyl, halo, (C1–C3)alkoxy, or halo(C1–C3)alkyl; Y and $Y^1$ are each independently a monodentate or bidentate ligand; and n is 0 or 1; or a pharmaceutically acceptable salt thereof.

The invention also provides a compound of formula VII:

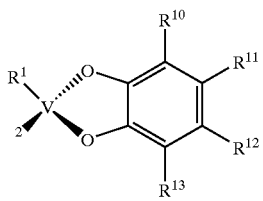
(VII)

wherein $R^1$ and $R^2$ are each independently a cyclopentadienyl ring, wherein any cyclopentadienyl ring may optionally be substituted with one or more $(C_1–C_3)$alkyl; and $R^{10}–R^{13}$ are each independently H, halo, or (C1–C6)alkyl; or a pharmaceutically acceptable salt thereof.

The invention also provides a pharmaceutical composition comprising a compound of formula II:

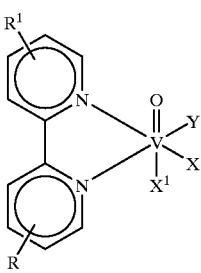
(II)

wherein R and $R^1$ are each independently H, $(C_1–C_3)$alkyl, halogen, $(C_1–C_3)$alkoxy, halo(C1–C3)alkyl, cyano, $(C_2–C_6)$ alkanoyloxy or nitro; X and are each independently a monodentate or bidentate ligand; or no ligand is present on $X^1$; and Y is a monodentate ligand, or no ligand is present on $X^1$; and Y is a monodentate ligand or a pharmaceutically acceptable salt thereof; and a pharmaceutically acceptable carrier.

The invention also provides a pharmaceutical composition comprising a compound of formula III:

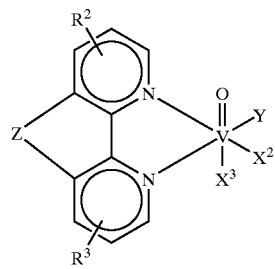
(III)

wherein $R^2$ and $R^3$ are each independently H, (C1–C3)alkyl, halogen, (C1–C3)alkoxy, halo(C1–C3)alkyl, cyano, $(C_2–C_6)$alkanoyloxy or nitro; $X^2$ and $X^3$ are each independently a monodentate or bidentate ligand, or no ligand is present on $X^3$; and Z is O, $CH_2$, $CH_2$—$CH_2$ or CH=CH; or a pharmaceutically acceptable salt thereof; and a pharmaceutically acceptable carrier; with the proviso that the compound is not $[VO(Phen)(H_2O)_2](SO_4)$.

The invention also provides a pharmaceutical composition comprising a compound of formula IV:

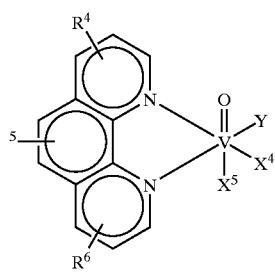
(IV)

wherein $R^4$, $R^5$ and $R^6$ are each independently H, (C1–C3) alkyl, halogen, (C1–C3)alkoxy, halo(C1–C3)alkyl, cyano, $(C_2–C_6)$alkanoyloxy or nitro; $X^4$ and $X^5$ are each independently a monodentate or bidentate ligand, or no ligand is present on $X^5$; Y is a monodentate ligand; or a pharmaceutically acceptable salt thereof; and a pharmaceutically acceptable carrier; with the proviso that the compound is not $[VO(Phen)(H_2O)_2](SO_4)$.

DETAILED DESCRIPTION

Figure 1:
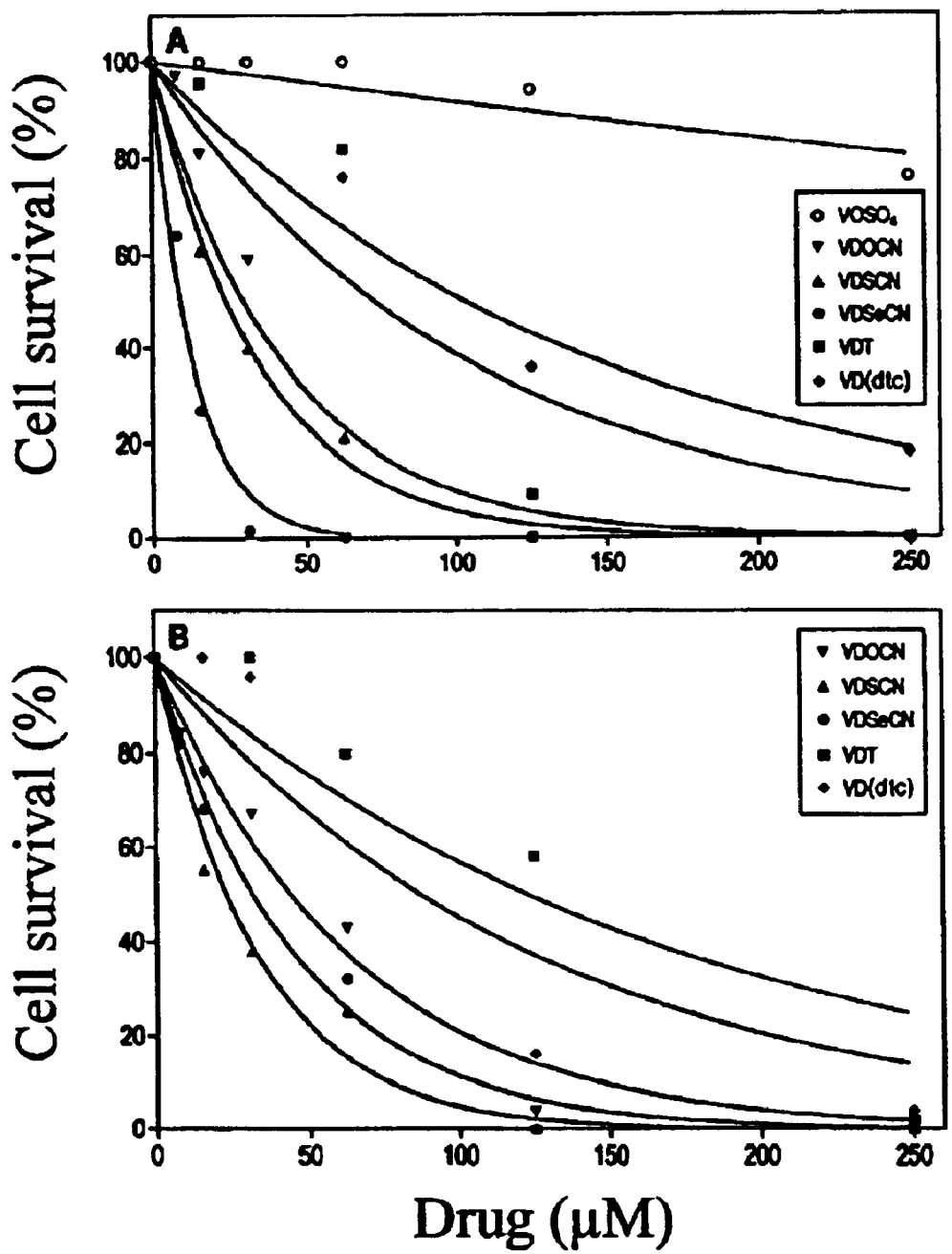
FIG. 1. Illustrates cytotoxic activity of vanadocenes on human testicular cancer cell lines with (A) Tera-2 cells and (B) Ntera-2 cells. Cells were incubated with increasing concentrations (1.9 μM–250 μM) of 5 representative vanadocenes, VDOCN, VDSCN, VDSeCN, VDT, and VD(dtc) in DMSO for 24 hr in 96-well plates and the cell survival was determined by the MTT assay as described in materials and methods. Activity is expressed relative to DMSO controls. The data points represent the mean value of triplicates. The SD for each compound was <5% of the mean values.

Vanadium is a physiologically essential element that can be found in both anionic and cationic forms with oxidation states ranging from −3 to +5 (I-V). This versatility provides unique properties to vanadium complexes. In particular, the catonic form of vanadium complexes with oxidation state +4 (IV) have been shown to function as modulators of cellular redox potential, regulate enzymatic phosphorylation, and exert pleiotropic effects in multiple biological systems by catalyzing the generation of reactive oxygen species (ROS). Besides the ability of vanadium metal to assume various oxidation states, its coordination chemistry also plays a key role in its interactions with various biomolecules. In particular, organometallic complexes of vanadium (IV) linked to bis (cycopentadienyl) moieties or vanadocene derivatives exhibit antitumor properties both in vitro and in vivo primarily via oxidative damage.

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antitumor activity using the standard tests described herein, or using other similar tests which are well known in the art.

Specific values listed below for radicals, substituents, and ranges, are for illustration only; they do not exclude other defined values or other values within defined ranges for the radicals and substituents.

Specifically, ($C_1$–$C_6$)alkyl can be methyl, ethyl, propyl, isopropyl, butyl, iso-butyl, sec-butyl, pentyl, 3-pentyl, or hexyl; ($C_1$–$C_3$)alkyl can be methyl, ethyl or propyl; halo (C1–C3)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; (C1–C3)alkoxy can be methoxy, ethoxy, or propoxy; and ($C_2$–$C_6$)alkanoyloxy can be acetoxy, propanoyloxy, butanoyloxy, isobutanoyloxy, pentanoyloxy, or hexanoyloxy.

As used herein, the following definitions define the stated terms:

"Organometallic compound" is an organic compound comprised of a metal attached directly to carbon (R-M).

"Coordination compound" is a compound formed by the union of a central metal atom or ion with ions or molecules called ligands or complexing agents.

"Ligand" or a "complexing agent" is a molecule, ion or atom that is attached to the central metal atom or ion of a coordination compound.

"Monodentate ligand" is a ligand having a single donor atom coordinated to the central metal atom or ion.

"Bidentate ligand" is a ligand having two donor atoms coordinated to the same central metal atom or ion.

"Oxovandium (IV) complex" is a coordination compound including vanadium as the central metal atom or ion, and the vanadium has an oxidation state of +4 (IV), and is double bonded to oxygen.

The present invention concerns organometallic vanadium complexes, and the finding that such oxovanadium complexes have potent and selective antitumor activity, and are particularly active and stable antitumor agents.

Compounds of the invention include oxovanadium (IV) containing organometallic complexes having antitumor activity. Preferred the oxovanadium (IV) complexes include at least one bidentate ligand. Suitable bidentate ligands include N, N; N, O; and O, O bidentate ligands. Examples of suitable bidentate ligands include bipyridyl, bridged bipyridyl, and acetophenone. Particularly, preferred oxovanadium compounds of the invention are those having the formulas II, III, IV, VI and VIII shown and described below.

Specifically, the vanadium (IV) compound is a compound of formula I:

(I)

wherein, $R_1$–$R_2$ are each independently halo, $OH_2$, $O_3SCF_3$, $N_3$, CN, OCN, SCN or SeCN;

$R_3$–$R_4$ are each independently a cyclopentadienyl ring, wherein each cyclopentadienyl ring is optionally substituted with one or more (C1–C3)alkyl.

Specifically, halo is chloro, bromo, or iodo.

Specifically, (C1–C3)alkyl is methyl.

Compounds of the invention include $VCp_2Cl_2$, $VCp_2Br_2$, $VCp_2I_2$, $VCp_2X_2$, $VCp_2(N_3)_2$, $VCp_2(CN)_2$, $VCp_2(NCO)_2$, $VCp_2(NCO)Cl$, $VCp_2(NCS)_2 \cdot 0.5H_2O$, $VCp_2(NCSe)_2$, $VCp_2Cl(CH_3CN)(FeCl_4)$, $VCp_2(O_3SCF_3)_2$, $V(MeCp)_2Cl_2 \cdot 0.5 H_2O$, $V(Me_5Cp)_2Cl_2$, $VCp_2(acac)$, $VCp_2(hf-acac)$, $VCp_2(bpy)$, $VCp_2(cat)$, $VCp_2(dtc)$, $VCp_2PH$, or $VCp_2H$.

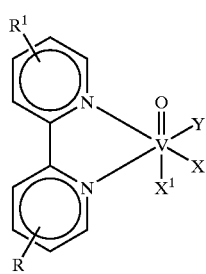

(II)

Specifically, the vanadium (IV) compound is a compound of formula II:
wherein

R and $R^1$ are each independently H, (C1–C3)alkyl, halogen, (C1–C3)alkoxy, halo(C1–C3)alkyl, cyano, ($C_2$–$C_6$)alkanoyloxy or nitro;

X and $X^1$ are each independently monodentate or bidentate ligands, or no ligand is present on $X^1$;

Y is a monodentate ligand; and

Specifically, X and $X^1$ are each independently $OH_2$, a bidentate ligand, or a monodentate ligand; wherein each ligand is optionally substituted with one or more (C1–C3)alkyl.

Specifically, (C1–C3)alkyl is methyl.

Specifically, R and $R^1$ are each independently H or (C1–C3)alkyl.

Specifically, the compound of fomula II is [VO(Bpy)($H_2O$)$_2$]($SO_4$), [VO($SO_4$)(Bpy)$_2$], [VO($Me_2$-bpy)($H_2O$)$_2$]($SO_4$), or [VO($SO_4$)($Me_2$-bpy)$_2$].

Specifically, the vanadium (IV) compound is a compound of formula III:

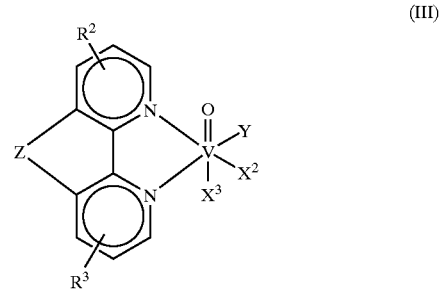

(III)

wherein $R^2$ and $R^3$ are each independently H, (C1–C3)alkyl, halogen, (C1–C3)alkoxy, halo(C1–C3)alkyl, cyano, ($C_2$–$C_6$)alkanoyloxy or nitro;

$X^2$ and $X^3$ are each independently monodentate or bidentate ligands, or no ligand is present on $X^3$;

Z is selected from O, $CH_2$, $CH_2$—$CH_2$ and CH=CH; and Specifically, Z is CH=CH.

Specifically, Y is $OH_2$ or $OSO_3$.

Specifically, $X^2$ is $OH_2$, a bidentate ligand, or a monodentate ligand.

Specifically, $X^3$ is a bidentate ligand or a monodentate ligand.

Specifically, $R^2$ and $R^3$ are each independently H, (C1–C3)alkyl, halo, or nitro.

Specifically, (C1–C3)alkyl is methyl.

Specifically, halo is chloro.

Specifically, the compound of formula III is [VO(Phen)($H_2O$)$_2$]($SO_4$), [VO($SO_4$)(Phen)$_2$], [VO($Me_2$-Phen)($H_2O$)$_2$]($SO_4$), or [VO($SO_4$)($Me_2$-Phen)$_2$].

Specifically, the vanadium (IV) compound is a compound of formula IV:

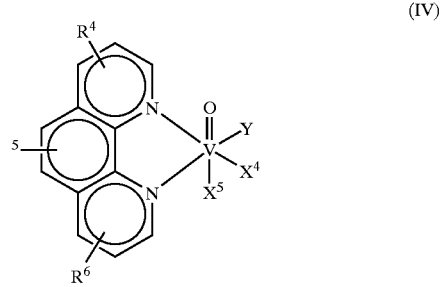

(IV)

wherein $R^4$, $R^5$ and $R^6$ are each independently H, (C1–C3)alkyl, halogen, (C1–C3)alkoxy, halo(C1–C3)alkyl, cyano, ($C_2$–$C_6$)alkanoyloxy or nitro;

$X^4$ and $X^5$ are each independently a monodentate or bidentate ligand, or no ligand is present on $X^5$;

Y is a monodentate ligand; and

Specifically, $R^4$–$R^6$ are each independently H, (C1–C3) alkyl, halo or nitro.

Specifically, (C1–C3)alkyl is methyl.

Specifically, halo is chloro.

Specifically, Y is $OH_2$ or $OSO_3$,.

Specifically, $X^5$ is $OH_2$, a bidentate ligand, or a monodentate ligand.

Specifically, the compound of formula IV is [VO(Phen)($H_2O$)$_2$](SO$_4$), [VO(SO$_4$)(Phen)$_2$], [VO(Me$_2$-Phen)($H_2O$)$_2$](SO$_4$), [VO(SO$_4$)(Me$_2$-Phen)$_2$], [VO(Cl-Phen)($H_2O$)$_2$](SO$_4$), [VO(SO$_4$)(Cl-Phen)$_2$], [VO(NO$_2$-Phen)($H_2O$)$_2$](SO$_4$), or [VO(SO$_4$)(NO$_2$-Phen)$_2$].

Specifically, the cancer is testicular cancer, Hodgkin's lymphoma, multiple myeloma, or non-Hodgkin's lymphoma.

Another specific method of the invention comprises administering an oxovanadium compound.

Another specific method of the invention comprises administering a vanadocene compound with the proviso that the vanadocene compound is not VCp$_2$Cl$_2$.

The invention provides novel compounds. Accordingly, there is provided a compound of formula II:

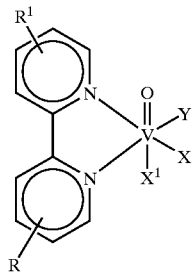

(II)

wherein

R and $R^1$ are each independently H, (C1–C3)alkyl, halogen, (C1–C3)alkoxy, halo(C1–C3)alkyl, cyano, ($C_2$–$C_6$)alkanoyloxy or nitro;

X and $X^1$ are each independently a monodentate or bidentate ligand, or no ligand is present on $X^1$; and Y is a monodentate ligand;

or a pharmaceutically acceptable salt thereof.

Specifically, X and $X^1$ are each independently $OH_2$, a bidentate ligand, or a monodentate ligand; wherein each ligand is optionally substituted with one or more (C1–C3) alkyl.

Specifically, (C1–C3)alkyl is methyl.

Specifically, R and $R^1$ are each independently H or (C1–C3)alkyl.

Specifically, the compound of fomula II is [VO(Bpy)($H_2O$)$_2$](SO$_4$), [VO(SO$_4$)(Bpy)$_2$], [VO(Me$_2$-bpy)($H_2O$)$_2$](SO$_4$), or [VO(SO$_4$)(Me$_2$-bpy)$_2$].

Another specific compound of the present invention is a compound of formula III:

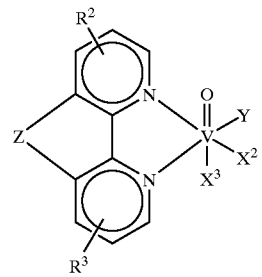

(III)

wherein $R^2$ and $R^3$ are each independently H, (C1–C3)alkyl, halogen, (C1–C3)alkoxy, halo(C1–C3)alkyl, cyano, ($C_2$–$C_6$)alkanoyloxy or nitro;

$X^2$ and $X^3$ are each independently a monodentate or bidentate ligand, or no ligand is present on $X^3$; and Z is O, CH$_2$, CH$_2$—CH$_2$ or CH=CH;

or a pharmaceutically acceptable salt thereof;

with the proviso that the compound is not [VO(Phen)($H_2O$)$_2$](SO$_4$) or [VO(SO$_4$)(Phen)$_2$].

Specifically, Z is CH=CH.

Specifically, Y is $OH_2$ or $OSO_3$.

Specifically, $X^2$ is $OH_2$, a bidentate ligand, or a monodentate ligand.

Specifically, $X^3$ is a bidentate ligand or a monodentate ligand.

Specifically, $R^2$ and $R^3$ are each independently H, (C1–C3)alkyl, halo, or nitro.

Specifically, (C1–C3)alkyl is methyl.

Specifically, halo is chloro.

Specifically, the compound of formula III is [VO(Phen)($H_2O$)$_2$](SO$_4$), [VO(SO$_4$)(Phen)$_2$], [VO(Me$_2$-Phen)($H_2O$)$_2$](SO$_4$), or [VO(SO$_4$)(Me$_2$-Phen)$_2$].

Another specific compound of the present invention is a compound of formula IV:

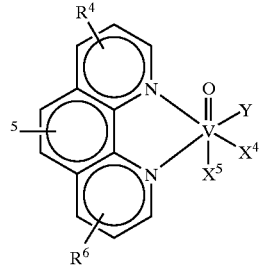

(IV)

wherein $R^4$, $R^5$ and $R^6$ are each independently H, (C1–C3)alkyl, halogen, (C1–C3)alkoxy, halo(C1–C3)alkyl, cyano, ($C_2$–$C_6$)alkanoyloxy or nitro;

$X^4$ and $X^5$ are each independently a monodentate or bidentate ligand; and

Y is a monodentate ligand or a pharmaceutically acceptable salt thereof;

with the proviso that the compound is not [VO(Phen)($H_2O$)$_2$](SO$_4$) or [VO(SO$_4$)(Phen)$_2$].

Specifically, $R^4$–$R^6$ are each independently H, (C1–C3) alkyl, halo or nitro.

Specifically, (C1–C3)alkyl is methyl.

Specifically, halo is chloro.

Specifically, Y is $OH_2$ or $OSO_3$,.

Specifically, $X^5$ is $OH_2$, a bidentate ligand, or a monodentate ligand.

Specifically, the compound of formula IV is [VO(Phen)$(H_2O)_2](SO_4)$, [VO(SO_4)(Phen)_2], [VO(Me_2-Phen)(H_2O)_2](SO_4), [VO(SO_4)(Me_2-Phen)_2], [VO(Cl-Phen)(H_2O)_2](SO_4), [VO(SO_4)(Cl-Phen)_2], [VO(NO_2-Phen)(H_2O)_2](SO_4), or [VO(SO_4)(NO_2-Phen)_2].

Another specific compound of the present invention is a compound of formula V:

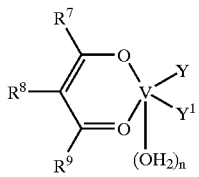

(V)

wherein $R^7$ and $R^9$ are each independently H, (C1–C3)alkyl, (C1–C3)alkoxy, or halo(C1–C3)alkyl;

$R^8$ is H, (C1–C3)alkyl, halo, (C1–C3)alkoxy, or halo (C1–C3)alkyl;

Y and $Y^1$ are each independently a monodentate or bidentate ligand; and n is 0 or 1;

or a pharmaceutically acceptable salt thereof.

Another specific compound of the present invention is a compound of formula VII:

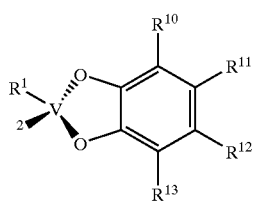

(VII)

wherein $R^1$ and $R^2$ are each independently a cyclopentadienyl ring, wherein any cyclopentadienyl ring may optionally be substituted with one or more (C1–C6)alkyl; and $R^{10}$–$R^{13}$ are each independently H, halo, or (C1–C6) alkyl;

or a pharmaceutically acceptable salt thereof.

Specifically, $R^1$ and $R^2$ are each a cyclopentadienyl ring.

Specifically, $R^{10}$–$R^{13}$ are each H.

Specifically, the compound of formula VII is the compound $Cp_2V(O_2C_6H_4)$.

A specific pharmaceutical composition of the present invention comprises a compound of formula II:

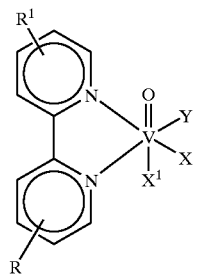

(II)

wherein

R and $R^1$ are each independently H, (C1–C3)alkyl, halogen, (C1–C3)alkoxy, halo(C1–C3)alkyl, cyano, $(C_2–C_6)$alkanoyloxy or nitro;

X and are each independently a monodentate or bidentate ligand, or no ligand is present on $X^1$; and Y is a monodentate ligand;

or a pharmaceutically acceptable salt thereof;

and a pharmaceutically acceptable carrier.

Specifically, X and $X^1$ are each independently $OH_2$, a bidentate ligand, or a monodentate ligand, wherein each ligand is optionally substituted with one or more (C1–C3) alkyl.

Specifically, (C1–C3)alkyl is methyl.

Specifically, R and $R^1$ are each independently H or (C1–C3)alkyl.

Specifically, the compound of fomula II is [VO(Bpy)$(H_2O)_2](SO_4)$, [VO(SO_4)(Bpy)_2], [VO(Me_2-bpy)(H_2O)_2](SO_4), or [VO(SO_4)(Me_2-bpy)_2].

Another specific pharmaceutical composition of the present invention comprises a compound of formula III:

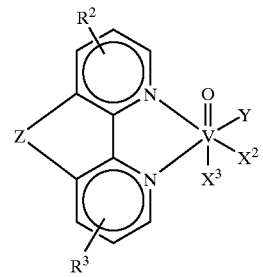

(III)

wherein $R^2$ and $R^3$ are each independently H, (C1–C3)alkyl, halogen, (C1–C3)alkoxy, halo(C1–C3)alkyl, cyano, $(C_2–C_6)$alkanoyloxy or nitro;

$X^2$ and $X^3$ are each independently a monodentate or bidentate ligand, or no ligand is present on $X^3$; and Z is O, $CH_2$, $CH_2$—$CH_2$ or CH=CH;

or a pharmaceutically acceptable salt thereof, and a pharmaceutically acceptable carrier;

with the proviso that the compound is not [VO(Phen)$(H_2O)_2](SO_4)$.

Specifically, Z is CH=CH.

Specifically, Y is $OH_2$ or $OSO_3$.

Specifically, $X^2$ is $OH_2$, a bidentate ligand, or a monodentate ligand.

Specifically, $X^3$ is a bidentate ligand or a monodentate ligand.

Specifically, $R^2$ and $R^3$ are each independently H, (C1–C3)alkyl, halo, or nitro.

Specifically, (C1–C3)alkyl is methyl.

Specifically, halo is chloro.

Specifically, the compound of formula III is [VO(Phen)(H$_2$O)$_2$](SO$_4$), [VO(SO$_4$)(Phen)$_2$], [VO(Me$_2$-Phen)(H$_2$O)$_2$](SO$_4$), or [VO(SO$_4$)(Me$_2$-Phen)$_2$].

Another pharmaceutical composition of the present invention comprises a compound of formula IV:

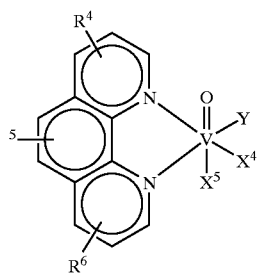

wherein $R^4$, $R^5$ and $R^6$ are each independently H, (C1–C3)alkyl, halogen, (C1–C3)alkoxy, halo(C1–C3)alkyl, cyano, (C$_2$–C$_6$)alkanoyloxy or nitro;

$X^4$ and $X^5$ are each independently a monodentate or bidentate ligand; and

Y is a monodentate ligand;

or a pharmaceutically acceptable salt thereof;

and a pharmaceutically acceptable carrier;

with the proviso that the compound is not [VO(Phen)(H$_2$O)$_2$](SO$_4$).

Specifically, $R^4$–$R^6$ are each independently H, (C1–C3)alkyl, halo or nitro.

Specifically, (C1–C3)alkyl is methyl.

Specifically, halo is chloro.

Specifically, Y is OH$_2$ or OSO$_3$,.

Specifically, $X^5$ is OH$_2$, a bidentate ligand, or a monodentate ligand.

Specifically, the compound of formula IV is [VO(Phen)(H$_2$O)$_2$](SO$_4$), [VO(SO$_4$)(Phen)$_2$], [VO(Me$_2$-Phen)(H$_2$O)$_2$](SO$_4$), [VO(SO$_4$)(Me$_2$-Phen)$_2$], [VO(Cl-Phen)(H$_2$O)$_2$](SO$_4$), [VO(SO$_4$)(Cl-Phen)$_2$], [VO(NO$_2$-Phen)(H$_2$O)$_2$](SO$_4$), or [VO(SO$_4$)(NO$_2$-Phen)$_2$].

Administration of the compounds as salts may be appropriate. Examples of acceptable salts include alkali metal (for example, sodium, potassium or lithium) or alkaline earth metal (for example calcium) salts, however, any salt that is non-toxic and effective when administered to the animal being treated is acceptable.

Acceptable salts may be obtained using standard procedures well known in the art, for example by reacting a sufficiently acidic compound with a suitable base affording a physiologically acceptable anion.

The compositions of the invention can be formulated as pharmaceutical compositions and administered to an animal host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained. When administered orally, the compositions of the invention can preferably be administered in a gelatin capsule.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compositions of the invention may also be administered intravenously or intraperitoneally by infusion or injection. Solutions of the active composition can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride.

Prolonged absorption of the injectable compositions can be brought about by the use in the compositions of agents delaying absorption, for example, aluminum monostearate and gelatin.

Sterile injectable solutions are prepared by incorporating the active composition in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compositions may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of nontoxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compositions of the invention in a liquid composition, such as a lotion, will be from about 0.1–50 wt-%, preferably from about 0.5–5 wt %. The concentration in a semi-solid or solid composition such as a gel or a powder will be about 0.1–5 wt-%, preferably about 0.5–2.5 wt-%.

The amount of the composition required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.1 to about 150 mg/kg, e.g., from about 10 to about 75 mg/kg of body weight per day, such as 3 to about 50 mg per kilogram body weight of the recipient per day, preferably in the range of 1 to 100 mg/kg/day, most preferably in the range of 5 to 20 mg/kg/day.

The compositions are conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compositions of the invention are useful for prevention and of cancer.

Following i.m. administration, the compositions of the invention enter the blood stream within about 10–15 minutes and reach a maximum concentration in the blood within one hour of administration, at which point they can be found throughout the circulatory related organs.

The antitumor activity of the compositions of the invention can be determined using assays that are known in the art, or can be determined using assays similar to those described in the following examples.

EXAMPLES

Abbreviations.

$Cp^-$, cyclopentadienyl anion; acac, acetonylacetonate; Bpy, 2,2' Bipyridine; Hfacac, hexafluor0acetylacetonate; Cat, catecholate; Dtc, diethyl dithio carbamate; PH, N-phenyl bezohydroxamic acids; H, acethydroxamic acid; OTf, trifluoroinetahne sulphonate; THF, tetrahydrofuran; DMSO, dimethyl sulfoxide; $CH_3CN$, acetonitrile; $CH_2Cl_2$, dichloromethane; d-d, laportte spin forbidden transitions; LMCT, ligand to metal charge transfer transitions; p-p*, intraligand charge transfer transitions; s, m, w: strong, medium, and weak; b, broad; v, very; sh, shoulder.

Materials and Methods

Reagents used were reagent grade, unless otherwise stated. All solvents were used as received from Aldrich Sure Seal bottle, <0.005% water. Tetrahydrofuran was dried by distillation over solid sodium. Dichloromethane (reagent grade) was purified as follows: stirred overnight with concentrated sulfuric acids, seperated, washed with saturated aqueous $NaHCO_3$, washed with aqueous KOH/KCl, washed with distilled water, dried over anhydrous $MgSO_4$, and distilled from KOH. Perrin, D. D., Armiereago, W. L. F. In Purification of Laboratory Chemicals, 3rd.ed.; pergamon press: New York, 1988. Sodium thiophenolate was prepared by the reaction of a stoichiometric amount of NaOMe with thiophenol in methanol. The precipitated solid was washed with cold methanol and dried under high vacuum. All the solvents were deoxygeneted by purging with argon, and reactions were carried out under an argon atmosphere by using standard Schlenk techniques.

The infra-red spectral data were recorded on a FT-Nicolet model Protege 460. The solid samples were taken in a KBr pellet and the frequencies were generally in the range of 4000–500 $cm^{-1}$. UV-vis spectra were recorded in a quartz cell or cuvette on Beckman model DU 7400 spectrophotometer and the spectral band are registered between 250–800 nm range. NMR spectra were recorded in CDCl$_3$ or Me$_2$SO-d$^6$ on a Varian (300 Mhz) NMR spectrometer. Chemical shifts are reported as δ values downfield from an internal standard of Me$_4$Si. Melting points were determined with Melt-temp laboratory devices Inc. apparatus, attached to Fluke 51 K/J Thermometer.

All elemental analysis were performed by Atlantic Microlab, Inc., Norcross, Ga., and the analytical results are supplied as supporting information. unless otherwise stated all operations were carried out at room temperature.

Example 1

Vanadocene Compounds
Chemical Synthesis

All the metal tetrachlorides, MCl$_4$ (M=Ti, V, Mo, Hf, & Zr) were purchased from Aldrich Chemical Co. (Milwaukee, Wis.).

Compounds 1–25 are shown in Synthetic Schemes 1–4 and Tables 1–4. VCp$_2$Cl$_2$, TiCp$_2$Cl$_2$, ZrCp$_2$Cl$_2$, and MoCp$_2$Cl$_2$ were prepared by known procedures. Wilkinson, G., Birmingham, J. M. Bis-cyclopentadienyl compounds of Ti, Zr, V, Nb, and Ta. J. Am. Chem. Soc., 76: 4281–4284, 1954. Cardin, D. J., Lappart, M. F., Raston, C. L., Riley, P. I. In Comprehensive organometallic chemistry; Wilkinson, G. ed. New York: Pergamon; 3: 554–646, 1982. Eisch, J. J., King, R. B. Organometallic synthesis, Academic press, New York, N.Y. Vol. 1, 75–76, 1965. The purity was checked by $^1$HNMR and IR spectroscopy and by elemental analysis. The HfCp$_2$Cl$_2$ was directly purchased from aldrich Chemical Co. The complex VCp$_2$Cl$_2$ was purified by anaerobic Soxhlet extraction with CH$_2$Cl$_2$ at 44° C. (under partial vacuum). TiCp$_2$Cl$_2$ was recrystallized from THF.

Compounds 1–5 may be prepared as shown in Synthetic Scheme 1; compounds 6–15 may be prepared as shown in Synthetic Scheme 2; compounds 16–22 may be prepared as shown in Synthetic Scheme 3; and compounds 23–25 may be prepared as shown in Synthetic Scheme 4 (below).

HfCp$_2$Cl$_2$, (Compound 1). Yield: 75%. M.P. 330–335° C. Anal. Calcd. for HfC$_{10}$H$_{10}$Cl$_2$: C, 31.62, H, 2.63; Cl, 18.71. Found: C, 32.09; H, 2.75; Cl, 18.98. UV-vis (CH$_2$Cl$_2$) λ$_{max}$: 312 (LMCT), 268, 232 (π-π*) nm. IR (KBr Disc): 3105(vs), 1365(m), 1126(m), 1014(vs), 920(s,d), 802(vs), 816(vs), 611(m) cm$^{-1}$. $^1$HNMR (δ ppm, CDCl$_3$): 6.37 (s, 10H, 2×C$_5$H$_5$).

MoCp$_2$Cl$_2$, (Compound 2). Yield: 37%. M.P. 220° C. Anal. Calcd. for MoC$_{10}$H$_{10}$Cl$_2$: C, 40.4, H, 3.37; Cl, 23.9. Found: C, 40.8; H, 3.39; Cl, 24.4. UV-vis: (DMSO) λ$_{max}$: 678, 436 (d-d), 299 (LMCT), 283, 267 (π-π*) nm. IR (KBr Disc): 3093(vs), 1420(vs), 1375(m), 1100(m), 1060(m), 825(vs,d), 590(m) cm$^{-1}$. $^1$HNMR (δ ppm, DMSO-d$^6$): 6.27 (s, 10H, 2×C$_5$H$_5$).

TiCp$_2$Cl$_2$, (Compound 3). Yield: 45%. M.P. 290° C. (decomposes). Anal. Calcd. for TiC$_{10}$H$_{10}$Cl$_2$: C, 48.2, H, 4.01; Cl, 28.5. Found: C, 48.56; H, 4.03; Cl, 28.78. UV-vis: (CH$_2$Cl$_2$) λ$_{max}$: 526, 391 (LMCT), 314, 255 (π-π*) nm. IR (KBr Disc): 3105(m), 1441(s), 1368(m), 1130(m), 1016(vs), 956(m), 872(s), 820(vs)) cm$^{-1}$. $^1$HNMR (δ ppm, CDCl$_3$): 6.57 (s, 10H, 2×C$_5$H$_5$).

ZrCp$_2$Cl$_2$, (Compound 4). Yield: 78%. M.P. 240–245° C. (decomposes). Anal. Calcd. for ZrC$_{10}$H$_{10}$Cl$_2$: C, 41.09, H, 3.4; Cl, 24.31. Found: C, 41.01; H, 3.4; Cl, 24.84. UV-vis: (CH$_2$Cl$_2$) λ$_{max}$: 341 (LMCT), 294, 236 (π-π*) nm. IR (KBr Disc): 3104(m), 1435(s), 1363(m), 1122(m), 1014(vs), 815 (s), 850(sb), 610(m)) cm$^{-1}$. $^1$HNMR (δ ppm, CDCl$_3$): 6.46 (s, 10H, 2×C$_5$H$_5$).

VCp$_2$Cl$_2$, (Compound 5). Yield: 55%. M.P. 248–255° C. (decomposes). Anal. Calcd. for VC$_{10}$H$_{10}$Cl$_2$: C, 47.62, H, 3.97; Cl, 28.1. Found: C, 47.88; H, 4.04; Cl, 27.64. UV-vis: (CH$_2$Cl$_2$) λ$_{max}$: 776, 647 (d-d), 380 (LMCT), 283, 244 (π-π*) nm. IR (KBr Disc): 3095(s), 1444(s), 1433(s), 1368 (m), 1363(m), 1130(m), 1070(m), 1010(m), 887(m), 825(vs) cm$^{-1}$.

VCp$_2$Br$_2$, (Compound 6). To a 20 ml acetone solution of VCp$_2$Cl$_2$ (0.2 g, 8 mmol) was added 0.7 g (80 mmol) of solid LiBr with stirring, and the reaction mixture was allowed to reflux for 4 h. The solvent was removed afterwards through vacuum and dried. The deep green product was extracted with 50 ml of boiling CHCl$_3$ and the solution was saturated with dry HBr gas before it was left overnight for crystallization at −20° C. The bright green crystals were collected on a frit and washed with hexane and diethyl ether. Yield: 90%. M.P. turns darker gradually over the range 250–350° C. (decomposes). Anal. Calcd. for VC$_{10}$H$_{10}$Br$_2$: C, 35.19, H, 2.29; Br, 46.92. Found: C, 35.19; H, 2.9; Br, 46.91. UV-vis: (CH$_2$Cl$_2$) λ$_{max}$: 773, (d-d), 412 (LMCT), 298, 232 (π-π*) nm. IR (KBr Disc): 3089(vs), 1425(s), 1431(m), 1373(m), 1363(w), 1128(w), 1024(m), 1014(m), 887(m), 825(vs) cm$^{-1}$.

VCp$_2$I$_2$, (Compound 7). To anhydrous THF (25 mL) were added VCp$_2$Cl$_2$ (0.15 g, 6 mmol) and KI (0.99 g, 60 mmol). This reaction mixture was refluxed overnight under argon. The resulting dark red-brown solution was seperated from the inorganic salts by filtration and the solvent was evaporated under vacuum. The dark red materials were scratched out from the bottom of the container in the presence of dry hexane. The solvent was removed by cannula techniques with double edged needles under argon pressure. The solid was dried under vacuum and stored under argon. This compound is extremely sensitive to moisture and readily decomposes in halogenated solvents, but it is stable in DMSO. Yield: 55%. M.P.: Could not be measured; compound gets sticky during handling in air. Anal.Calcd.for VC$_{10}$H$_{10}$I$_2$: C, 27.58; H, 2.3; 1, 58.4. Found: C, 28.1; H, 2.42; 1, 58.9 UV-Vis: (CH$_2$Cl$_2$) λ$_{max}$: 620, 552, (d-d), 352 (LMCT), 296, 232,(π-π*) nm. IR (KBr Disc): 3300 (vb), 3095(s), 2950(s), 1712(w), 1574(w), 1425(s), 1431(m), 1373(m) 1363(w), 1182(m), 1128(w), 1024(m), 1014(m), 887(m), 825(vs) cm$^{-1}$.

VCp$_{2\times 2}$. The pseudo-halide derivatives with X=N$_3^-$ (Compound 8), CN$^-$ (Compound 9), OCN$^-$ (Compound 10), and SCN$^-$ (Compound 12) were prepared by following the procedure described in Doyle, G., Tobias, R. S. Pseudohalide and chelate complexes of bis(cyclopentadienyl) vanadium(IV). Inorg. Chem., 7: 2479–2484, 1968. The pure compounds were isolated either recrystallization or from Soxhlet extraction. The purity of these complexes were checked by elemental analysis, melting point data and UV-visible and IR spectrum. The results are given below:

VCp$_2$(N$_3$)$_2$, (Compound 8). Yield: 65%. M.P. Sublimes at 173° C. (decomposes). Anal. Calcd. for VC$_{10}$H$_{10}$N$_6$: C, 45.28, H, 3.77; N, 31.2. Found: C, 45.28; H, 3.73; N, 31.16. UV-vis: (CH$_2$Cl$_2$) λ$_{max}$: 434 (d-d), 314 (LMCT), 257, 233 (π-π*) nm. IR (KBr Disc): 3125(m), 3111(m), 3104(m), 3079(m), 2067(vs), 2031(vs), 1448(m), 1375(m), 1330(m), 1280(m), 1126(w), 1080(w), 1024(m), 835(vs), 646(w), 590(m), 438(m), 400(w) cm$^{-1}$.

VCp$_2$(CN)$_2$, (Compound 9). Yield: 75%. M.P. Sublimes at 173° C. (decomposes). Anal. Calcd. for VC$_{12}$H$_{10}$N$_2$: C, 61.89, H, 4.29; N, 12.0. Found: C, 60.98; H, 4.30; N, 11.45. UV-vis: (CH$_2$Cl$_2$) λ$_{max}$: 605 (d-d), 394 (LMCT), 307, 250 (π-π*) nm. IR (KBr Disc): 3450(m,b), 3114(vs), 2120(s), 2110(s), 1435(s), 1420(s), 1369(m), 1373(w), 1126(m), 1014(s), 881(s), 858(vs), 845(vs), 480(m), 400(m) cm$^{-1}$.

VCp$_2$(NCO)$_2$, (Compound 10). Yield: 55%. M.P. 287° C. (decomposes). Anal. Calcd. for VC$_{12}$H$_{10}$N$_2$O$_2$: C, 54.3, H, 3.8; N, 10.6. Found: C, 53.85; H, 3.97; N, 10.2. UV-vis: (CH$_2$Cl$_2$) $\lambda_{max}$: 742 (d-d), 373 (LMCT), 277, 237 ($\pi$-$\pi$*) nm. IR (KBr Disc): 3531(m), 3110(m), 2657(w), 2248(vs), 2117(vs), 2170(vs), 1330(s), 1024(w), 833 (vs), 603(s), 593 (s), 420(m) cm$^{-1}$.

VCp$_2$(NCO)Cl, (Compound 11). The dark brown powder was isolated by following the procedure described for the Titanium analogue. Köpf-Maier, P., Grabowski, S., Köpf, H. Tumorhemmung durch Metallocene: Titan-Komplexe des type [TiCp$_2$XY] und [TiCpX$^2$Y]. Eur. J.Med.Chem-Chim. Ther. 19: 347–352, 1984. Anal. Calcd. for VC$_{11}$H$_{10}$NOCl: C, 51.06, H, 3.87; N, 5.41, Cl, 13.73. Found: C, 51.35; H, 3.97; N, 5.65, Cl, 13.45. UV-vis: (CH$_2$C12) $\lambda_{max}$: 710 (d-d), 490 (LMCT), 257,227 ($\pi$-$\pi$*) nm. IR (KBr Disc): 3513(sp, w), 3110(m), 2657(w), 21 17(vs), 1444(m), 1330(s), 1261 (w), 1018(m), 950(m), 833 (vs), 635(s), 424(w) cm$^{-1}$.

VCp$_2$(NCS)$_2$. 0.5H$_2$O, (Compound 12). Yield: 75%. M.P. The compound sublimes at 150° C. (decomposes). Anal. Calcd. for VC$_{12}$H$_{11}$N$_2$O$_{1/2}$S$_2$:C, 47.05, H, 3.59; N, 9.15, S, 20.91. Found: C, 47.55; H, 3.26; N, 9.06; S, 20.91. UV-vis: (CH$_2$Cl$_2$) $\lambda_{max}$: 739 (d-d), 401 (LMCT), 463 (SCN$^-$: $\pi$-$\pi$*), 251, 270 ($\pi$-$\pi$*) nm. IR (KBr Disc): 3400(w,b), 3087(s), 2086(vs), 2067(vs), 1433(s), 1423(m), 1010(m), 1070(m) 840(vs), 480(vw), 410(m) cm$^{-1}$.

VCp$_2$(NCSe)$_2$, (Compound 13). To a stirring solution of VCp$_2$Cl$_2$, (0.4 g, 1.6 mmol) in anhydrous acetone (25 ml) under argon, was added solid KNCSe (0.85 g, 8 mmol). The reaction mixture was allowed to stir for 4 h at room temperature. The resulting red brown solution was subjected to rotatory vaporization and the pure microcrystalline red compound was isolated from the crude product through Soxhlet extraction using dichloromethane as solvent. Yield: 60%. M.P. The compound slowly turns black, decomposes at 250–275° C. (decomposes). Anal. Calcd. for VC$_{12}$H$_{10}$N$_2$Se$_2$:C, 36.83, H, 2.56; N, 7.1. Found: C, 36.85; H, 2.64; N, 6.97. UV-vis: (CH$_2$Cl$_2$) $\lambda_{max}$: 716 (d-d), 456 (LMCT), 488 (SeCN$^-$: $\pi$-$\pi$*), 251, 270 ($\pi$-$\pi$*) nm. IR (KBr Disc): 3475(m), 3076(s), 2085(vs), 2065(vs), 1444(m), 1431 (s), 1126(w), 1074(w), 1008(m), 962(m) 843(vs) cm$^{-1}$.

VCp$_2$Cl (CH$_3$CN)(FeCl$_4$), (Compound 14). Compound (14) was prepared by following the procedure described for the corresponding titanium complex. Neuse, E. W., Meirim, M. G. A chlorotitanocene tetrachlorferrate complex stabilized by acetonitrile coordination. Transition Met. Chem., 9: 337–338, 1984. In the instant synthesis, the 1:1.1 stoichiometric mole ratio between VCp$_2$Cl$_2$ and anhydrous FeCl$_3$ solution was strictly maintained in acetonitrile solution. The dark green precipitate was isolated from the reduced volume of the parent solution after overnight standing at –20° C. Yield: 90%. M.P. Not determined. Anal. Calcd. for: VC$_{12}$H$_{13}$NCl$_5$Fe: C, 31.6; H, 2.9; N, 3.1; Cl, 39.98. Found: yet to receive the data. UV-Vis: (CH$_3$CN) $\lambda_{max}$: 648, 575, (d-d), 362 (Superimposed bands of LMCT of Cp$_2$V$^{2+}$ and FeCl$_4^-$), 31 1 (FeCl$_4^-$, LMCT), 265(sh), ($\pi$-$\pi$* of Cp rings), 240 (superimposed bands of $\pi$-$\pi$* of Cp rings and FeCl$_4^-$ nm. IR (KBr Disc): 3386(sb), 3109(m), 2924(m), 2360(w), 2318(s), 2289(m), 1622(m), 1447(s), 1435(m), 1358(w), 1128(m), 1027(s), 1012(s), 856(vs), 846(s) cm$^{-1}$.

VCp$_2$(O$_3$SCF$_3$)$_2$, (Compound 15). The generation of VCp$_2$(O$_3$SCF$_3$)$_2$ in THF solution was induced by following the procedure that was described for Titanium analogue. Thewalt, U., Berhalter, K. Kationische Komplexe Mit Der ($\eta^5$–C$_5$H$_5$)$_2$Ti$^{IV}$-Baugruppe: Darstellung und Struktur Von [($\eta^5$–C$_5$H$_5$)$_2$ Ti(bpy)]$^{2+}$ (CF$_3$SO$_3^-$)$_2$. J. Organometallic Chem., 302: 193–200, 1986. The precipitated silver chloride was removed by filtration and the filtrate evaporated to dryness. The solid green residue was redissolved in 20 mL of CH$_2$Cl$_2$, filtered again through cannula with one end covered with filter paper—cotton assembly, securely tightened by fine bore copper wire. The dark green precipitate was isolated from dichloromethane using diethyl ether as a cosolvent. The compound is moisture-sensitive. Yield: 40%, m.p. at 137° C. decomposition starts. Anal. Calcd.for VC$_{12}$H$_{10}$S$_2$O$_6$F$_6$: C, 30.06; H, 2.09; S, 13.36. Found: C, 29.98; H, 2.18; S, 13.19. UV-Vis: (DMSO) $\lambda_{max}$: 620 (d-d), 379 (LMCT), 286, 261 ($\pi$-$\pi$*) IR (KBr Disc): 3400(s,b), 3093(m), 1635(m), 1446(s), 1436(s), 1259(vb,d) 1178(vs), 1033(vs), 885(s), 822(vs), 770 (m), 643(vs,d), 580, (m), 518(vs) cm$^{-1}$.

VCp$_2$(acac)(O$_3$SCF$_3$), (Compound 16). Dark black colored large crystals were obtained by following the literature procedure. Doyle, G., Tobias, R. S. Pseudohalide and chelate complexes of bis(cyclopentadienyl)vanadium(IV). Inorg. Chem., 7:2479–2484, 1968. Yield: 45%, M.P. 247° C. decomposition starts. Anal. Calcd.forVC$_{16}$H$_{17}$SO$_5$F$_3$: C, 44.45; H, 3.96; S, 7.46. Found: C, 44.81; H, 3.99; S, 7.52. UV-Vis: (CH$_2$Cl$_2$) $\lambda_{max}$: 740, 640 (d-d), 370 (LMCT), 309 ($\pi$-$\pi$* of acac$^-$ moiety), 270, 230 ($\pi$-$\pi$* of Cp$^-$ rings). IR (KBr Disc): 3118(s), 2295(w), 1564(vs), 1516(vs), 1440(s), 1350(s), 1267(s,b) 1194(w), 1149 (vs) 1067(w), 1032(s), 983(w), 959(w), 910(w), 843(vs), 783(vs),756(m), 638(m), 573(vs), 456(s), 408(m) cm$^{-1}$.

VCp$_2$(Hfacac)(O$_3$SCF$_3$), (Compound 17). Micro dark green powder was isolated following the procedure described Doyle, G., Tobias, R. S. Pseudohalide and chelate complexes of bis(cyclopentadienyl)vanadium(IV). Inorg. Chem., 7:2479–2484, 1968. Yield: 20%, M.P. 225° C. decomposition starts. Anal. Calcd.for VC$_{16}$H$_{11}$SOSF$_9$: C, 35.89; H, 2.06; S, 5.98. Found: C, 35.76; H, 2.08; S, 5.89. UV-Vis: (CH$_2$Cl$_2$) $\lambda_{max}$: 700, 557 (d-d), 377 (LMCT), 314 ($\pi$-$\pi$* of Hfacac$^-$ moiety), 271, 244 ($\pi$-$\pi$* of Cp$^-$ rings). IR (KBr Disc): 3117(m), 1637(vs), 1597(w), 1552(w), 1523 (w), 1446(s), 1358(w), 1267(s,b) 1194 (w), 1149(vs) 1067 (w), 1032(s), 983(w), 959(w), 910(w), 843(vs), 783(vs),756 (m), 638(m), 573(vs), 456(s), 408(m) cm$^{-1}$.

VCp$_2$(bpy)(O$_3$SCF$_3$)$_2$, (Compound 18). The synthetic procedure was a modified procedure described for TiCp$_2$(bpy)(O$_3$SCF$_3$)$_2$. Thewalt, U., Berhaltel, K. Kationische Komplexe Mit Der ($\eta^5$–C$_5$H$_5$)$_2$Ti$^{IV}$-Baugruppe: Darstellung und Struktur Von [($\eta^5$–C$_5$H$_5$)$_2$ Ti(bpy)]$^{2+}$ (CF$_3$SO$_3^-$)$_2$. J. Organometallic Chem., 302: 193–200, 1986. Light grayish powder was obtained as a precipitate from the THF solution which was collected by filtration and dried. Yield: 38%. M.P. 305° C. Anal Calcd. for VC$_{24}$H$_{20}$N$_2$F$_6$O$_6$VS: C, 53.1; H, 3.69; N, 2.58; S, 5.9. Found: C, 52.48; H, 3.72; N, 2.51; S, 5.73. UV-Vis (DMSO) $\lambda_{max}$: 780(sh), 555(d-d), 326 (LMCT of Cp$_2$V$^{2+}$), 272(sh) ($\pi$-$\pi$* of Cp ring), 241 (superimposed bands of $\pi$-$\pi$* of Cp rings and bipyridine) nm. IR (cm–1): 3135(m), 3099(s), 1605(vs), 1504(m), 1477(s), 1452(s), 1437(vs),1307(m), 1257(vs) 1232(vs), 1207(m), 1028(vs), 862 (vs), 837(w), 771(vs), 636(vs), 517(vs), 435(vw) cm$^{-1}$.

Cp$_2$V(cat), (Compound 19). Cp$_2$VCl$_2$ (126 mg, 0.50 mmol) was placed in a 250 mL flask and dissolved in THF (100 mL). In another flask the sodium catecholate (Cat) was prepared by the addition of NaH (25 mg, 1.0 mmol, mineral oil had been previously removed by washing with petrolium ether) catechol (to 55.5 mg, 0.50 mmol) in THF (15 mL). The solution was stirred for 2 hours, resulting in a deep blue solution. The catecholate solution was cannulated into the vanadium solution and stirred for 4 hours. The reaction mixture was opened to the air and quickly flash chromatographed under nitrogen on alumina (neutral) (acetonitrile moblie phase). The solvent of the deep blue solution was then removed under vacuum and the product collected. Yield: 26%. M.P. Not determined. Anal. Calcd. for $VC_{16}H_{14}O_2$: C, 66.45; H, 4.88. Found: C, 66.79; H, 4.93. UV-vis $(CH_3CN)\lambda_{max}$: 711 (2078), 438 (2041) (LMCT of Cat-V(IV)), 337 (3173) (LMCT of Cp-V(IV)), 292 (8564), 275 (14661), 259 (18945) (π-π* of Cat and Cp rings). IR (KBr pellet): 3100(w), 3080(w), 2951(m), 2945(w), 2860 (w), 1468(s), 1438(m), 1404(m), 1359(w) 1261(vs), 1012 (w), 929(w), 804(vs), 638(w) $cm^{-1}$.

$VCp_2(dtc)$, (Compound 20). Bis(cyclopendienyle)N,N-diethyl dithiocarbamato triflate salt was prepared according to the published procedure. Casey, A. T., Thackeray, J. R. Dithiochelates of the Bis(h-cyclopentadienyl)vanadium (IV) moiety. II N,N-Dialkyldithiocarbainate and O,O'-dialkyldithiophospahte complexes. Aust. J. Chem. 27: 757–768, 1974. Yield : 90%. M.P. 163° C. Anal. Calcd. for $VC_{16}H_2OS_3F$ : C, 48.09; H, 3.93; N, 2.75; S, 24.36. Found: C, 48.11; H, 3.97; N, 2.79; S, 24.41. UV-vis $(CH_3CN)$ $\lambda_{max}$: 621, 535 (d-d), 392 (LMCT), 330 (Dtc$^-$: π-π*), 276, 270, 230 (π-π* of Cp and Dtc$^-$). IR (KBr pellet): 3107(m), 1632(s), 1595(w), 1538(w), 1439(s), 1212(s), 1201(s), 1156 (s), 1123(m), 1019(s), 855(s), 641(s) $cm^{-1}$.

$VCp_2(PH)$, (Compound 21). The reaction mixture composed of $VCp_2Cl_2$ (0.2 g, 8 mmol) and $AgCF_3SO_3$ (0.46 g, 18 mmol) in $H_2O$ (10 mL) was stirred for 2 h and then filtered through fine glass frit. A solution of N-phenyl benzohydroxamic acid in 5 mL ethanol, 0.85 g, 4.0 mmol, was added to the filtrate with stirring, and the resulting solution was kept for 4 h to complete the precipitation of dark colored compound. These were collected by filtration and throughly washed with diethyl ether and dried for overnight under vacuum. Yield: 38%. M.P. 160° C. Anal Calcd. for $VC_{24}H_{20}NF_3O_5S$: C, 53.1; H, 3.69; N, 2.58; S, 5.9. Found: C, 52.48; H, 3.72; N, 2.51; S, 5.73. UV-Vis: $(CH_2Cl_2)$ $\lambda_{max}$: 680, 501 (d-d), 377 (LMCT), 314 (π-π* of hydroxamate moiety), 261, 233 (π-π* of Cp ring) nm. IR $(cm^{-1})$: 3345(sb), 3117(s), 1651(mb), 1600(m), 1539((vs), 1495(m), 1450(m), 1300(m), 1281(s), 1244(vs), 1173(s), 999(m), 758(m), 694((m), 638((s), 578(w), 515(m) $cm^{-1}$.

$VCp_2(H)$, (Compound 22). This reddish-brown compound was prepared following the procedure applied for the compound (20). D'Cruz, O. J., Ghosh, P., Uckun, F. M. Antitumor activity of chelated complexes of bis (cyclopentadienyl)vanadium(IV). Mol. Hum. Reprod., 4: 683–693, 1998. In the instant synthesis, the reactions were carried out in dry THF instead of $H_2O$ using acethydroxamic acid as ligand. Yield: 52%. M.P. Could not be determined because it absorbs moisture from the air and turns pasty within few minutes. Anal Calcd. for $VC_{13}H_{14}NF_3O_5S$: C, 38.61; H, 3.46; N, 3.46; S, 7.92. Found: C, 38.12; H, 3.72; N, 3.26; S, 7.81. UV-Vis: $(CH_2Cl_2)$ $\lambda_{max}$: 710, 550 (d-d), 401 (LMCT), 300 (π-π* of hydroxamate moiety), 261, 233 (π-π* of Cp ring)nm. IR (Kbr Disc): 3345(s,vb), 1695(mb), 1635 (m), 1500((vs), 1450(s), 1280(m), 1260(s), 1215(vs), 1144 (s), 959(m), 758 (m), 635((m), 540(w), 480(m) $cm^{-1}$.

$V(MeCp)_2Cl_2$. $0.5H_2O$, (Compound 23). The synthetic procedure is described in the literature. Petersen, J. L., Dahl, L. F. Synthesis and structural characterization by X-ray diffraction and electron paramagnetic resonance single-crystal techniques of $V(\eta^5-C_5H_4CH_3)_2Cl_2$. A study of the spatial distribution of the unpaired electron in a $V(\eta_5-C_5H_5)_2$ $L_2$-type complex. J. Am. Chem. Soc., 97. 6422–6433, 1975. The bright green microcrystals were separated from the HCl saturated $CHCl_3$ solution. Yield. 25%. Anal Calcd. for $VCl_2H_{15}Cl_2O_{0.5}$: C, 49.82; H, 5.19; Cl, 24.60. Found: C, 49.92; H, 34.90; Cl, 24.90. UV-Vis $(CH_2Cl_2)$ $\lambda_{max}$: 760, 659 (d-d), 383 (LMCT of $Cp_2V^{2+}$), 286, 233 (π-π* of MeCp rings), nm. IR $(cm^-)$: 3135(m), 3099(s), 1307(m), 1028(vs), 862(vs), 771(vs), 636(vs), 517 (vs) $cm^{-1}$.

$V(Me_5CP)_2Cl_2$, (Compound 24). The green solid was isolated from diethylether from a reaction mixture of $V(Me_5Cp)_2$ and $PCl_3$ as described by Moran, M., Masaguer, J. R., Fernandez, V. Synthesis and characterization of halogen and pseudohalogen derivatives of substituted vanadocenes. J.Organometallic Chem. 291. 311–319, 1985. Yield. 20%. Anal Calcd. for $VC_{20}H_{30}Cl_2$: C, 61.2; H, 7.5; Cl, 13.0. Found: C, 59.9; H, 7.5; Cl, 13.1. UV-Vis $(CH_2Cl_2)$ $\lambda_{max}$: 740, 652 (d-d), 440 (LMCT of $Cp_2V^{2+}$), 270, 230 (π-π* of $Me_5Cp$-rings), nm. IR (Kbr Disc): 3118(s), 1194 (w), 1149(m), 1032(s), 959(w), 843(vs), 638(vs) $cm^{-1}$.

$V(Me_5Cp)OCl$, (Compound 25). This compound was prepared by following the procedure reported in Aistars, A., Newton, C., Rübensthal, T., Doherty, N. M. Covenient synthesis of dichloro(oxo)(pentamethylcyclopentadienyl)vanadium(V),(η-$C_5Me_5$)V(O)$Cl_2$. Organometallics. 16: 1994–1996, 1997. Sublimed green materials of $V(Me_5Cp)_2$ $Cl_2$ (24) was dissolved in dry THF and were subjected to purged with $O_2$ for 8 h. The solvent was removed under vacuum and recrystallized from hexane. Yield. 80%. Anal Calcd. for $VC_{10}H_{15}OCl_2$: C, 43.98; H, 5.54; Cl, 27.67. Found: C, 43.29; H, 5.62; Cl, 27.54. $^1$HNMR, $^{51}$V NMR: δ2.335 (5×$CH_3$). $(CH_2Cl_2)$ (UV-Vis $(CH_2Cl_2)$ $\lambda_{max}$: 680, 605 (LMCT of Oxygen and chloride ligand) 410 (LMCT of Cp to $V(O)^{2+}$), 290, 250 (π-π* of $Me_5Cp$-ring), nm. IR (Kbr Disc): 3440(b,m), 2962(m), 2906(s), 2858(m), 1621(w), 1487(m), 1437(s), 1375(vs), 1066(s), 1014(m), 960(m), 943 (m), 806(m), 744(m), 700(m) $cm^{-1}$.

In vitro Invasion Assays

The in vitro invasiveness of vanadocene-treated cancer cells was assayed using a previously published method which employs Matrigel-coated Costar 24-well transwell cell culture chambers ("Boyden chambers") with 8.0-μm-pore polycarbonate filter inserts. Narla R K, Liu X P, Klis D, Uckun F M. Inhibition of human glioblastoma cell adhesion and invasion by 4-(4'-hydroxylphenyl)-amino-6,7-dimethoxyquinazoline (WHI-P131) and4-(3'-bromo-4'-hydroxylphenyl)-amino-6,7-dimethoxyquinazoline (WHI-P154). Clin Cancer Res 4:2463–71, 1998. Albini, A., Iwamoto, Y., Kleinman, H. K., Martin, G. R., Aaronson, S. A., Kozlowski, J. M., and McEwan, R. N. A rapid in vitro assay for quantitating the invasiveness of tumor cells. Cancer Res. 47: 3239–3245, 1987. The chamber filters were coated with 50 μg/ml of Matrigel matrix, incubated overnight at room temperature under a laminar flow hood and stored at 4° C. On the day of the experiment, the coated inserts were rehydrated with 0.5 ml serum-free DMEM containing 0.1% bovine serum albumin for 1–2 hours. To study the effects of vanadocenes VDC and VDSe on invasiveness of cancer cells, exponentially growing cells were incubated with these vanadocenes at various concentrations ranging from 1 μM to 10 μM overnight. The cells were trypsinized, washed twice with serum-free DMEM containing BSA, counted and resuspended at $1\times10^5$ cells/ml. 0.5 ml cell suspension containing $5\times10^4$ cells in a serum-free DMEM containing vanadocene compounds or vehicle was added to the Matrigel-coated and rehydrated filter inserts. Next, 750 μl of NIH fibroblast conditioned medium was placed as a chemoattractant in 24-well plates and the inserts were placed in wells and incubated at 37° C. for 48 hr. After the incubation period, the filter inserts were removed, the medium was decanted off and the cells on the top side of the filter that did not migrate were scrapped off with a cotton tipped applicator. The invasive cells that migrated to the lower side of the filter were fixed, stained with Hema-3 solutions and counted under microscope. Five to 10 random fields per filter were counted to determine the mean (±SE) values for the invasive fraction. The invasive fractions of cells treated with quinazoline derivatives were compared to those of DMSO treated control cells and the percent inhibition of invasiveness was determined using the formula: % Inhibition=100×(1−Invasive Fraction of Drug-Treated Cells/Invasive Fraction of Control Cells). Each treatment condition was evaluated in duplicate in 3 independent experiments. IC50 values were calculated by non-linear regression analysis using an Graphpad Prism software version 2.0 (Graphpad Software, Inc., San Diego, Calif.).

Apoptosis Assays

A flow cytometric two-color terminal dideoxynucleotidyl transferase (TdT)-mediated digoxigenin-uridine triphosphate (dUTP) nick-end labeling assay (TUNEL) was employed to detect apoptotic nuclei. Gavrieli, Y., Sherman, Y., Ben-Sasson, S. A. Identification of programmed cell death in situ via specific labeling of nuclear DNA fragmentation. J. Cell Biol., 119: 493–501, 1992. Exponentially growing cells ($10^6$/ml) were incubated in DMSO alone (0.1%) or treated with 100 $\mu$M each of the 16 vanadocenes (VDB, VDC, VMDC, VDI, VDA, VDCN, VDOCN, VDSCN, VDSeCN, VDT, VDCO, VDFe, VD(acac), VDH, VD(dpy), and VD(dtc) in 0.1% DMSO for 24 h. Cells were washed in PBS, fixed in 4% paraformaldehyde in PBS for 15 min on ice. Following two washings in PBS, they were permeabilized with 0.1% Triton X-100 in 0.1% sodium citrate for 2 min on ice, and washed twice in PBS. Labeling of exposed 3'-hydroxyl (3'—OH) ends of fragmented nuclear DNA was performed using TdT and fluorescein isothiocyanate (FITC)-conjugated dUTP according to the manufacturer's recommendations (Boehringer Mannheim, Indianapolis, Ind.). Cells were counterstained with 5 $\mu$g/ml PI. Control samples included: (i) untreated cells; (ii) cells incubated with the reaction mixture without the TdT enzyme. Cells were analyzed with a FACS Calibur flow cytometer (Becton Dickinson, Mountain View, Calif.). Relative DNA content (PI) was detected with band-pass filter 585/42, and dUTP incorporation (FITC) was detected with band-pass filter 530/30. Fluorescence was compensated for in the acquisition software using single-label control samples. Data were acquired in listmode, gated to 10,000 events per sample, and analyzed with the use of CELLQuest software program (Becton Dickinson). Nonapoptotic cells do not incorporate significant amounts of dUTP due to lack of exposed 3'-OH ends, and consequently have relatively little or no fluorescence compared to apoptotic cells which have an abundance of 3'-OH (M2 gates). Vanadocene-induced apoptosis is shown by an increase in the number of cells staining with FITC-dUTP. The M1 and M2 gates were used to demarcate non-apoptotic and apoptotic PI-counterstained cell populations, respectively. TUNEL assays were performed using two testicular cell lines Tera-2 and Ntera-2 following exposure to each of the 16 vanadocenes. In other experiments, MC540 binding (as an early marker of apoptosis) and PI permeability (as a marker of advanced stage apoptosis) were simultaneously measured in human cancer cells 24 hours after exposure to vanadocenes, as previously described. Uckun, F. M., Narla, R. K., Jun, X., Zeren, T., Venkatachalam, T., Waddick, K. G., Rostostev, A., Myers, D. E. Cytotoxic activity of EGF-genstein against breast cancer cells. Clin. Cancer Res.4:901–912, 1998. Vassilev, A., Ozer, Z., Navara, C., Mahajan, S., and Uckun, F. M. Bruton's tyrosine kinase as an inhibitor of the Fas/CD95 death-inducing signaling complex. J. Biol. Chem. 274.1646–56, 1999. Whole cells were analyzed using a FACStar Plus flow cytometer (Becton Dickinson, San Jose, Calif.). All analyses were done using 488 nm excitation from an argon laser. MC540 and PI emissions were split with a 600 nm short pass dichroic mirror and a 575 nm band pass filter was placed in front of one photomultiplier tube to measure MC540 emission and a 635 nm band pass filter was used for PI emission.

Morphological evidence for apoptosis was sought among the TUNEL-positive cells using confocal laser scanning microscopy (CLSM). Confocal microscopy was performed using BioRad MRC-1024 Laser Scanning Confocal Microscope (BioRad, Hercules, Calif.) equipped with a krypton/argon mixed gas laser (excitation lines at 488, 568, and 647 nm) and mounted on a Nikon Eclipse E800 series upright microscope equipped with high numerical objectives. Using fluorescence imaging, the fluorescence emission of FITC and PI from nuclei of in Ntera-2 cells was simultaneously recorded using 598/40 nm, and 680 DF32 emission filter respectively. Confocal images were obtained using a Nikon 60×(NA 1.4) objective and Kalman collection filter. Digitized images were saved on a Jaz disk (Iomega Corp., Roy, Utah) and processed with the Adobe Photoshop software (Adobe Systems, Mountain View, Calif.). Final images were printed using a Fuji Pictography 3000 (Fuji Photo Film Co., Tokyo, Japan) color printer.

In other experiments, TERA-2 and NTREA-2 cells were plated at 50% confluency in T-150 flasks in media supplemented with 10% FCS; 24 h later, they were exposed to vehicle (0.05% DMSO) or 100 $\mu$M each of the 6 representative vanadocenes (VDC, VDO, VDSCN, VDSeCN, VDT, and VD(dtc) in 0.05% DMSO. Combined adherent and nonadherent cells ($5 \times 10^6$/sample) were harvested at 24 h and washed in PBS. DNA was prepared from Triton-X-100 lysates for analysis of fragmentation. Uckun, F. M., Evans, W. E., Forsyth, C. J., Waddick, K. G., Tuel-Ahlgren, L., Chelstrom, L. M., Burkhardt, A., Bolen, J., Myers, D. E. Biotherapy of B-cell precursor leukemia by targeting genistein to CD19associated tyrosine kinase. Science (Washington D.C.) 267:886–91, 1995. Uckun, F. M., Narla, R. K., Jun, X., Zeren, T., Venkatachalam, T., Waddick, K. G., Rostostev, A., Myers, D. E. Cytotoxic activity of EGF-genstein against breast cancer cells. Clin. Cancer Res. 4.901–912, 1998. In brief, cells were lysed in hypotonic 10 mmol/L Tris-HCl (pH 7.4), 1 mmol/L EDTA, 0.2% Triton-X-100 detergent; and subsequently centrifuged at 11,000 g. To detect apoptosis associated DNA fragmentation, supernatants were electrophoresced on a 1.2% agarose gel, and the DNA fragments were visualized by ultraviolet light after staining with ethidium bromide. In additional experiments, (a) leukemia cell lines NALM-6, MOLT-3, and HL-60, (b) glioblastoma cell lines U373 and U87, and (c) breast cancer cell lines MDA-MB-231 and BT-20 were exposed to multiple concentrations of VDC and VDSeCN and then assayed for apoptosis by DNA gels as well as flow cytometry.

In some experiments, immunofluorescence was used to examine the morphologic features of vanadocene-treated cancer cells. At the end of the indicated treatment period, cells were washed twice with PBS and fixed in 2% paraformaldehyde. The cells were permeabilized and nonspecific binding sites were blocked with 2.5% BSA in PBS containing 0.1% Triton X-100 for 30 min. Tubulin expression was examined by immunofluorescence using a monoclonal antibody against $\alpha$-tubulin (Sigma Chemical Co, St. Louis, Mo.) at a dilution of 1:1000 and an anti-mouse IgG conjugated to FITC. Cells were washed in PBS and counterstained with toto-3 (Molecular Probes Inc., Eugene, Oreg.) for 10 min at a dilution of 1:1000. Cells were washed again with PBS and the coverslips were mounted with Vectashield (Vector Labs, Burlingame, Calif.) and viewed with a confocal microscope (Bio-Rad $MRC_{1024}$) mounted in a Nikon Labhophot upright microscope. Digital images were saved on a Jaz disk and processed with Adobe Photoshop software (Adobe Systems, Mountain View, Calif.).

Oxovanadium
Cytotoxicity Assays

The cytotoxicity of oxovanadium (IV) complexes listed in Table 6 were tested against 9 different human cancer cell lines was performed using the MTT (3-[4,5-dimethylthiazol-2-yl]-2,5-diphenyl tetrazolium bromide) assay (Boehringer Mannheim Corp., Indianapolis, Ind.) as described previously (20). Briefly, exponentially growing tumor cells were seeded into a 96-well plate at a density of $4 \times 10^4$ cells/well and incubated with medium containing the oxovanadium (IV) compounds concentrations ranging from 0.1 to 250 $\mu M$ for 48 hours at 37° C. in a humidified 5% $CO_2$ atmosphere. Triplicate wells were used for each treatment. To each well, 10 $\mu l$ of MTT (0.5 mg/ml final concentration) was added and the plates were incubated at 37° C. for 4 hours to allow MTT to form formazan crystals by reacting with metabolically active cells. The formazan crystals were solubilized overnight at 37° C. in a solution containing 10% SDS in 0.01 M HCl. The absorbence of each well was measured in a microplate reader (Labsystems) at 540 nm and a reference wavelength of 690 nm. To translate the $OD_{540}$ values into the number of live cells in each well, the $OD_{540}$ values were compared to those on standard $OD_{540}$—versus—cell number curves generated for each cell line. The percent survival was calculated using the formula: % survival=Live cell number[test]/Live cell number [control]×100. The $IC_{50}$ values were calculated by non-linear regression analysis using an Graphpad Prism software version 2.0 (Graphpad Software, Inc., San Diego, Calif.).

In situ Detection of Apoptosis

The demonstration of apoptosis was performed as described earlier (20, 21) by thein situ nick-end-labeling method using in situ cell death detection kit (Boehringer Mannheim Corp., Indianapolis, Ind.) according to the manufacturer's recommendations. Exponentially growing cells were seeded in 6-well tissue culture plates and incubated with fresh medium containing compounds. After a 24 hour incubation at 37° C. in a humidified 5% $CO_2$ incubator the cells were collected into a 15 ml centrifuge tube, washed with PBS and pelleted by centrifugation at 1000 rpm for 5 min. The cells were fixed in 2% paraformaldehyde, washed with PBS and pelleted by centrifuging the tubes at 1000 rpm for 5 min. Cells pellets were resuspended in 50 $\mu l$ of PBS, transferred to superforst plus slides and allowed to attach for 15 min. The cells were permeabilized with 0.1% triton X-100 in 0.1% citrate buffer and incubated for 1 hr at 37° C. with the reaction mixture containing terminal deoxynucleotidyl transferase (TdT) and fluorescein isothiocyanate (FITC)-conjugated dUTP. Cells were washed with PBS to remove unbound reagents and the coverslips were mounted onto slides with Vectashield containing propidium iodide (Vector Labs, Burlingame, Calif.) and slides were viewed with a confocal laser scanning microscope. Non-apoptotic cells do not incorporate significant amounts of dUTP due to lack of exposed 3-hydroxyl ends, and consequently have much less fluorescence than apoptotic cells which have an abundance of exposed 3'-hydroxyl ends. In control reactions, the TdT enzyme was omitted from the reaction mixture.

Mitochondrial Transmembrane Potential Assessment

To measure the changes in mitochondria, NALM-6 cells were incubated with compound 29 at concentrations ranging from 0.1 $\mu M$ to 1 $\mu M$ for 24 hr, 48 hr, 72 hr or 96 hr, stained with specific fluorescent dyes and analyzed with flow cytometer. Mitochondrial membrane potential ($\Delta \Psi m$) was measured using two dyes including a lipophollic cation 5,5',6,6'-tetrachloro-1,1',3,3'-tetraethlybenzimidazolylcarbocyanine iodide (JC-1; Molecular probes, Eugene, Oreg.) and a cyanine dye, 1,1', 3,3,3',3'-hexamethylindodicarbocyanine iodide [$DiIC_1(5)$; Molecular probes] as earlier described (22). JC-1 can enter the cells, and selectively mitochondria, and has been used to assess $\Delta \Psi m$ in a variety of studies (23,24). JC-1 is a monomer at 527 nm after being excited at 490 nm; with polarization of $\Delta \Psi m$, J-aggregates are formed that shift emission to 590 nm (23, 24). This can be detected on a flow cytometer by assessing the green signal (at 527 nm) and green-orange signal (at 590 nm) simultaneously, creating an index of the number of cells polarized and depolarized mitochondria. The treated and control cells were washed and plated in a 6-well plate at $1 \times 10^6$ cells in fresh medium. JC-1 was added at a concentration of 10 $\mu g/ml$, and cells were incubated for 10 min in the dark at room temp. Cells were then washed twice with ice cold PBS and immediately analyzed using Becton Dickinson (San Jose, Calif.) Calibur flow cytometer. At least $2 \times 10^3$ cells were analyzed to determine the percentage of cells with polarized and depolarized mitochondria. $DiIC_1(5)$, a cyanine dye is amphioatheic and cationic that concentrate in energized mitochondria and has been used in a variety of studies to measure the mitochondrial membrane potential (25–27). NALM-6 cells were stained with $DiIC_1(5)$ at 40 nM concentration for 30 min in the dark as described for JC-1. The cells were analyzed using Vantage Becton Dickinson cell sorter equipped with HeNe laser with excitation at 635 nm and the fluorescence was collected at 666 nm.

Mitochondrial Mass Determination

Relative mitochondrial mass was measured by using Becton Dickinson Calibur flow cytometry and the fluorescent stain 10-n-nonyl-acridine orange (NAO), which binds the mitochondrial phospholipid cardiolipin, that has been extensively used to provide an index of mitochondrial mass (28). $1 \times 10^6$ compound 29-treated NALM-6 cells at concentrations of 0.1 $\mu M$ to 1 $\mu M$ for 24 hr, 48 hr, 72 hr, or 96 hr were incubated with 30 $\mu M$ of NAO in complete medium for 10 min at room temp in the dark, washed with ice-cold PBS and analyzed using log scale photomultiplier to detect the green fluorescence at 527 nm. Relative change in the mitochondrial mass was measured using the mean fluorescence value of mitochondria of compound 29-treated and vehicle-treated cells.

Quantitative Apoptosis Assays

A flow cytometric two-color terminal dideoxynucleotidyl transferase (TdT) mediated digoxigenin-uridine triphosphate (dUTP) nick-end labeling assay (TUNEL) was employed to detect apoptotic nuclei. Edelman, G. M. Adhesion and counteradhesion: morphogenetic functions of the cell surface. Prog. Brain Res. 101:1–14, 1994. Exponentially growing cells ($10^6$/ml) were incubated in DMSO alone (0.1%) or treated with 50 $\mu M$ each of the 15 oxovanadium compounds in 0.1% DMSO for 24 h. Cells were washed in PBS, fixed in 4% paraformaldehyde in PBS for 15 min on ice. Following two washings in PBS, they were permeabilized with 0.1% Triton X-100 in 0.1% sodium citrate for 2 min on ice, and washed twice in PBS. Labeling of exposed 3'-hydroxyl (3'-OH) ends of fragmented nuclear DNA was performed using TdT and fluorescein isothiocyanate (FITC)- conjugated dUTP according to the manufacturer's recommendations (Boehringer Mannheim, Indianapolis, Ind.). Cells were counterstained with 5 μg/ml PI. Control samples included: (i) untreated cells; (ii) cells incubated with the reaction mixture without the TdT enzyme. Cells were analyzed with a FACS Calibur flow cytometer (Becton Dickinson, Mountain View, Calif.). Relative DNA content (PI) was detected with band-pass filter 585/42, and dUTP incorporation (FITC) was detected with band-pass filter 530/30. Fluorescence was compensated for in the acquisition software using single-label control samples. Data were acquired in listmode, gated to 10,000 events per sample, and analyzed with the use of CELLQuest software program (Becton Dickinson). Nonapoptotic cells do not incorporate significant amounts of dUTP due to lack of exposed 3'-OH ends, and consequently have relatively little or no fluorescence compared to apoptotic cells which have an abundance of 3'-OH (M2 gates). Oxovanadium compounds-induced apoptosis is shown by an increase in the number of cells staining with FITC-dUTP. The M1 and M2 gates were used to demarcate non-apoptotic and apoptotic PI-counterstained cell populations, respectively.

Results

Vanadocene Compounds

Synthesis and Characterization of Vanadocene Compounds.

The chemical structures and physical data (viz., UV-vis spectral data, infrared spectral data, and elemental analysis results) of compounds 1–25 are detailed in Table 1, Table 2, Table 3, and Table 4.

Cytotoxic Effects of Vanadocenes on Human Testicular Cancer Cells

Using the mitochondrial function-based MTT viability assay, the effects of 5 metallocene dichlorides containing vanadium (VDC), titanium (TDC), zirconium (ZDC), molybdenum (MDC), or hafnium (HDC), on two human testicular cancer cell lines, Tera-2 and Ntera-2, were tested by measuring cellular proliferation at 7 different concentrations ranging from 1.9 μM to 250 μM for 24 h (FIG. 1). Only vanadium-containing metallocene, VDC, inhibited the growth of both cell lines with $IC_{50}$ values of 80.6 μM and 74.0 μM, respectively. Surprisingly, other metallocene dichlorides containing titanium, zirconium, molybdenum or hafnium as central metal atom (oxidation state IV), had no effect on cell proliferation even at 250 μM (Table 5). These results demonstrate that the vanadium(IV)-containing bis (cyclopentadienyl)-metal complex has cytotoxic activity against human testicular cancer cells.

Sixteen structurally similar compounds with differing substituents around the ancillary position of the $Cp_2$-vanadium(IV) unit were examined for their growth-inhibiting properties. These vanadocene complexes included: 4 vanadocene dihalides (VDB, VDC, VMDC, and VDI), 5 vanadocene di-pseudohalides (VDA, VDCN, VDOCN, VDSCN, and VDSeCN), 3 vanadocene disubstituted derivatives (VDT, VDCO, and VDFe), and 4 chelated vanadocenes (VD(acac), VDH, VD(bpy), and VD(atc)). The cytotoxic effects of these vanadocenes were tested at 7 different concentrations (1.9 μM to 250 μM). Each one of the 4 vanadocene dihalides, 5 vanadocene di-pseudohalides, 3 vanadocene disubstituted derivatives, and 4 chelated vanadocenes with various substituents covalently coordinated as ligands to the central metal ion vanadium (IV) induced a concentration-dependent cytotoxicity to both Tera-2 and Ntera-2 cells at micromolar concentrations. However, marked differences were noted in their potency.

The $IC_{50}$ values of VDB, VDC, VMDC, VDI, VDA, VDCN, VDOCN, VDSCN, VDSeCN, VDT, VDCO, VDFe, VD(acac), VDH, VD(BPY), and VD(DTC) calculated from concentration-response curves for the two cell lines are shown in Table 5 The $IC_{50}$ values for the 16 vanadocenes evaluated ranged from 9 to 221 μM. In general, vanadocenes were less potent than cisplatin ($IC_{50}$=~5 μM). However, the cytotoxic effects of the most potent vanadocenes, VDSCN and VDSeCN, were comparable to those of cisplatin ($IC_{50}$ values ~9–22 μM) when tested side-by-side under identical experimental conditions. The variable potency of vanadocenes suggest that the various mono and bidentate ligand groups affect the cytotoxic activity of these compounds. The potential cytotoxic effects of vanadium [vanadyl(IV) sulfate] were tested at the same concentrations. In sharp contrast to the organometallic compounds containing vanadium(IV), inorganic vanadium (oxidation state IV) salt lacked cytotoxic activity even at 250 μM (Table 5). Importantly, the anticancer activity of these compounds was not restricted to testicular cancer cells. Both compounds also killed human glioblastoma cells at low micromolar concentrations (Table 5).

Vanadocenes Induce Apoptosis in Human Testicular Cancer Cells

In order to determine if the cytotoxicity of vanadocenes is associated with apoptotic cell death, Tera-2 and Ntera-2 cells were cultured with vanadocenes (100 μM) for 24 h and then subjected to flow cytometric analysis for dUTP incorporation by the TdT-mediated TUNEL assay. FIGS. 2 and 3 depict the two-color flow cytometric contour plots of cells from representative TUNEL assays. Control Tera-2 and Ntera-2 cells were treated for 24 hours at 37° C. with 0.1% DMSO whereas test cells were treated for 24 hours at 37° C. with a vanadocene compound at 100 μM final concentration. The TdT-dependent incorporation of FITC-dUTP was dramatically increased in vanadocene-treated cells as a result of abundance of free 3'-hydroxyl DNA ends created by endonuclease-mediated DNA fragmentation. Among the 16 vanadocenes evaluated by the flow cytometric TUNEL assay, 15 caused a marked increase in TUNEL-positive nuclei ranging from 44.5% to 88% for Tera-2 cells and 38.7% to 99.6% for Ntera-2 cells respectively (Table 5).

Figure 4:
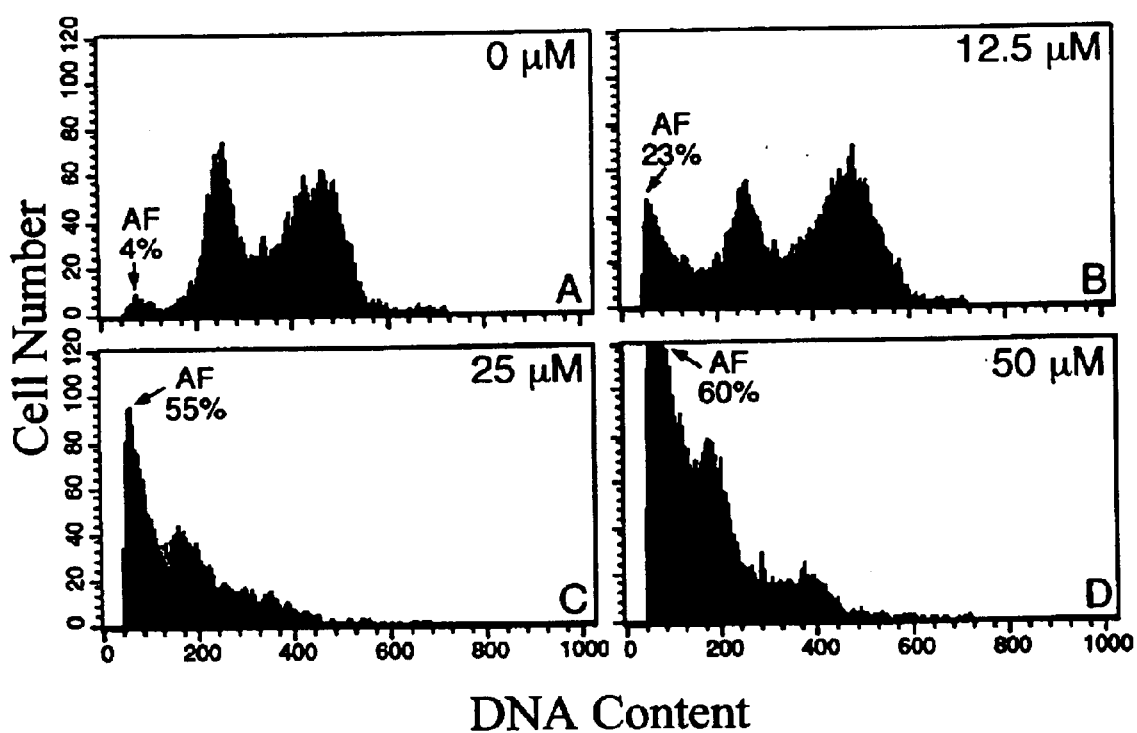
FIG. 4. Illustrates the formation of hyperdiploid nuclei and induction of apoptosis in vanadocene-treated Tera-2 testicular cancer cells. Cells were treated with vehicle, 12.5, 25, or 50 μM venadocene for 24 h, stained with propidium iodide and analysed by flow cytometry for DNA content. The percentages indicate the hyperdiploid/apoptotic nuclei.

FIGS. 2 and 3 also depict the two-color confocal microscopy images of DMSO treated control cells and vanadocene-treated test cells. Vanadocene-treated cells showed dual fluorescence, consistent with apoptosis. Furthermore, vanadocene-treated cells displayed the characteristic morphologic features of apoptotic cell death, including cellular shrinkage, chromatin condensation, and the appearance of typical apoptotic bodies. Apoptosis after vanadocene treatment was also evident from the concentration-dependent emergence of a hypodiploid (<2N) peak in the DNA histograms of PI-stained cells, which was accompanied by nonselective loss of G0/1, S, and G2M phase cells (FIG. 4).

Figure 5:
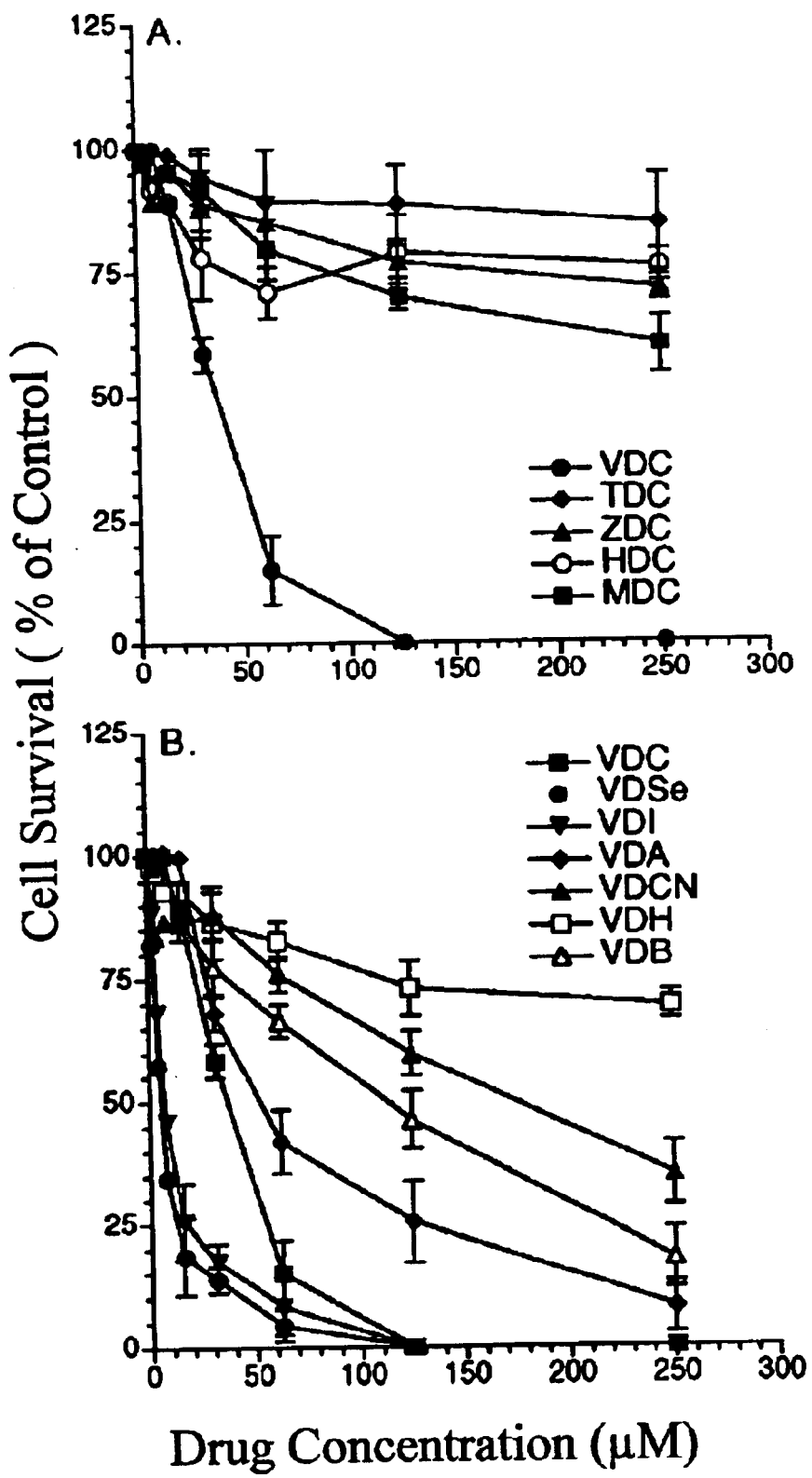
FIG. 5 Illustrates Cytotoxic activity of metallocene dichlorides (A) and vanadocene (B) on human glioblastoma cells. U373 glioblastoma cells were incubated with increasing concentrations of 5 metallocene dichlorides VDC, TDC, ZDC, HDC, and MDCT or 7 representative vanadocene VDC, VDSeCN, VDI, VDA, VDCN, VDH, and VDB for 24 hr in 96-well plates and the cell survival was determined by the MTT assay as described in materials and methods. Activity is expressed relative to DMSO controls. The data points represent the mean (±SD) value of three independent experiments.

Cytotoxic Activity of Vanadocene Compounds Against Human Glioblastoma, Leukemia, and Breast Cancer Cell Lines In MTT assays, both U373 glioblastoma cells (Table 5 and FIG. 5) and NALM-6 B-lineage acute lymphoblastic leukemia (ALL) cells (Table 5) were found to be sensitive to the cytotoxic activity of vanadocenes. Similar to testicular cancer cells, glioblastoma cells were sensitive to VDC but not to other metallocene dichlorides (Table 5). Interestingly, VDI and VD(dtc) were >1-log more active against U373 cells than they were against TERA-2 or NTERA-2 cells. VDSeCN which was the most active vanadocene compound against testicular cancer cells was found to be the most active vanadocene compound against glioblastoma cells as well (Table 5, FIG. 5). Only 4 vanadocenes (VDC, VDB, VDI, VDA, VDSeCN) were tested against NALM-6 leukemia cells and all 4 were active and VDSeCN was the most potent (Table 5).

Figure 6:
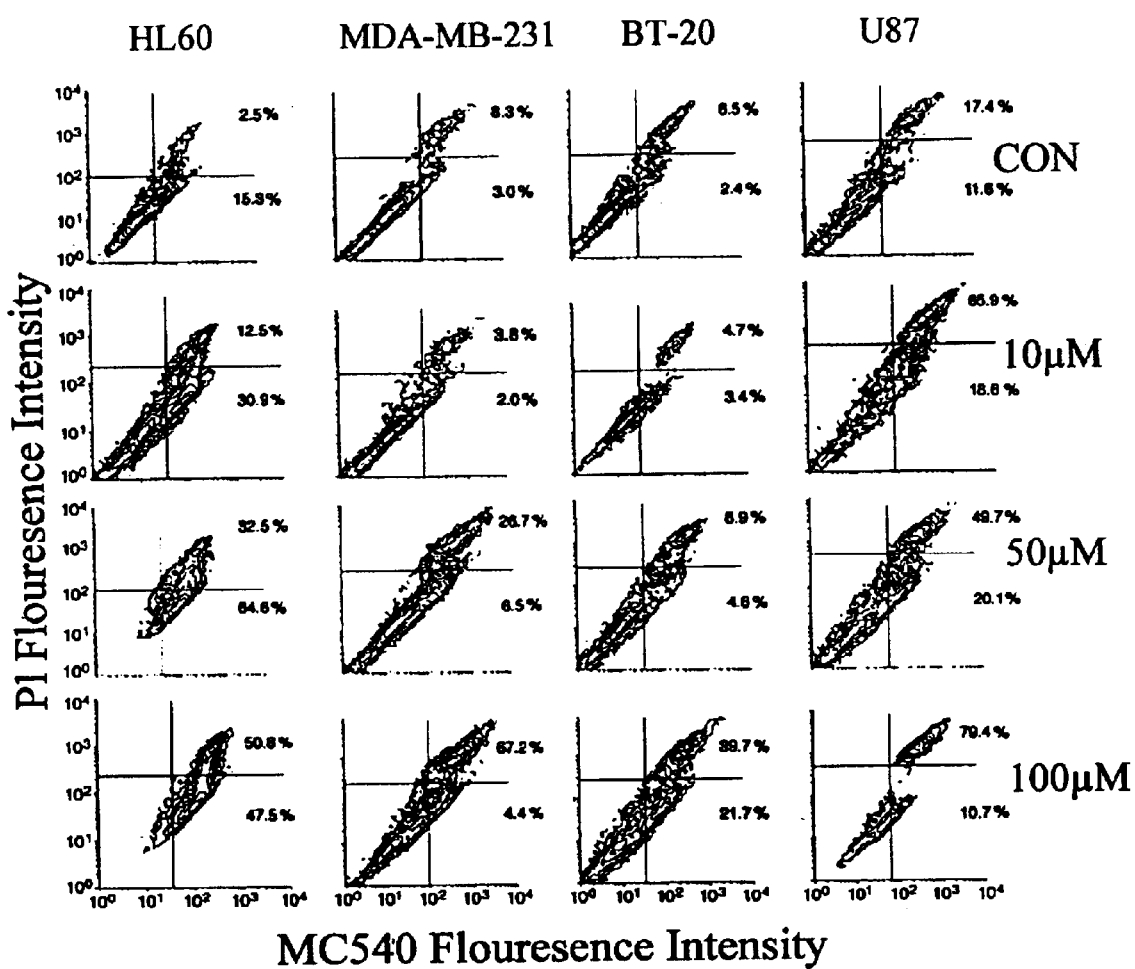
FIG. 6. Illustrates the cytotoxic activity of VDSeCN in 4 human cancer cell lines. Fluorescence-activated cell sorter-correlated two parameter display (fluorescence from propidium iodide [PI], and fluorescence from MC540 staining) of AML(HL-60), breast cancer (MDA-MB-231 and BT-20) and brain tumor (U87) cells stained with MC540 and PI 24 h after treatment with vehicle (CON), 10, 50, or 100 μM of VDSeCN. The percentages indicate the fraction of cells at an early stage of apoptosis, as measured by single MC540 fluorescence, and the fraction of cells at an advanced stage apoptosis, as measured by dual MC540/PI fluorescence.
Figure 7:
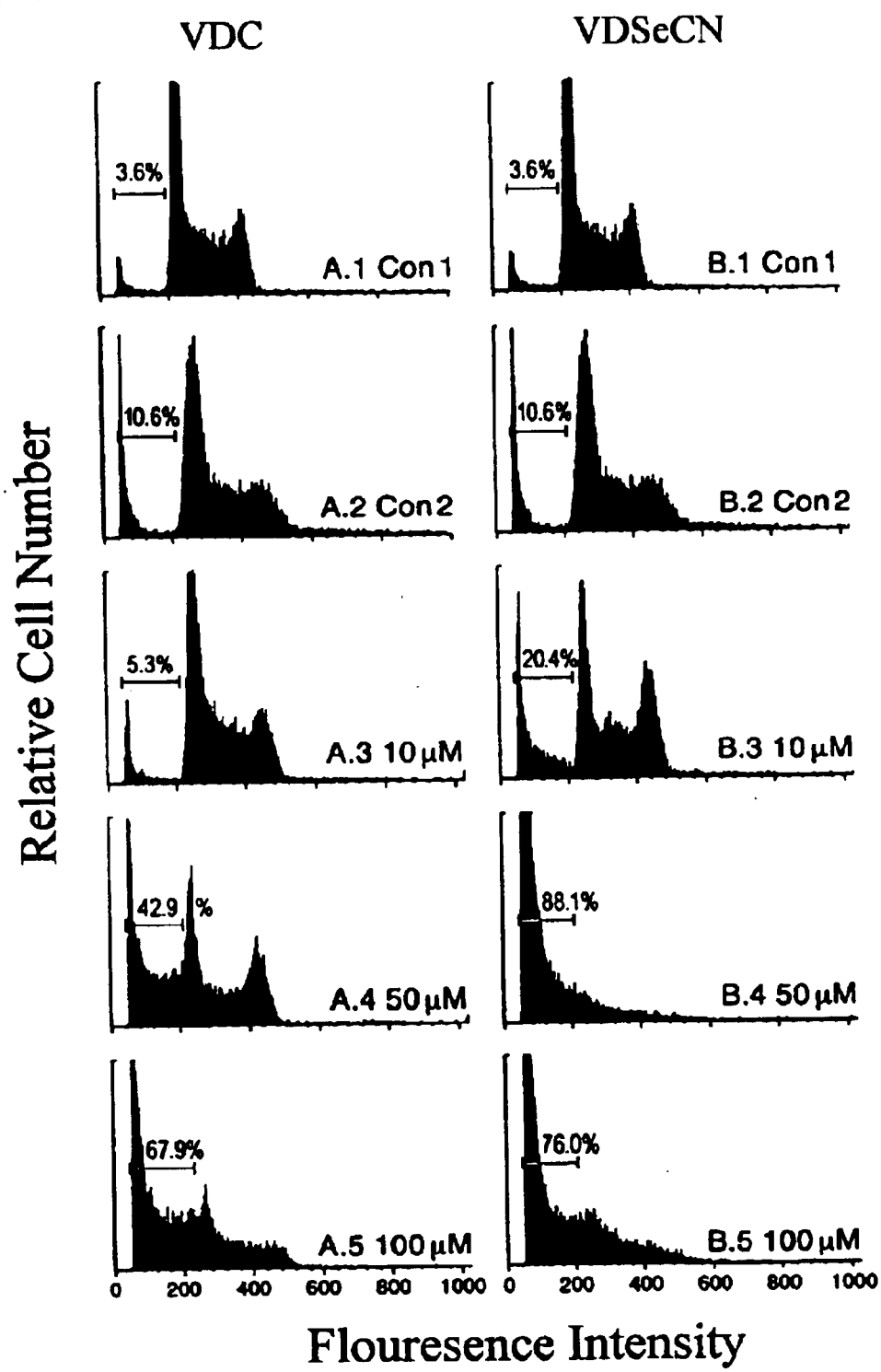
FIG. 7. Illustrates the formation of hyperdiploid nuclei and induction of apoptosis in vanadocene-treated AML HL-60 cells. Cells were treated with vehicle (Con 1 and Con 2), 10, 50 and 100 μM VDC or VDSeCN for 24 h, stained with propidium iodide and analysed by flow cytometry for DNA content. The percentages indicate the hyperdiploid/apoptotic nuclei.

To determine whether the cytotoxicity of vanadocenes against non-testicular cancer cells was also associated with apoptosis, MC540 binding (as an early marker of apoptosis) and PI permeability (as a marker of advanced stage apoptosis) were simultaneously measured in HL60 acute myeloid leukemia (AML), MDA-MB231 and BT-20 breast cancer, as well as U87 glioblastoma cells 24 hours after exposure to the lead vanadocene compound VDSeCN. As shown in FIG. 6, VDSeCN induced apoptosis in all 4 cell lines in a concentration-dependent fashion. At 100 $\mu$M, 51% of HL-60 cells, 67% of MDA-MB-231 cells, 40% of BT-20 cells, and 79% of U87 cells showed dual MC540PI fluorescence consistent with advanced stage apoptosis. The total percentage of apoptotic cells (both early MC540$^+$PI$^-$ and advanced stage MC540$^+$PI$^+$) at this concentration were 98% for HL-60 cells, 72% for MDA-MB-231 cells, 61% for BT-20 cells, and 90% for U87 cells (FIG. 6). Apoptosis after both VDSeCN and VDC treatment was also evident from the concentration-dependent emergence of a hypodiploid (<2N) peak in the DNA histograms of PI-stained HL-60 leukemia cells, which was accompanied by nonselective loss of G0/1, S, and G2M phase cells (FIG. 7).

Figure 8:
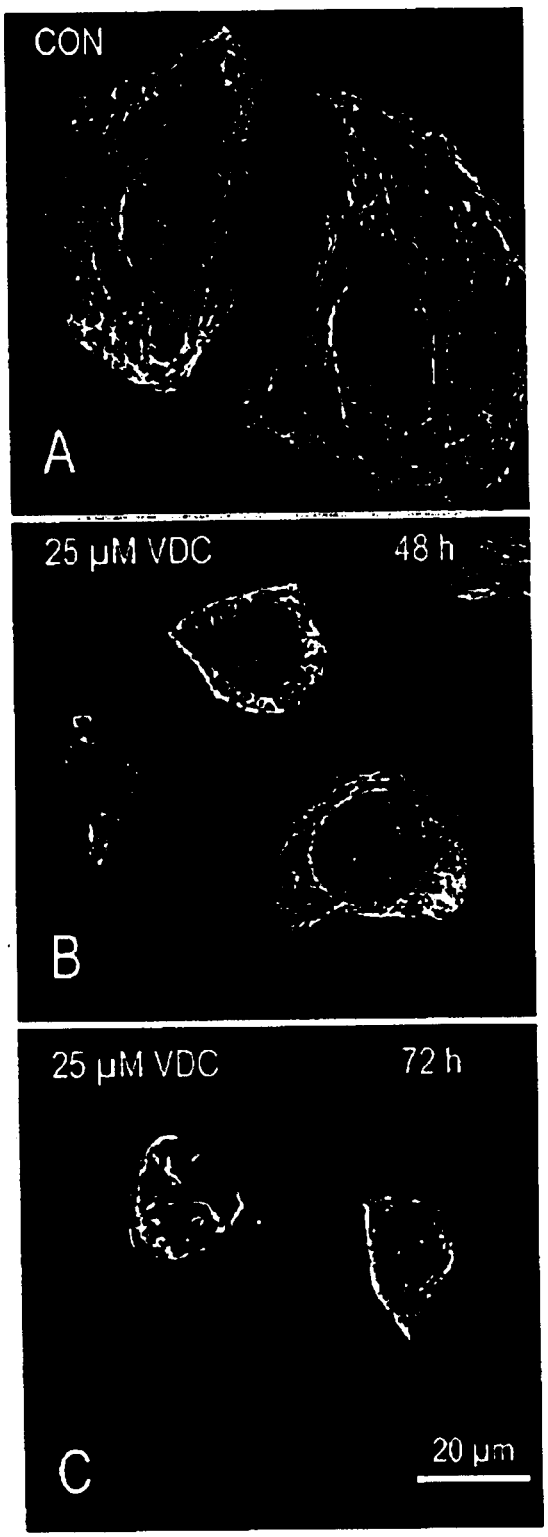
FIG. 8. Illustrates the morphological features of breast cancer BT-20 cells treated with VDC. cells were incubated with vehicle (A), or 25 μM of VDC for 48 hr (B) or 72 hr (C) 24 hr and processed for immunofluorescence using a monoclonal antibody to α-tubulin (green fluorescence). VDC-treated cells showed marked shrinkage with disruption of microtubules and lost their ability to adhere to the substratum. Blue fluorescence represents nuclei stained with TOTO-3.

Immunofluorescence staining with anti-$\alpha$-tubulin antibody and the nuclear dye toto-3 in combination with confocal laser scanning microscopy was performed to examine the morphological features of BT-20 breast cancer cells treated with VDC. After 48–72 hr of exposure to 25 $\mu$M VDC, most of the BT-20 cells showed an abnormal architecture with complete disruption of microtubules, marked shrinkage, nuclear fragmentation and inability to adhere to the substratum (FIG. 8). The cytotoxic effects of metallocene compounds were systematically assessed, including 16 vanadocene diacido complexes against human testicular cancer cells. Vanadoces exhibited significant cytotoxicity against testicular cancer cells and induced apoptosis within 24 hours. Vanadocenes with dithiocyanate (VDSCN) and diselenocyanate (VDSeCN) as ancillary ligands were identified as the most potent cytotoxic compounds. Vanadocenes were capable of inducing apoptosis not only in testicular cancer cells, but in ALL, AML, breast cancer, and glioblastoma cells as well. Thus, the potent cytotoxic activity of vanadocene compounds was not limited to testicular cancer cells. The lead compound VDSeCN may be useful as an anti-cancer agent.

Among the five metallocenes evaluated, only vanadium (IV)-containing complexes exhibit cytotoxicity against human testicular cancer cells. Biological evaluation of a novel series of systematically coordinated vanadocenes with dihalide, pseudodihalide, disubstituted derivatives, and chelated ancillary ligands demonstrated that the cytotoxic potency of vanadocenes can be modulated by the coordinated ligands. All 16 vanadocenes tested side-by-side induced apoptosis of testicular cancer cells as shown by increased dUTP incorporation into nuclear DNA. Confocal microscopy images confirmed the results of dUTP incorporation in the nuclei of representative vanadocene-treated cells. In contrast, the inorganic vanadium(IV) compound, vanadyl sulfate, had no cytotoxic effects on testicular cancer cells. Thus, although the cytotoxic effect of vanadocenes was primarily dependent upon the central vanadium(IV) ion, the two cyclopentadienyl units attached to vanadium(IV) coordination sites, and the various mono and bidentated ligand groups coordinated to the bis(cyclopentadienyl) vanadium (IV) moiety appear to be also very important for their anticancer activity.

Metallocene diacido complexes, especially titanocene dichloride and vanadocene dichloride may be useful as a chemopreventive agent and has been found to be active against development of mammary, lung, colon, skin, as well as against various human tumors heterotransplanted to athymic mice. Köpf-Maier, P., Kopf, H. Tumor inhibition by titanocene complexes: activity against B16 melanoma and colon 38 carcinoma. Arzneim-Forsch/Drug Res., 37: 532–534, 1987. Moebus, V. J., Stein, R., Kieback, D. G., Runnebaum, I. B., Sass, G., Kreienberg, R. Antitumor activity of new organometallic compounds in human ovarian cancer cell lines and comparison to platin derivatives. Anticancer Res., 17. 815–822, 1997. Surprisingly, unlike vanadocenes, TDC as well as other non-vanadium(IV)-containing metallocenes had no effect on the growth of testicular cancer cells. Therefore, it is likely that the mechanism of vanadocene-mediated growth inhibition is different from that induced by titanocene or other metallocenes reported in other types of cancer cells. Köpf-Maier, P., Kopf, H. Tumor inhibition by titanocene complexes: activity against B16 melanoma and colon 38 carcinoma. Arzneim-Forsch/Drug Res., 37: 532–534, 1987. Köpf-Maier, P. Tumor inhibition by titanocene complexes: influence upon two xenografted human lung carcinomas. J. Cancer Res. Clin. Oncol., 113: 342–348, 1987. McLauglin, M. L., Cronan, J. M., Schaller, T. R., Snelling, R. D. DNA-metal binding by antitumor-active metallocene dichlorides from inductively coupled plasma spectroscopy analysis: Titanocene dichloride forms DNA-Cp$_2$Ti or DNA-CpTi adducts depending on pH. J. Am. Chem. Soc., 112. 8949–8952, 1990. This difference observed between TDC and VDC is most likely due to structural orientation as well as the one electron configuration of TDC when compared to vanadocenes such as VDC. In addition, unlike other transition metals, vanadium(IV)-containing metallocenes can have pleiotropic effects in cells such as modulation of the cellular redox potential, Rehder, D. The bioinorganic chemistry of vanadium. Angew Chem. Int. Ed. Engl., 30:148–167, 1991, and Choukroun, R., Douziech, B., Pan, C., Dahan, F., Cassoux, P. Redox properties of cationic vanadium(IV):[Cp$_2$VCH$_3$ (CH$_3$CN)][BPh$_4$]. Oraganoinetallics, 14: 4471–4473, 1995, increased phosphorylation, Heffetz, D., Bushkin, I., Dror, R., Zick, Y. The insulinomimetic agents H$_2$O2 and vanadate stimulate protein tyrosine phosphorylation in intact cells. J. Biol. Chem., 265: 2896–2902, 1990. Stern, A., Yin, X., Tsang, S. S., Davison, A., Moon, J. Vanadium as a modulator of cellular regulatory cascades and oncogene expression. Biochem. Cell Biol., 71. 103–112, 1993, and generation of reactive oxygen intermediates. Byczkowski, J. Z., Wan, J. Z., Kulkarni, A. P. Vanadium-mediated lipid peroxidation in microsomes from human term placenta. Bull. Environ. Contain. Toxicol., 41: 696–703, 1988. Ozawa, T., Hanaki, A. ESR evidence for the formation of hydroxyl radicals during the reaction of vanadyl ions with hydrogen peroxide. Chem. Pharm. Bull., 37: 1407–1409, 1989. Carmichael, A. J. Vanadyl-induced Fenton like reaction in RNA: an ESR and spin trapping study. FEBS Lett., 261: 165–170, 1990. Younes, M., Strubelt, O. Vanadate-induced toxicity towards isolated perfused rat livers: The role of lipid peroxidation. Toxicology, 66: 63–74, 1991. Keller, J., Sharma, R. P., Grover, T. A., Piette, L. H. Vanadium and lipid peroxidation: Evidence of involvement of vanadyl and hydroxyl radical. Arch. Biochem. Biophys. 265. 524–533, 1988. Sakurai, H., Nakai, M., Miki, T., Tsuchiya, K., Takada, J., Matsushita, R. DNA cleavage by hydroxyl radicals generated in a vanadyl ion-hydrogen peroxide system. Biochem. Biophys. Res.

Commun. 189: 1090–1095, 1992. Sakurai, H., Tamura, H., Okatani, K. Mechanism for a new antitumor vanadium complex hydroxyl radical-dependent DNA-cleavage by 1,10-phenanthroline-vanadyl complex in the presence of hydrogen peroxide. Biochem. Biophys. Res. Commun., 206:133–137, 1995. Shi, X., Wang, P., Jiang, H., Mao, Y., Ahmed, N., Dalal, N. Vanadium(IV) causes 2'-deoxyguanosine hydroxylation and deoxyribonucleic acid damage via free radical reactions. Ann. Clin. Lab. Sci. 26:39–49, 1996.

The potential therapeutic applications of organovanadium compounds including vanadocenes in vivo, particularly to suppress tumor cell growth via apoptosis, reduce hyperlipidemia, and hypertension via tyrosine kinase-signalling pathways with relatively few adverse effects has sparked interest as a new class of pharmacological agents. Eliopoulos, A. G., Kerr, D. J., Maurer, H. R., Hilgard, P., Spandidos, D. A. Induction of the myc but not CH-ras promoter by platinum compounds. Biochem. Pharmacol. 50:33–38, 1995. Orvig, C., Thompson, K. H., Battel, M., McNeill, J. H. Vanadium compounds as insulin mimetics. In: Sigel H, Sigel A, eds. Metal ions in biological systems New York:Marcel Dekker 31: 595–616, 1995. Tsiani, E., Fantus, I. G. Vanadium compounds: biological actions and potential as pharmacological agents. Trends Endocrinol. Metab. 8: 51–58, 1997. Nechay, B. R. Mechanisms of action of vanadium. Annu. Rev. Pharmacol. Toxicol. 24:501–524, 1984. The apoptosis-inducing cytotoxic effects of novel vanadocenes against human cancer cells reported herein indicate that vanadocenes may be useful as anticancer agents.

TABLE 1

Vanadocene Compounds - Type 1 Series

| # | Compound | Chemical Structure | UV-vis [λ (nm); Solvent] | IR Spectral Data [cm$^{-1}$] | Elemental Analysais [Found (Calcd.)] |
|---|---|---|---|---|---|
| 1 | HDC | 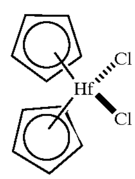 | 312, 268, 232 (CH$_2$Cl$_2$) | 3105(vs), 1439(vs), 1365(m), 1126(m), 1014(vs), 920(s,d), 802(vs), 816(vs), 611(m) | C, 32.09 (31.62) H, 2.75 (2.63) Cl, 18.98 (18.71) |
| 2 | MDC | 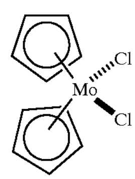 | 678, 436, 299, 283, 267 (DMSO) | 3093(vs), 1420(vs), 1375(m), 1100(m), 1060(m), 825(vs), 590(m) | C, 40.8 (40.4) H, 3.39 (3.37) Cl, 24.4 (23.9) |
| 3 | TDC | 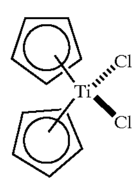 | 526, 391, 314, 255 (CH$_2$Cl$_2$) | 3105(vs), 1441(vs), 1368(m), 1130(m), 1016(vs), 956(m), 872(s), 820(s) | C, 48.56 (48.2) H, 4.03(4.01) Cl, 28.78 (28.5) |
| 4 | ZDC | 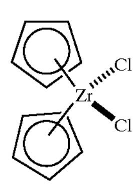 | 341, 294, 236 (CH$_2$Cl$_2$) | 3104(vs), 1435(s), 1363(m), 1122(s), 1014(s), 815(s), 610(m) | C, 41.01 (41.09) H, 3.4 (3.4) Cl, 24.84 (24.31) |
| 5 | VDC | 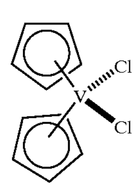 | 767, 647, 380, 283, 244 (CH$_2$Cl$_2$) | 3095(vs), 1444(s), 1433(s), 1130(m), 1070(m), 887(m), 825(vs) | C, 47.88 (47.62) H, 4.04 (3.97) Cl, 27.64 (28.1) |

TABLE 2

Vanadocene Compounds - Type 2 Series

| # | Compound | Chemical Structure | UV-vis [λ (nm); Solvent] | IR Spectral Data [cm⁻¹] | Elemental Analysis [Found (Calcd.)] |
|---|---|---|---|---|---|
| 6 | VDB | Cp₂V(Br)₂ | 733, 412, 298, 232 (CH₂Cl₂) | 3089(vs), 1425(s), 1431(m), 1373(m), 1363(w), 1128(w), 1024(m), 1014(m), 825(vs) | C, 35.19 (35.19) H, 2.9 (2.92) Br, 46.91 (46.92) |
| 7 | VDI | Cp₂V(I)₂ | 620, 552, 352, 296, 232 (CH₂Cl₂) | 3095(s), 1425(s), 1373(m), 1182(m), 1024(m), 1014(m), 825(vs) | C, 28.1 (27.58) H, 2.42 (2.3) I, 58.4 (58.9) |
| 8 | VDA | Cp₂V(N₃)₂ | 434, 314, 257, 233 (CH₂Cl₂) | 3114(vs), 1448(m), 1375(m), 1126(w), 1080(s), 1024(m), 835(vs), 590(m) | C, 45.28 (45.28) H, 3.73 (3.77) N, 31.16 (31.2) |
| 9 | VDN | Cp₂V(CN)₂ | 605, 394, 307, 250 (CH₂Cl₂) | 3114(vs), 2120(s), 2110(s), 1435(s), 1420(s), 1126(m), 1014(s), 881(s), 848(s), 845(s) | C, 60.98 (61.89) H, 4.30 (4.29) N, 11.45 (12.00) |
| 10 | VDO | Cp₂V(OCN)₂ | 742, 373, 277, 237 (CH₂Cl₂) | 3531(m), 3110(m), 2248(vs), 2217(vs), 1444(s), 1330(s), 1024(w), 833(vs), 603(s), 593(s) | C, 53.85 (54.3) H, 3.97 (3.8) N, 10.2 (10.6) |
| 11 | VDOCN | Cp₂V(OCN)(Cl) | 710, 490, 257, 227 (CH₂Cl₂) | 3110(m), 2657(w), 2117(vs), 1444(m), 1330(s), 1261(w), 1018(m), 950(m), 833(vs), 635(vs), 424(w) | C, 51.35 (51.06) H, 3.97 (3.87) N, 5.65 (5.41) Cl, 13.45 (13.73) |
| 12 | VDS | Cp₂V(SCN)₂ | 739, 463, 401, 270, 251 (CH₂Cl₂) | 3087(s), 2086(vs), 2067(vs), 1433(s), 1423(m), 1010(m), 840(vs), 480(vw) | C, 47.55 (47.05) H, 3.26 (3.59) S, 20.91 (20.91) |
| 13 | VDSe | Cp₂V(SeCN)₂ | 716, 488, 456, 270, 251 (CH₂Cl₂) | 3076(s), 2085(vs), 2065(vs), 1444(m), 1431(s), 1074(w), 1008(m), 962(m), 843(vs) | C, 36.85 (36.83) H, 2.64 (2.56) N, 6.97 (7.1) |

TABLE 2-continued

Vanadocene Compounds - Type 2 Series

| # | Compound | Chemical Structure | UV-vis [λ (nm); Solvent] | IR Spectral Data [cm⁻¹] | Elemental Analysis [Found (Calcd.)] |
|---|---|---|---|---|---|
| 14 | VDFe | (Cp)₂V(NCCH₃)(Cl) [FeCl₄] | 648, 575, 362, 311, 265, 240 (CH₂Cl₂) | 3109(m), 2924(m), 2318(s), 2289(m), 1622(m), 1447(s), 1435(m), 1358(w), 1027(s), 1012(s), 856(s), 846(s) | C, 31.2 (31.6) H, 2.56 (2.9) N, 3.48 (3.1) Cl, 40.31 (39.98) |
| 15 | VDT | (Cp)₂V(OTf)₂ | 740, 640, 370, 309, 270, 230 (CH₂Cl₂) | 3118(s), 1564(vs), 1440(s), 1350(s), 1218(s), 1194(w), 1149(vs), 1032(s), 959(w), 843(vs), 638(vs) | C, 44.81 (44.45) H, 3.99 (3.96) S, 7.52 (7.46) |

TABLE 3

Vanadocene Compounds - Type 3 Series

| # | Compound | Chemical Structure | UV-vis (λ(nm); Solvent] | IR Spectral Data [cm⁻¹] | Elemental Analysis [Found (Calcd.)] |
|---|---|---|---|---|---|
| 16 | VD(acac) | 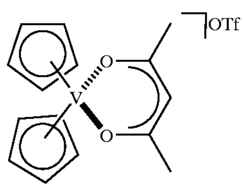 | 740, 640, 370, 309, 270, 230 (CH₂Cl₂) | 3118(s), 2295(w), 1564(vs), 1440(s), 1350(s), 1267(sb), 1218(s), 1194(w), 1149(vs), 1032(s), 983(w), 910(w), 843(s), 573(s) | C, 44.81 (44.45) H, 3.99 (3.96) S, 7.52 (7.46) |
| 17 | VD(h$_f$-acac) | 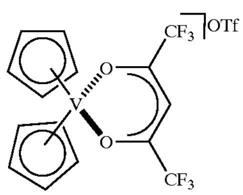 | 575, 377, 314, 271, 244 (CH₂Cl₂) | 3117(m), 1637(vs), 1597(w), 1552(w), 1446(s), 1260(vs), 1219(vs), 1163(vs), 1142(s), 1120(m), 1030(vs), 851(s), 640(vs) | C, 35.76 (35.89) H, 2.08 (2.06) S, 5.89 (5.98) |
| 18 | VD(bpy) | 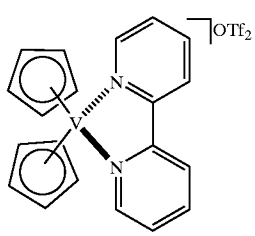 | 780, 326, 272, 241 (CH₂Cl₂) | 3135(m), 3099(s), 1605(s), 1504(m), 1477(m), 1452(s), 1437(vs), 1307(m), 1257(vs), 1232(vs), 1028(vs), 862(vs), 771(vs), 636(vs) | C, 52.48 (53.1) H, 3.72(3.69) N, 2.51 (2.58) S, 5.73 (5.9) |
| 19 | VD(cat) | 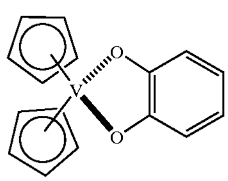 | 711, 438, 337, 292, 275, 259 (CH₂Cl₂) | 3100(w), 3080(w), 2951(m), 2945(w), 2860(w), 1468(s), 1438(m), 1404(m), 1359(w), 1261(vs), 1012(w), 804(vs), 638(w). | C, 66.79 (66.45) H, 4.93 (4.88) |

TABLE 3-continued

Vanadocene Compounds - Type 3 Series

| # | Compound | Chemical Structure | UV-vis [λ(nm); Solvent] | IR Spectral Data [cm⁻¹] | Elemental Analysais [Found (Calcd.)] |
|---|---|---|---|---|---|
| 20 | VD(dtc) | (structure with Cp₂V, S-C(=N(CH₂CH₃)₂)-S, OTf) | 621, 535, 392, 330, 276, 270, 230 (CH₃CN) | 3107(m), 1632(s), 1595(w), 1538(w), 1439(s), 1212(s), 1201(s), 1156(s), 1123(m), 1019(s), 855(s), 641(s) | C, 43.41 (43.31) H, 4.14 (4.18) N, 2.86 (2.93) S, 19.98 (20.08) |
| 21 | VDPH | (structure with Cp₂V, O-C(Ph)=N-Ph, OTf) | 680, 501, 377, 314, 261, 233 (CH₂Cl₂) | 3117(s), 1600(m), 1539(s), 1495(m), 1450(m), 1300(m), 1281(s), 1244(s), 1173(s), 999(m), 758(m), 694(m), 638(s) | C, 36.85 (36.83) H, 2.64 (2.56) N, 6.97 (7.1) |
| 22 | VDH | (structure with Cp₂V, O-C(CH₃)=N-H, OTf) | 710, 550, 401, 300, 261, 233 (CH₂Cl₂) | 1695(mb), 1635(m), 1500(vs), 1450(s), 1280(s), 1260(s), 1215(vs) 1144(s), 959(m), 758(m), 635(m), 540(w), 480(m) | C, 38.12 (38.61) H, 3.72 (3.46) N, 3.26 (3.46) |

TABLE 4

Vanadocene Compounds - Type 4 Series

| # | Compound | Chemical Structure | UV-vis [λ(nm); Solvent] | IR Spectral Data [cm⁻¹] | Elemental Analysais [Found (Calcd.)] |
|---|---|---|---|---|---|
| 23 | VMDC | (bis(methylcyclopentadienyl)VCl₂) | 760, 659, 383, 286, 233 (CH₂Cl₂) | 3135(m), 3099(s), 1307(m), 1028(s), 862(s), 771(s), 636(s) | C, 49.92 (49.82) H, 4.90 (5.19) Cl, 24.90 (24.60) |
| 24 | VPMDC | (bis(pentamethylcyclopentadienyl)VCl₂) | 740, 652, 440 (CHCl₃) | 3118(s), 1194(w), 1149(m), 1032(s), 959(w), 843(vs), 638(vs) | C, 59.9 (61.2) H, 7.5 (7.6) Cl, 13.1 (13.0) |

TABLE 4-continued

Vanadocene Compounds - Type 4 Series

| # | Compound | Chemical Structure | UV-vis [λ(nm); Solvent] | IR Spectral Data [cm$^{-1}$] | Elemental Analysis [Found (Calcd.)] |
|---|----------|-------------------|------------------------|-------------------------------|--------------------------------------|
| 25 | VPMOC | 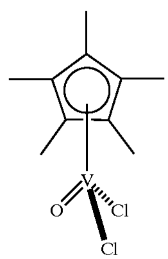 | 680, 605, 290, 250 (CHCl$_3$) | 2962(m), 2906(s), 2858(m), 1621(w), 1497(m), 1437(s), 1375(vs), 1066(s), 1014(m), 960(m), 943(m), 806(m), 744(m), 700(m) | C, 43.29 (43.98) H, 5.62 (55.4) Cl, 27.54 (27.67) |

TABLE 5

In Vitro Cytotoxic Activity of Vanadocene Compounds Against Human Cancer Cells.

| Compound | IC$_{50}$ [MTT]($\mu$M) | | | | % Apoptosis at 100 $\mu$M | |
|----------|------|--------|------|--------|------|--------|
| | TERA-2 | NTERA-2 | U373 | NALM-6 | TERA-2 | NTERA-2 |
| Metallocene Dichlorides | | | | | | |
| HDC | >250 | >250 | >250 | N.D. | N.D. | N.D. |
| MDC | >250 | >250 | >250 | N.D. | N.D. | N.D. |
| TDC | >250 | >250 | >250 | N.D. | N.D. | N.D. |
| ZDC | >250 | >250 | >250 | N.D. | N.D. | N.D. |
| VDC | 81 | 74 | 42 | 19 | 88 (87, 89) | 35 (34, 34) |
| Vanadocene Diacido Compounds | | | | | | |
| VDB | 154 | 70 | 62 | 17 | 84 (83, 86) | 93 (93, 94) |
| VDI | 221 | 204 | 5 | 18 | 72 (71, 73) | 57 (46, 69) |
| VDA | 70 | 68 | 51 | 16 | 85 (78, 92) | 85 (78, 93) |
| VDCO | 50 | 90 | N.D. | N.D. | 73 (67, 78) | 98 (97, 99) |
| VDCN | 51 | 93 | 53 | N.D. | 80 (78, 82) | 97 (96, 97) |
| VDOCN | 31 | 63 | N.D. | N.D. | 85 (80, 90) | 95 (94, 96) |
| VDSCN | 23 | 17 | 19 | N.D. | 64 (58, 69) | 53 (46, 60) |
| VDSeCN | 9 | 22 | 2 | 3 | 78 (75, 80) | 99.6 ± 0.2 (N = 4) |
| VDFe | 100 | 113 | N.D. | N.D. | 85 (84, 87) | 87 (81, 94) |
| VDT | 76 | 137 | N.D. | N.D. | 71 (71, 71) | 55 ± 26 (N = 4) |
| Vanadocene Chelated Compounds | | | | | | |
| VD(acac) | 64 | 75 | N.D. | N.D. | 72 ± 17 | 48 ± 13 (N = 3) |
| VD(bpy) | 37 | 53 | N.D. | N.D. | N.D. | 78 (77, 78) |
| VD(dtc) | 60 | 83 | 7 | N.D. | 83 (82, 84) | 67 ± 13 (N = 3) |
| VD(cat) | 79 | 93 | N.D. | N.D. | N.D. | 12 (9, 15) |
| VDPH | >250 | 61 | N.D. | N.D. | 88 ± 3 (N = 3) | 90 ± 3 (N = 4) |
| VDH | 118 | 125 | >250 | N.D. | 84 ± 2 (N = 3) | 20 ± 5 (N = 3) |
| Substituted Cyclopentadienyl Compounds | | | | | | |
| VMDC | 123 | 86 | 61 | N.D. | 45 (27, 61) | 13 (13, 14) |
| VPMDC | 127 | 44 | 172 | N.D. | 35 (35, 36) | 34 (33, 35) |
| VPMOC | >250 | 77 | N.D. | N.D. | 5 (5, 6) | 6 (6, 7) |
| Control | | | | | | |
| VDSO$_4$ | >250 | >250 | N.D. | N.D. | N.D. | |

Example 2

Oxovanadium (IV) Compounds

Materials and Methods

The oxovanadium (IV) complexes were synthesized based on previously published chemistry of VO(phen) and VO(phen)$_2$ complexes. Sakurai, et. al, Biochemical and Biophysical Research Communications, Vol. 206, No. 1, (1995). Selbin, et. al, Chemical Reviews, Vol. 65, No. 2 (1965). Briefly, these complexes were synthesized by reacting an aqueous solution of vanadyl sulfate with an ethanol solution or a chloroform solution of the ligands.

The complexes purified from chloroform, ether and/or water were characterized by Fourier transform infrared spectroscopy (FT-Nicolet model Protege 460; Nicolet Instrument Corp., Madison, Wis.), UV-visible spectroscopy (DU 7400 spectophotometer; Beckman Instruments, Fullerton, Calif.) and elemental analysis (Atlantic Microlab, Inc., Norcross, Ga.). These oxovanadium (IV) complexes have an octahedral or square pyramidal geometry with the oxo ligand ($O^{2-}$) in the axial site. The oxovanadium complexes are stabilized with bidentate ligands which form a 5-membered ring with the vanadium atom. The choice of these three organic ligands (phenanthroline, bipyridyl, bipyrimidal and acetophenone) was based on the reported fact that the cationic oxovanadium(IV) complex of phenanthroline is superior to cisplatin (cis-diamminedichloroplatinum [II]) with respect to antitumor activity, the structural similarity of bipyridyl ring to phenanthroline, as well as the neutral nature of acetophenone complex of oxovanadium (IV).

Structural variations of the ligands included addition of bromo, chloro or methyl groups on the phenanthroline, bipyridyl or acetophenone rings. The chemical structures of the oxovanadium (IV) complexes, including 8 complexes with 1,10-phenanthroline and 4 complexes with 2,2'-bipyridyl, and one neutral complex, bis-5'-bromo-2'-hydroxyacetophenone, are depicted in Table 6. The synthesis and analysis of the compounds can be summarized as follows.

[VO(Phen)($H_2O$)$_2$]($SO_4$) (Phen=1,10phenanthroline) (diaqua)(1,10-phenanthroline)oxovanadium(IV) Sulfate (Compound 26). A chloroform solution of 1,10-phenanthroline (90.1 mg, 0.5 mmol) was added to VO($SO_4$).$3H_2O$ (108.5 mg, 0.5 mmol) in 6 mL of water. The resulting green solution was stirred at room temperature for 3 h, and then stored in refrigerator for one day. The green water layer was separated from the chloroform layer, and water was removed by vacuum. The green solid product (165 mg, 87%) was washed with chloroform and ether, and dried in air. Anal. Calcd for [VO(Phen)($H_2O$)$_2$]($SO_4$) ($C_{12}H_{12}N_2O_7SV$): C, 38.01; H, 3.20; N, 7.39. Found: C, 38.57; H, 3.07; N, 7.47. IR spectrum: $\upsilon$(V=O) 978 $cm^{-1}$.

[VO($SO_4$)(Phen)$_2$] bis(1,10-phenanthroline) sulfatooxovanadium(IV) (Compound 27). An ethanol solution of 1,10-phenanthroline (180.2 mg, 1.0 mmol) was added to VO($SO_4$).$3H_2O$ (108.5 mg, 0.5 mmol) in 6 mL of water. The resulting brown solutionwas stirred at room temperature for 3 h, and brown microcrystals precipitated from the solution upon standing at $-20°$ C. The product (247 mg, 89%) was washed with chloroform and ether, and dried in air. Anal. Calcd for [VO($SO_4$)(Phen)$_2$].$2H_2O$ ($C_{24}H_{20}N_4O_7SV$): C, 51.53; H, 3.60; N, 10.01. Found: C, 50.92; H, 3.65; N, 9.87. IR spectrum: $\upsilon$(V=O) 978 $cm^{-1}$.

[VO($Me_2$-Phen)($H_2O$)$_2$]($SO_4$) ($Me_2$-Phen=4,7-dimethyl-1,10-phenanthroline) (diaqua)(4,7-dimethyl-1,10-phenanthroline)oxovanadium(IV) Sulfate (Compound 28). A chloroform solution of 4,7-dimethyl-1,10-phenanthroline (104.1, 0.5 mmol) was added to VO($SO_4$).$3H_2O$ (108.5 mg, 0.5 mmol) in 6 mL of water resulting in the precipitation of a green solid. The reaction mixture was stirred at room Temperature for one day, and the product (128 mg, 63%) was filtered and washed with water and ether, and dried in air. Anal. Calcd for [VO($Me_2$-Phen)($H_2O$)$_2$]($SO_4$) ($C_{14}H_6N_2O_7SV$): C, 41.29; H, 3.96; N, 6.88. Found: C, 41.08; H, 4.12; N, 6.74. IR spectrum: $\upsilon$(V=O) 978 $cm^{-1}$.

[VO($SO_4$)($Me_2$-Phen)$_2$]bis(4,7-dimethyl-1,10-phenanthroline) sulfatooxovanadium(IV) (Compound 29) was prepared by mixing an aqueous solution of VO($SO_4$).$3H_2O$ (54.3 mg, 0.25 mmol) with an ethanol solution of 4,7-dimethyl-1,10-phenanthroline (104.2 mg, 0.5 mmol) at room temperature. The reaction mixture was stirred at room temperature for 2 days. During this time, the blue solution first turned to green and then to brown. The brown solid product (107 mg, 68%) was obtained by removing solvent and washing with chloroform and ether, and drying under vacuum. Anal. Calcd for [VO($SO_4$)($Me_2$-Phen)$_2$].$3H_2O$ ($C_{28}H_{30}N_4O_8SV$): C, 53.08; H, 4.77; N, 8.84. Found: C, 53.01; H, 4.58; N, 8.84. IR spectrum: $\upsilon$(V=O) 973 $cm^{-1}$.

[VO(Cl-Phen)($H_2O$)$_2$]($SO_4$) (diaqua)(5-chloro-1,10-phenanthroline) oxovanadium(IV) Sulfate (Compound 30) was prepared by mixing an aqueous solution Of VO($SO_4$).$3H_2O$ (108.5 mg, 0.5 mmol) with an ethanol solution of 5-chloro-1,10-phenanthroline (107.3 mg, 0.5 mmol) at room temperature. The reaction mixture was stirred at room temperature for two days. During this time, the blue solution turned to green. The green solid product (142.3 mg, 69%) was obtained by removing solvent and purifying from water and ether, and drying under vacuum. Anal. Calcd for [VO(Cl-Phen)($H_2O$)$_2$]($SO_4$) ($Cl_2H_{11}N_2O_7ClSV$): C, 34.84; H, 2.68; N, 6.77. Found: C, 34.96; H, 2.64; N, 6.84. IR spectrum: $\upsilon$(V=O) 964 $cm^{-1}$.

[VO($SO_4$)(Cl-Phen)$_2$] (Cl-Phen=5-chloro-1,10-phenanthroline) bis(5-chloro-1,10-phenanthroline) sulfatooxovanadium(IV) (Compound 31). An ethanol solution of 5 chloro-1,10-phenanthroline (214.7 mg, 1.0 mmol) was added to VO($SO_4$).$3H_2O$ (108.5 mg, 0.5 mmol) in 6 mL of water. The resulting brown solution was stirred at room temperature for 7 h, and a small amount of brown microcrystals precipitated upon standing at $-20°$ C. The brown solid product (222 mg, 71%) was obtained by removing solvent and washing with chloroform and ether, and drying under vacuum. Anal. Calcd for [VO($SO_4$)(Cl-Phen)$_2$].$2H_2O$ ($C_{24}H_{18}N_4O_7Cl_2SV$): C, 45.88; H, 2.89; N, 8.92. Found: C, 45.44; H, 2.87; N, 8.75. IR spectrum: $\upsilon$(V=O) 962 $cm^{-1}$.

[VO($NO_2$-Phen)($H_2O$)$_2$]($SO_4$) ($NO_2$-Phen=5-nitro-1,10-phenanthroline) (diaqua)(5-nitro-1,10-phenanthroline) oxovanadium(IV) Sulfate (Compound 32) was prepared by adding a blue aqueous solution of VO($SO_4$).$3H_2O$ (108.5 mg, 0.5 mmol) into a yellow suspension of 5-nitro-1,10-phenanthroline (112.6 mg, 0.5 mmol) in ethanol at room temperature. The reaction mixture turned to green solution immediately, and then was stirred at room temperature for two days. During this time, some brown solid precipitated. The brown solid was filtered off and the filtrate was evaporated to dryness to give rise to a green solid. The green solid product (90.7 mg, 43%) was obtained by purifying from water and ether, and drying under vacuum. Anal. Calcd for [VO($NO_2$-Phen) ($H_2O$)$_2$]($SO_4$) ($C_{12}H_{11}N_3O_9SV$): C, 33.97; H, 2.61; N, 9.91. Found: C, 33.70; H, 2.54; N, 9.78. IR spectrum: $\upsilon$(V=O) 980 $cm^{-1}$.

[VO($SO_4$)($NO_2$-Phen)$_2$]bis(5-nitro-1,10-phenanthroline) Sulfatooxovanadium(IV) (Compound 33) was prepared by mixing a blue aqueous solution of VO($SO_4$).$3H_2O$ (108.5 mg, 0.5 mmol) with a yellow suspension of 5-nitro-1,10-phenanthroline (225.2 mg, 1 mmol) in ethanol at room temperature. A brown solution was generated upon the mixing and a yellow solid precipitated gradually. The reaction mixture was stirred at room temperature for one day. The yellow solid product (180 mg, 54%) was obtained by filtration and washing with water, chloroform and ether, and drying in air. Anal. Calcd for [VO($SO_4$)($NO_2$-Phen)$_2$].$3H_2O$ ($C_{24}H_{20}N_6O_{12}SV$): C, 43.18; H, 3.02; N, 12.59. Found: C, 42.61; H, 2.98; N, 12.28. IR spectrum: $\upsilon$(V=O) 976 $cm^{-1}$.

[VO(Bpy)(H$_2$O)$_2$](SO$_4$) (Bpy=2,2'-bipyridine) (diaqua)(2,2' bipyridyl) oxovanadium(IV) Sulfate (Compound 34). A chloroform solution of 2,2'-bipyridine (78.1 mg, 0.5 mmol) was added to VO(SO$_4$).3H$_2$O (108.5 mg, 0.5 mmol) in 6 mL of water. The resulting green solution was stirred at room temperature overnight, and then the water layer was separated from the chloroform layer. The green solid product (105 mg, 59%) was obtained by removing water and washing with ether, and drying in air. Anal. Calcd for [VO(Bpy)(H$_2$O)$_2$](SO$_4$) (C$_{10}$H$_{12}$N$_2$O$_7$SV): C, 33.81; H, 3.41; N, 7.89. Found: C, 33.77; H, 3.16; N, 7.72. IR spectrum: υ(V=O) 978 cm$^{-1}$.

[VO(SO$_4$)(Bpy)$_2$]bis(2,2'-bipyridyl)sulfatooxovanadium(IV) (Compound 35). An ethanol solution of 2,2'-bipyridine (156.2 mg, 1.0 mmol) was added to VO(SO$_4$).3H$_2$O (108.5 mg, 0.5 mmol) in 6 mL of water. The resulting brown solution was stirred at room temperature overnight, and then stored at −20° C. for one day. The brown solid product (180 mg, 76%) was obtained by removing solvent and washing with chloroform, ethanol and ether, and drying in air. Anal. Calcd for [VO(SO$_4$)(Bpy)$_2$]H$_2$O (C$_{20}$H$_{18}$N$_4$O$_6$SV): C, 48.69; H, 3.68; N, 1 1.36. Found: C, 48.38; H, 3.81; N, 11.48. IR spectrum: υ(V=O) 978 cm$^{-1}$.

[VO(Me$_2$-bpy)(H$_2$O)$_2$](SO$_4$) (Me$_2$-bpy=4,4'-dimethyl-2,2-bipyridyl) (diaqua)(4,4'-dimethyl-2,2'-bipyridyl) oxovanadium(IV) Sulfate (Compound 36). A chloroform solution of 4,4'-dimethyl-2,2'-bipyridyl (104.1 mg, 0.5 mmol) was added to VO(SO$_4$).3H$_2$O (108.5 mg, 0.5 mmol) in 6 mL of water. The reaction mixture was stirred at room temperature for one day, during this time a green solid formed. The product (130 mg, 68%) was filtered and washed with water and ether, and dried in air. Anal. Calcd for [VO(Me$_2$-bpy)(H$_2$O)$_2$](SO$_4$)(C$_{12}$H$_{16}$N$_2$O$_7$SV): C, 37.61; H, 4.21; N, 7.31. Found: C, 37.49; H, 4.27; N, 7.16. IR spectrum: υ(V=O) 983 cm$^{-1}$.

[VO(SO$_4$)(Me$_2$-bpy)$_2$]bis(4,4'-dimethyl-2,2'-bipyridyl) sulfatooxovanadium(IV) (Compound 37). An ethanol solution of 4,4'-dimethyl-2,2'-bipyridyl (92.1 mg, 0.5 mmol) was added to VO(SO$_4$).3H$_2$O (54.3 mg, 0.25 mmol) in 6 mL of water. The reaction mixture was stirred at room temperature for 20 h, and a small amount of green solid precipitated. The green solid was removed by filtration. The yellow solid product (72 mg, 51%) was obtained by removing solvent and washing by chloroform and ether, and drying under vacuum. Anal. Calcd for [VO(SO$_4$)(Me$_2$-bpy)$_2$].2H$_2$O (C$_{24}$H$_{28}$N$_4$O$_7$SV): C, 50.79; H, 4.97; N, 9.87. Found: C, 50.19; H, 4.81; N, 9.67. IR spectrum: υ(V=O) 978 cm$^{-1}$.

[VO(Bipym)(H$_2$O)$_2$](SO$_4$) (Bipym=2,2'-bipyrimidine) (diaqua)(2,2'-bipyrimidine) oxovanadium(II) sulfate (Compound 38) was prepared by mixing an aqueous solution of VO(SO$_4$).3H$_2$O (86.8 mg, 0.4 mmol) with an ethanol solution of 2,2'-bipyrimidine (63.3 mg, 0.4 mmol) at room temperature. The reaction mixture was stirred at room temperature for two days. During this time, the blue solution turned to green. The green solid product (112.3 mg, 77%) was obtained by removing solvent and washing with ether, and drying under vacuum. Anal. Calcd for [VO(Bipym)(H$_2$O)$_2$](SO$_4$).0.5H$_2$O (C$_8$H$_{11}$N$_4$O$_{7.5}$SV): C, 26.24; H, 3.03; N, 15.30. Found: C, 25.99; H, 2.9 1; N, 15.20. IR spectrum: υ(V=O) 978 cm$^{-1}$.

[VO(SO$_4$)(Bipym)$_2$]bis(2,2'-bipyrimidine) sulfatooxovanadium(IV) (Compound 39) was prepared by mixing an aqueous solution of VO(SO$_4$).3H$_2$O (43.4 mg, 0.2 mmol) with an ethanol solution of 2,2'-bipyrimidine (63.3 mg, 0.4 mmol) at room temperature. The reaction mixture was stirred at room temperature for 5 days, and then kept in refrigerator overnight. During this time, the blue solution turned to green. The green solid product (80 mg, 75%) was obtained by removing solvent and washing with chloroform and ether, and drying under vacuum. Anal. Calcd for [VO(SO$_4$)(Bipym)$_2$].3H$_2$O (C$_{16}$H$_{18}$N$_8$O$_8$SV): C, 36.03; H, 3.40; N, 21.01. Found: C, 35.83; H, 3.12; N, 21.12. IR spectrum: υ(V=O) 974 cm$^{-1}$.

[VO(Br,OH-acph)$_2$](Br,OH-acph=5'-bromo-2'-hydroxyacetophenone) bis(5'-bromo-2'-hydroxyacetophenone)oxovanadium(IV) (Compound 40). An ethanol solution of 5'-bromo-2'-hydroxyacetophenone (107.6 mg, 0.5 mmol) was added to VO(SO$_4$)-3H$_2$O (108.5 mg, 0.5 mmol) in water (5 mL). The solution turned to green immediately and a white solid precipitated in a few minutes. After one hour, an aqueous solution of NaOH (20 mg, 0.5 mmol) was added, and the reaction mixture was stirred at room temperature for one day. The resulting yellow solid product (63.5 mg, 40%) was filtered and washed with water and ether, and dried in air. Anal. Calcd for [VO(Br,OH-acph)$_2$].0.5H$_2$O (C$_{16}$H$_{13}$O$_{5.5}$Br$_2$V): C, 38.13; H, 2.60; Br, 31.71. Found: C, 38.18; H, 2.36, Br, 31.65. IR Spectrum: υ(V=O) 971 cm$^{-1}$.

TABLE 6

Oxovanadium(IV) Compounds.

| Compound | Structure | UV-vis λ, nm (ε, M$^{-1}$ cm$^{-1}$) [Solvent] | IR υV = O, cm$^{-1}$ | Elemental Anaylsis Found (Calcd.) C, H, N |
|---|---|---|---|---|
| 26 | 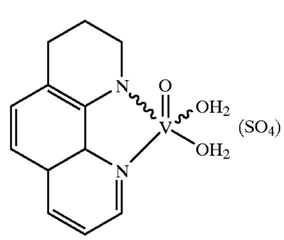 | 970 (sh), 745 (34), 529 (21), 432 (sh) [H$_2$O] | 978 | 38.57 (38.01), 3.07 (3.20), 7.47 (7.39) |

TABLE 6-continued

Oxovanadium(IV) Compounds.

| Compound | Structure | UV-vis λ, nm (ε, M⁻¹ cm⁻¹) [Solvent] | IR υV = O, cm⁻¹ | Elemental Anaylsis Found (Calcd.) C, H, N |
|---|---|---|---|---|
| 27 | 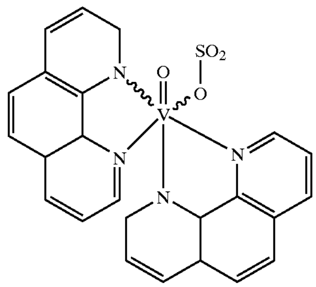 | 712 (33), 540 (sh), 436 (sh) [H₂O] | 978 | 50.92 (51.53), 3.65 (3.60), 9.87 (10.01) |
| 28 | 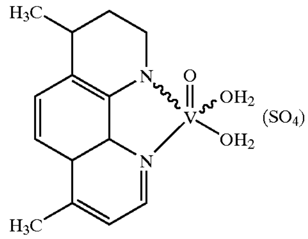 | ND | 978 | 41.08 (41.29), 4.12 (3.96), 6.74 (6.88) |
| 29 | 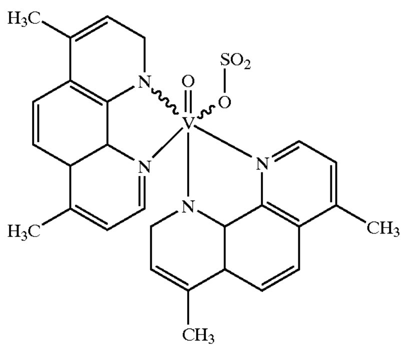 | 664 (83), [H₂O] 765 (37), 448 (236) [DMSO] | 973 | 53.01 (53.08), 4.58 (4.77), 8.84 (8.84) |
| 30 | 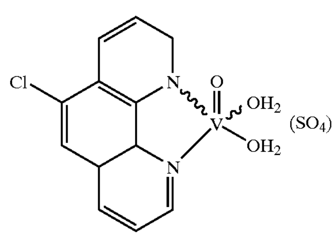 | 745 (30), 523 (18), 438 (sh), [H₂O] | 964 | 34.96 (34.84), 2.64 (2.68), 6.84 (6.77) |
| 31 | 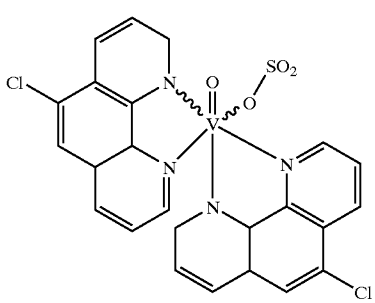 | 685 (58), 535 (sh), 446 (sh), [H₂O] | 962 | 45.44 (45.88), 2.87 (2.89), 8.75 (8.92) |

TABLE 6-continued

Oxovanadium(IV) Compounds.

| Compound | Structure | UV-vis $\lambda$, nm ($\epsilon$, $M^{-1}$ $cm^{-1}$) [Solvent] | IR $\upsilon V = O$, $cm^{-1}$ | Elemental Anaylsis Found (Calcd.) C, H, N |
|---|---|---|---|---|
| 32 | (5-nitro-phenanthroline)VO(OH$_2$)$_2$(SO$_4$) | 746 (34), 444 (sh) [H$_2$O] | 980 | 33.70 (33.97), 2.54 (2.61), 9.78 (9.91) |
| 33 | bis(5-nitro-phenanthroline)VO(SO$_4$) | 757 (34), 459 (sh) [DMSO] | 976 | 42.61 (43.18), 2.98 (3.02), 12.28 (12.59) |
| 34 | (2,2'-bipyridine)VO(OH$_2$)$_2$(SO$_4$) | 968 (sh), 749 (23), 535 (sh), [H$_2$O] | 978 | 33.77 (33.81), 3.16 (3.41), 7.72 (7.89) |
| 35 | bis(2,2'-bipyridine)VO(SO$_4$) | 726 (27), 533 (19), 453 (sh), [H$_2$O] | 978 | 48.43 (48.69), 3.81 (3.68), 11.48 (11.36) |
| 36 | (4,4'-dimethyl-2,2'-bipyridine)VO(OH$_2$)$_2$(SO$_4$) | ND | 983 | 37.49 (37.61), 4.27 (4.21), 7.16 (7.31) |

TABLE 6-continued

Oxovanadium(IV) Compounds.

| Compound | Structure | UV-vis λ, nm (ε, M⁻¹ cm⁻¹) [Solvent] | IR υV = O, cm⁻¹ | Elemental Anaylsis Found (Calcd.) C, H, N |
|---|---|---|---|---|
| 37 | (structure) | 701 (51), 535 (49) [H$_2$O] | 978 | 50.19 (50.79), 4.81 (4.97), 9.67 (9.87) |
| 38 | (structure) | 752 (23), 572 (sh), 406 (sh), [H$_2$O] | 978 | 25.99 (26.24), 2.91 (3.03), 15.20 (15.30) |
| 39 | (structure) | 753 (23), 564 (sh), 410 (sh), [H$_2$O] | 974 | 35.83 (36.03), 3.12 (3.40), 21.12 (21.01) |
| 40 | (structure) | 833 (55), 621 (62), 502 (185) [DMSO] | 971 | C, 38.18 (38.13), H, 2.36 (2.60), Br, 31.65 (31.71) |

Cell Lines and Culture Conditions

Human testicular cancer cell lines, Tera-2 (embryonal carcinoma) and Ntera-2 (pluripotent embryonal carcinoma) were obtained from the American Type Culture Collection (ATCC) (Rockeville, Md.) and propagated in T-25, T-75, or T-150 cm$^2$ tissue culture flasks (Corning Corp., Corning, N.Y.) in McCoy's 5A medium and Dulbecco's modified Eagle's medium respectively. Both media were supplemented with 10% fetal calf serum (FCS), 4 mM glutamine, 100 U/ml penicillin G, and 100 mg/ml streptomycin sulfate. All tissue culture reagents were obtained from Life Technologies Inc. (GIBCO-BRL), Gaithersburg, Md. Cell lines were cultivated for a minimum of two passages after thawing prior to experimentation. Other cell lines that were used in this study were the human B-lineage acute lymphoblastic leukemia (ALL) cell line NALM-6. Uckun, F. M., Evans, W. E., Forsyth, C. J., Waddick, K. G., Tuel-Ahigren, L., Chelstrom, L. M., Burkhardt, A., Bolen, J., Myers, D. E. Biotherapy of B-cell precursor leukemia by targeting genistein to CD19-associated tyrosine kinase. Science (Washington D.C.) 267.886–91, 1995; T-lineage ALL cell line MOLT-3, Waurzyniak, B., Shneider, E. A., Tumer, N., Yanishevski, Y., Gunther, R., Chelstrom, L., Wendorf, H., Myers, D. E., Irvin, J. D., Messinger, Y., Ek, O., Zeren, T., Chandan-Langlie, M., Evans, W. E., Uckun, F. M. In vivo toxicity, pharmacokinetics, and antileukemic activity of TXU (anti-CD7)-pokeweed antiviral protein immunotoxin. Clinical Cancer Research 3:881–890, 1997; AML cell line HL60, Perentesis, J. P., Waddick, K. G., Bendel, A. E., Shao, Y., Warman, B. E., ChandanLanglie, M., and Uckun, F. M. Induction of apoptosis in multi-drug resistant andradiation-resistant acute myeloid leukemia cells by a recombinant fusion toxin directed against the granulocyte macrophage colony stimulating factor receptor. Clin. Cancer Res. 3:347–355, 1997; breast cancer cell lines MDA-MB-23 land BT-20, Uckun, F. M., Narla, R. K., Jun, X., Zeren, T., Venkatachalam, T., Waddick, K. G., Rostostev, A., Myers, D. E. Cytotoxic activity of EGF-genstein against breast cancer cells. Clin. Cancer Res. 4:901–912, 1998; glioblastoma cell lines U87 and U373, Narla, R. K., Liu, X., Myers, D. E., and Uckun, F. M. 4-(3'-Bromo-4'hydroxylphenyl)-amino-6,7-dimethoxyquinazoline (WHI-P154): A novel quinazoline derivative with potent cytotoxic activity against human glioblastoma cells. Clin. Cancer Res. 4:1405–1414, 1998.
MTT Assays.

MTT (3-[4,5-dimethyl thiazol-2-yl]-2,5-diphenyltetrazoliuin bromide)-based calorimetric assays were used for evaluation of the cytotoxicity of vanadocene compounds. Mosmann, T. Rapid colorimetric assay for cellular growth and survival: application to proliferation and cytotoxicity assays. J. Immunol. Methods, 65: 55–63, 1983. Briefly, cells were harvested with 0.125% (w/v) trypsin-0.02% EDTA (GIBCO-BRL) from exponential-phase maintenance cultures and centrifuged (300 g×5 min). After suspension and counting, cells were dispensed within triplicate 96-well tissue culture plates in 1001 $\mu$l volumes. After 24 h incubation, the culture medium was discarded and replaced with 100 $\mu$l of fresh medium containing serial two-fold dilutions of drugs in medium to yield 1.9 $\mu$M to 250 $\mu$M. All compounds were reconstituted in DMSO to a concentration of 100 mM, and the stock solution was made fresh for each experiment. Control wells consisted of medium containing 0.25% of DMSO alone were used for solvent control. Culture plates were then incubated for 24 h before adding 10 $\mu$l of MTT solution (5 mg/ml in PBS) to each well. Wells containing only medium and MTT were used as controls for each plate. The tetrazolium/formazan reaction was allowed to proceed for 4 h at 37° C., and then 100 $\mu$l of the solubilization buffer (10% sodium dodecyl sulfate in 0.1% HCl) were added to all wells and mixed thoroughly to dissolve the dark blue formazan crystals. After an overnight incubation at 37° C., the optical densities at 540 nm were measured using a 96-well multiscanner autoreader, with the solubilization buffer serving as blank. All assays were run in triplicate and results were expressed as $IC_{50}$ values. The $IC_{50}$ was defined as the concentration required for 50% reduction of the optical density in each test, and was calculated as: ($A_{540}$ of drug-treated wells–$A_{540}$ of control wells)/$A_{540}$ of drug-free wells×100.

Adhesion Assays

In vitro adhesion assays, Narla R K, Liu X P, Klis D, Uckun F M. Inhibition of human glioblastoma cell adhesion and invasion by 4-(4'-hydroxyphenyl)-amino-6,7-dimethoxyquinazoline (WHI-P131) and 4-(3'-bromo-4'-hydroxyphenyl)-amino-6,7-dimethoxyquinazoline (WHI-P154). Clin Cancer Res 4:2463–71, 1998, were performed to (a) study the baseline adhesive properties of U373 glioblastoma and TERA-2 testicular cancer cell lines and (b) evaluate the effects of VDC and VDSeCN derivatives on the adhesive properties of U373 glioblastoma and TERA-2 testicular cancer cells. The plates for the adhesion assays were precoated with the extracellular matrix proteins laminin, fibronectin or type IV collagen (each at a final concentration of 1 $\mu$g/ml in PBS) overnight at 4° C. and dried. On the day of the experiment, the wells were rehydrated and blocked with 10% bovine serum albumin in PBS for 1 hr at room temperature and used for the adhesion assays, as described below. To study the effects of VDC and VDSeCN on cancer cell adhesion, exponentially growing cells in DMEM were incubated with these compounds at concentrations ranging from 1 $\mu$M to 10 $\mu$M for 16 hr in a humidified 5% $CO_2$ atmosphere. DMSO (0.1%) was included as a vehicle control. After treatment, cells were detached from the flasks with 0.05% trypsin (Life Technologies) resuspended in DMEM, incubated at 37° C. for 2 hr to allow them to recover from the trypsinization stress and examined for their ability to adhere to plates precoated with ECM proteins. Cells were centrifuged, washed twice with serum-free DMEM, counted and resuspended in serum-free DMEM to a final concentration of $2.5 \times 10^5$ cells/ml. One hundred $\mu$l of the cell suspension containing $2.5 \times 10^4$ cells were added to each well and cells were allowed to adhere for 1 hr at 3° C. in a humidified 5% $CO_2$ atmosphere. The non-adherent cells were removed by gently washing the cells with PBS and then the adherent fraction was quantitated using MTT (3-[4,5-dimethylthiazol-2-yl]-2,5-diphenyl tetrazolium bromide) assays as described above. The adherent fractions of cells treated with VDC or VDSeCN were compared to those of DMSO treated control cells and the percent inhibition of adhesion was determined using the formula: % Inhibition=100×(1–Adherent Fraction of Drug-Treated Cells/Adherent Fraction of Control Cells). Each treatment condition was evaluated in duplicate in 3 independent experiments. The $IC_{50}$ values were calculated by non-linear regression analysis using an Graphpad Prism software version 2.0 (Graphpad Software, Inc., San Diego, Calif.).

Cytotoxicity of Oxovanadium Compounds Against Human Cancer Cell Lines

A series oxovanadium (IV) complexes (Table 6) were prepared, including eight phenanthroline (phen)-linked [VO (phen), VO(phen)$_2$, VO(Me$_2$-phen), VO (Me$_2$-phen)$_2$, VO(Cl-phen), VO(Cl-phen)$_2$, VO(NO$_2$-phen), VO(NO$_2$-phen)$_2$] and six bipyridyl (bipy)-linked [VO(bipy), VO(bipy)$_2$, VO(Me$_2$-bipy), VO(Me$_2$-bipy)$_2$, two bipyramide VO, and two bipyramide VO$_2$, and one acetophenone (acph)-linked [VO(Br,OH-acph)$_2$] and tested their cytotoxic activity against 14 different human cancer cell lines, including the B-lineage ALL cell line NALM-6, T-lineage ALL cell line MOLT-3, AML cell line HL-60, multiple myeloma cell lines ARH-77, U266BL, and HS-SULTAN, Hodgkin's lymphoma cell line HS445, and the testicular cancer cell lines 833K, 64 cp5, TERA-2, and NTD1, prostate cancer cell line PC3, breast cancer cell line BT-20, and glioblastoma cell line U373 using MTT assays and/or confocal laser scanning microscopy. Each compound was tested side-by-side at eight different concentrations in the range of 0.1–250 $\mu$M.

Each of the 15 oxovanadium complexes exhibited significant cytotoxicity against several of the cancer cell lines in a concentration-dependent fashion (Table 7, FIG. 1). FIG. 1 shows the concentration-dependent MTT-based cytotoxicity curves of 12 representative oxovanadium (IV) compounds against NALM-6 leukemia cells. The cytotoxic activity of the oxovanadium(IV) complexes was strongly dependent on the type of coordinated heteroligands. When compared with diaqua mono-chelated complexes, the butterfly structure oxovanadium complexes stabilized with 5-membered bis-chelated ligands of phenanthroline or bipyridyl showed superior cytotoxic activity against cancer cells.

The mono-chelated [VO(Me$_2$-phen)=compound 28] as well as bis-chelated-1,10-phenantroline complexes [VO(Me$_2$-phen)$_2$=compound 29] were the most potent oxovanadium compounds and killed each of the 7 cell lines examined at low micromolar concentrations (Table 7). Notably, the dimethyl substitution of the phenanthroline rings is believed to be significant for the anti-cancer activity of both compounds (29) [=VO(Me$_2$-phen)$_2$] and (28) [VO(Me$_2$-phen)$_1$] because unsubstituted bis-chelated and mono-chelated 1,10-phenanthroline oxovanadium (IV) complexes [VO(phen)= compound 276 or VO(phen)$_2$=compound 27] were less active. Addition of a chloro or nitro group to the 1,10-phenanthroline complexes did not significantly improve the cytotoxic activity of the unsubstituted oxovanadium (IV) complexes (Table 7). Irrespective of the ligands, bis-chelated phenanthroline containing compounds showed better activity than the mono-chelated phenanthroline containing complexes. The marked differences in the cytotoxic activity of oxovanadium (IV) complexes containing different heterocyclic ancillary ligands suggest that the cytotoxic activity of these compounds is determined by the identity of the 5-membered bidentate ligands as well as the nature of the substitutents on the heterocyclic aromatic rings. The ability of oxovanadium compounds to inhibit the in vitro clonogenic growth of NALM-6 leukemia cells was also investigated. As detailed in Table 7, compounds 28 and 29 were the most potent compounds against clonogenic NALM-6 cells and completely abrogated in vitro colony formation at concentrations <1 $\mu$M.

Oxovanadium (IV) Compounds Induce Apoptosis in Human Cancer Cells

Figure 2A:
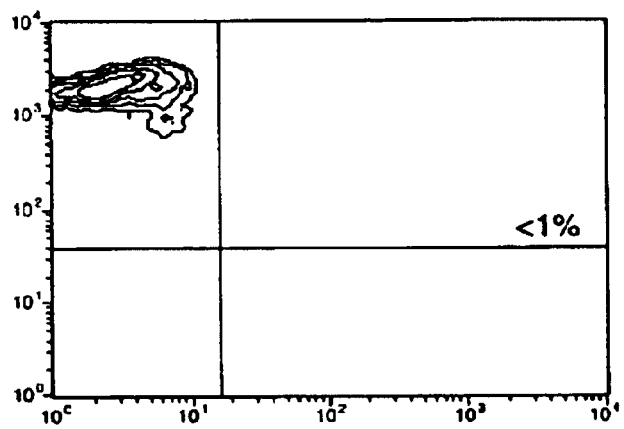
FIG. 2. Illustrates VDSeCN and VDSCN induce apoptosis in human testicular cancer cells. (Left panels) TUNEL analysis: Two-color flow cytometric contour plots of Ntera-2 cells treated with and without vanadocenes. Cells were incubated for 24 h in either control medium (0.1% DMSO) [A], or in medium supplemented with 100 μM VDSCN [C] or VDSeCN [E] in 0.1% DMSO, fixed, permeabilized, and visualized for DNA-fragmentation in a TUNEL assay using TdT and FITC-dUTP. Red fluorescence represents nuclei counterstained with propidium iodide. Percentages indicate cells with increased dUTP incorporation. (Right panels) Confocal images: Two-color confocal laser scanning microscopy images of control and apoptotic cells. B) Control cells visualized for dUTP incorporation using FITC-dUTP. D and F) Apoptotic nuclei of cells treated with VDSCN and VDSeCN are recognized by fluorescein labeled green/yellow (superimposed red plus green) fluorescence. Original magnification×600.
Figure 2B:
Figure 2C:
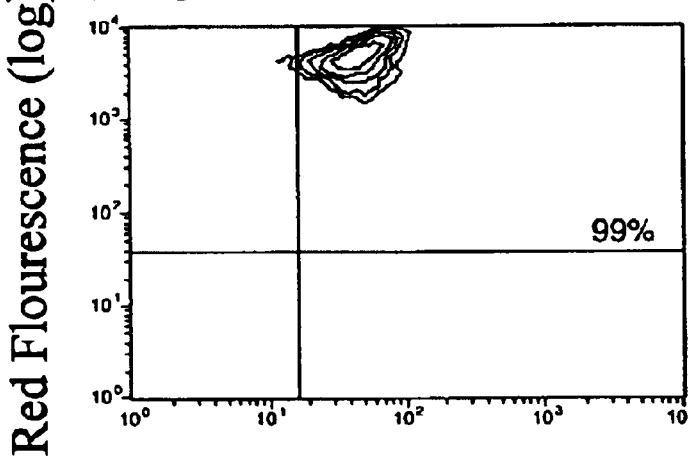
Figure 2D:
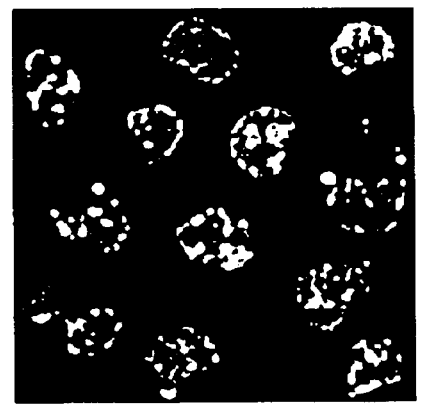
Figure 2E:
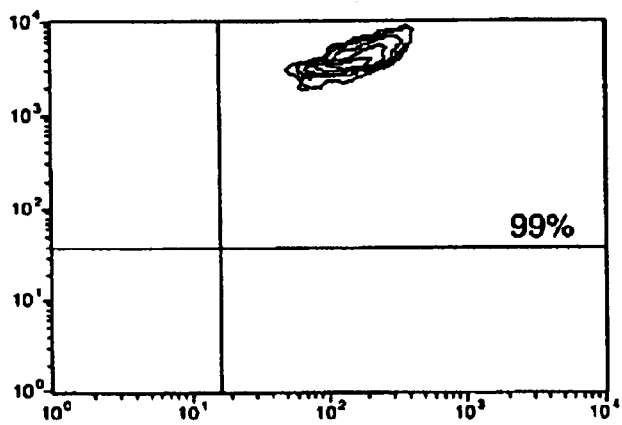
Figure 2F:
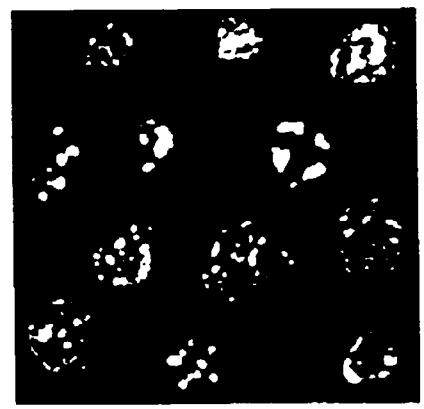
Figure 3A:
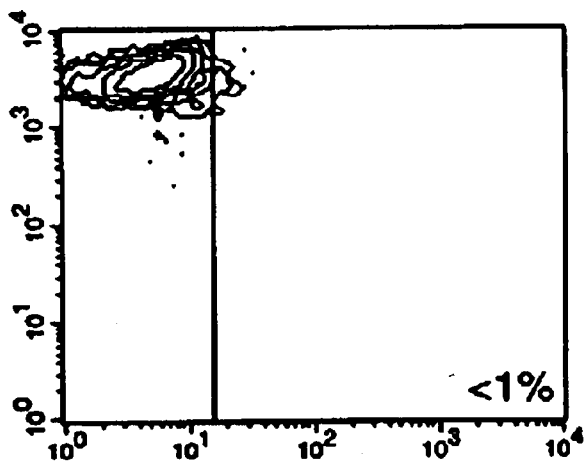
FIG. 3. Illustrates vanadocenes induce apoptosis in human testicular cancer cells. [Left panels] FACS analysis: Two-color flow cytometric contour plots of Tera-2 cells treated with and without vanadocenes. Cells were incubated for 24 h in either control medium (0.1% DMSO) (A), or in medium supplemented with 100 μM VDA (C), VDCN (E), VDOCN (G), or VDCO (I) in 0.1% DMSO, fixed, permeabilized, and visualized for DNA-fragmentation in a TUNEL assay using TdT and FITC-dUTP. Red fluorescence represents nuclei counterstained with propidium iodide. Percentages indicate cells with increased dUTP incorporation. [Right panels] Confocal images: Two-color confocal laser scanning microscopy images of control and apoptotic cells. (B) Control cells visualized for dUTP incorporation using FITC-dUTP. Apoptotic nuclei of cells treated with VDA (D), VDCN (F), VDOCN (H) and VDCO (J) are recognized by fluorescein labeled green/yellow (superimposed red plus green) fluorescence. Original magnification×600 are recognized by fluorescein labeled (green or yellow[i.e., superimposed red plus green] color) nuclei and apoptotic bodies within the nuclei. (original magnification×600).
Figure 3B:
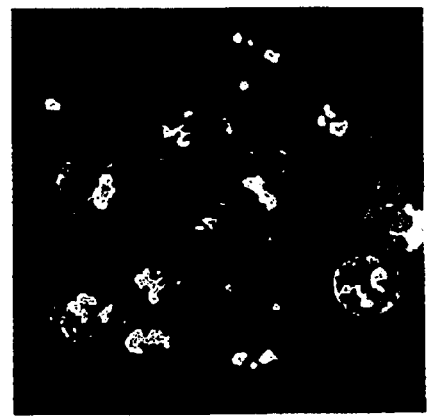
Figure 3C:
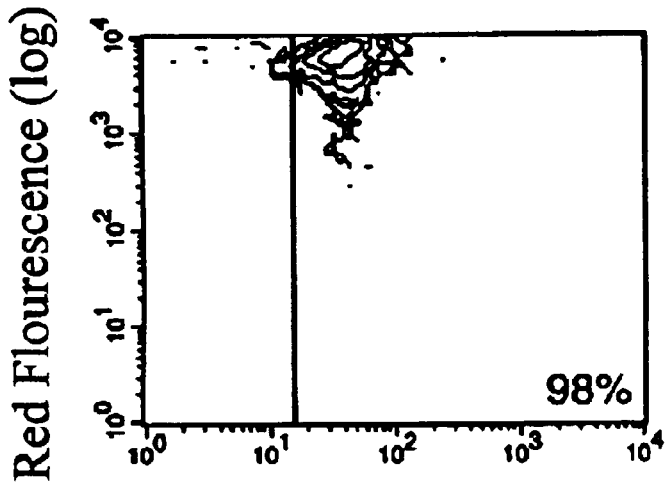
Figure 3D:
Figure 3E:
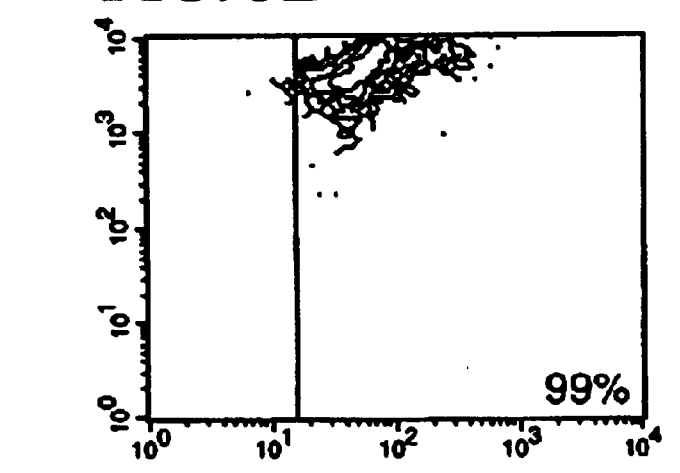
Figure 3F:
Figures 3G, 3H, 3I, 3J:
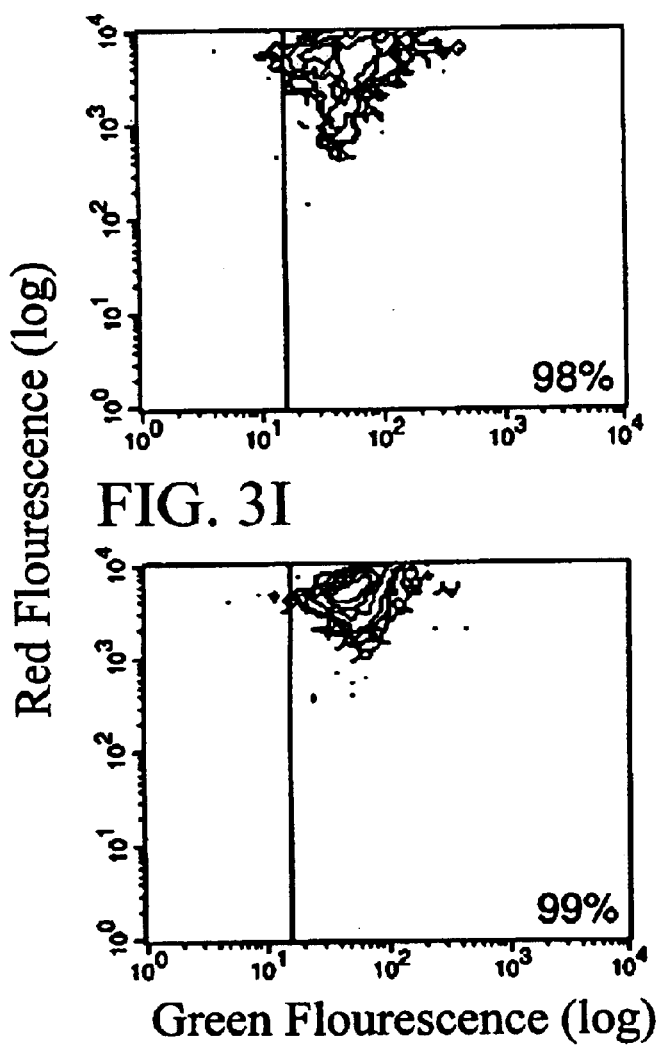

In order to determine if the cytotoxicity of the oxovanadium compounds is associated with apoptotic cell death, 64cp5 and 833-K testicular cancer cells were cultured with the oxovanadium compounds (50 $\mu$M) for 24 h and then subjected to flow cytometric analysis for dUTP incorporation by the TdT-mediated TIJNEL assay. FIG. 2A depicts the two-color flow cytometric contour plots of cells from representative TUNEL assays. Control 64cp5 and 833-K cells were treated for 24 hours at 37° C. with 0.1% DMSO whereas test cells were treated for 24 hours at 37° C. with an oxovanadium compound at 50 $\mu$M final concentration. The TdT-dependent incorporation of FITC-dUTP was dramatically increased in cells treated with the oxovanadium compounds as a result of abundance of free 3'-hydroxyl DNA ends created by endonuclease-mediated DNA fragmentation. Among the 15 vanadocenes evaluated by the flow cytometric TUNEL assay, 8 caused a marked increase in TUNEL-positive nuclei ranging from 50.8 % to 76.1 % for 64cp5 cells and 63.5% to 82.2% for 833-K cells respectively (FIG. 2B). Apoptosis after treatment with oxovanadiuni compounds was also evident from the concentration-dependent emergence of a hypodiploid (2N) peak in the DNA histograms of PI-stained cells, which was accompanied by nonselective loss of G0/1, S, and G2M phase cells (FIG. 2). Similar results were obtained with NALM-6 leukemia and HS-SULTAN multiple myeloma cells (Table 7, FIG. 3). As evidenced by the confocal laser scanning microscopy images depicted in FIG. 5, VO(Me$_2$-phen)$_2$ (compound 29) and VO(Me$_2$-phen) (compound 28) treated [but not VO(Cl-phen)$_2$ (=compound 31)-treated] leukemic NALM-6 and HS-SULTAN cells examined for FITC-conjugated dUTP incorporation (green fluorescence) and propidium iodide counterstaining (red fluorescence) showed many apoptotic yellow nuclei with superimposed green and red fluorescence at 48 hours after treatment. Immunofluorescence staining with anti-$\alpha$-tubulin antibody and the nuclear dye toto-3 in combination with confocal laser scanning microscopy was used to examine the morphological features of cancer cells treated with oxovanadium compounds. FIG. 4 depicts the two-color confocal microscopy images of BT-20 breast cancer, PC3 prostate cancer, and U373 glioblastoma cells after treatment with oxovanadium compounds. Most of the oxovanadium-treated cells displayed the characteristic morphologic features of apoptotic cell death, including an abnormal architecture with complete disruption of microtubules, marked shrinkage, chromatin condensation, nuclear fragmentation, the appearance of typical apoptotic bodies and inability to adhere to the substratum.

In order to test whether oxovanadium compounds induce apoptosis by altering the mitochondrial transmembrane potential, NALM-6 leukemia cells were exposed to compound (29) for apoptosis-associated changes in mitochondrial membrane potential ($\Delta\Psi$m) and mitochondrial mass using specific fluorescent mitochondrial probes and multi-parameter flow cytometry. To measure changes in $\Delta\Psi$m, DiIC1 (which accumulates in energized mitochondria) was used, whereas the mitochondrial mass was determined by staining the cells with NAO, a fluorescent dye that binds to the mitochondrial inner membrane independent of energetic state. Treatment of NALM-6 leukemia cells with compound29 for 24h–72 h increased the number of depolarized mitochondria in a concentration- and time-dependent fashion, as determined by flow cytometry using DiIC1 (27–29) (FIG. 5A). As shown in FIG. 5A, the fraction of DiIC1-negative cells with depolarized mitochondria increased from 6.5% in vehicle treated control cells to 91.5% in cells treated with 1 $\mu$M compound 29 for 48 hours. The average EC$_{50}$ values for compound (29) induced depolarization of mitochondria, as measured by decreased DiIC1 staining were 3.6 $\mu$M, 0.3 $\mu$M and 0.08 $\mu$M for 24 hr 48 hr and 72 hr treatment respectively. The observed changes in $\Delta\Psi$m were not due to loss in mitochondrial mass, as confirmed by a virtually identical staining intensity of NAO in the treated and untreated NALM-6 cells (FIG. 5B). To further confirm this relative change in $\Delta\Psi$m, JC-1, a mitochondrial dye, which normally exists in solution as a monomer emitting green fluorescence and assumes a dimeric configuration emitting red fluorescence in a reaction driven by initochondrial transmembrane potential was used. Thus, the use of JC-1 allows simultaneous analysis of mitochondrial mass (green fluorescence) and initochondrial transmembrane potential (red/orange fluorescence). After treatment of NALM-6 cells with compound 29 at increasing concentrations ranging from 500 nM to 1 $\mu$M and with increasing duration of exposure of 24 h or 48 h, a progressive dissociation between $\Delta\Psi$m and mitochondrial mass was observed, with decrement in JC-1 red/orange fluorescence without a significant corresponding drop in JC-1 green fluorescence. The fraction of JC-1 red/orange fluorescence-positive cells decreased from 98.6% in vehicle-treated control cells to 56. 1% in cells treated with 500 nM of compound 29 for 48 hr and 8.4% in cells treated with 500 nM of compound 29 for 72 hr. The average EC$_{50}$ for compound 29-induced depolarization of initochondria, as measured by JC-1 red/orange fluorescence were 4.2 $\mu$M for the 24 hr treatment and 0.5 $\mu$M for the 48 hr treatment. These results collectively demonstrate that compound 29 causes a significant decrease in mitochondrial transmembrane potential in NALM-6 human leukemia cells.

The results indicate that oxovanadium (IV) complexes with 1,10-phenanthroline, 2,2'-bipyridyl, or 5'-bromo-2'-hydroxyacetophenone and their derivatives linked to vanadium(IV) via nitrogen or oxygen atoms have potent anti cancer activity against human cancer cells. The order of efficacy for the 15 oxovanadium (IV) complexes against NALM-6 leukemia cells as follows: VO (Me$_2$-phen)$_2$>VO (NO$_2$-phen)>VO(Me$_2$-phen)>VO(phen)$_2$, >VO (Cl-phen)$_2$>VO(phen)>VO(Cl-phen)>VO(Me$_2$-bipy)$_2$> VO(NO$_2$-phen)>VO(Me$_2$-bipy)>VObipym>VObipym$_2$> VO(bipy)>VO(bipy)$_2$>VO(Br,OH-acph)$_2$.

Apoptosis induction of cytotines of the oxovanadium compounds of the present invention extend to human sperm. Therefore, these compounds are also useful as sperm or birth control.

TABLE 7

Cytotoxic of Activity Oxovanadium(IV) Compounds Against Leukemia, Hodgkin's Lymphoma and Multiple Myeloma Cells

| Compound | NALM-6 IC$_{50}$ ($\mu$M) | MOLT-3 IC$_{50}$ ($\mu$M) | HS445 IC$_{50}$ ($\mu$M) | HL-60 IC$_{50}$ ($\mu$M) | U266BL IC$_{50}$ ($\mu$M) | ARH77 IC$_{50}$ ($\mu$M) | HS-SULTAN IC$_{50}$ ($\mu$M) |
|---|---|---|---|---|---|---|---|
| 26 | 3.4 ± 0.2 | 2.7 ± 0.2 | 6.3 ± 1.8 | 3.2 ± 1.1 | 3.5 ± 0.5 | 15.6 ± 3.2 | 11.2 ± 2.2 |
| 27 | 0.97 ± 0.1 | 1.4 ± 0.04 | 5.8 ± 1.2 | 4.6 ± 1.4 | 2.2 ± 0.6 | 3.3 ± 0.8 | 4.4 ± 0.8 |
| 28 | 0.78 ± 0.1 | 1.37 ± 0.07 | 3.3 ± 1.4 | 6.2 ± 2.3 | 1.3 ± 0.1 | 8.1 ± 1.6 | 5.1 ± 1.02 |
| 29 | 0.2 ± 0.03 | 0.19 ± 0.01 | 0.5 ± 0.08 | 0.98 ± 0.1 | 0.5 ± 0.02 | 0.81 ± 0.9 | 0.8 ± 0.05 |
| 30 | 3.6 ± 0.07 | 3.4 ± 0.03 | 7.5 ± 2.5 | 15.3 ± 4.9 | 8.5 ± 1.2 | 30.3 ± 5.6 | 9.9 ± 5.4 |
| 31 | 1.6 ± 0.03 | 2.1 ± 0.2 | 5.2 ± 1.1 | 5.3 ± 1.8 | 3.7 ± 1.1 | 10.5 ± 3.8 | 5.8 ± 0.6 |
| 32 | 4.1 ± 0.4 | 2.3 ± 0.3 | 9.1 ± 2.5 | 4.9 ± 1.2 | 18.1 ± 5.1 | 5.4 ± 1.5 | 14.5 ± 2.5 |
| 33 | 0.7 ± 0.01 | 1.4 ± 0.06 | 2.3 ± 0.6 | 2.6 ± 0.4 | 7.2 ± 1.1 | 5.7 ± 1.3 | 13.8 ± 3.6 |
| 34 | 14.9 ± 0.6 | 13.1 ± 1.1 | 41.7 ± 5.4 | >100 | 30.4 ± 7.8 | >100 | 62.8 ± 2.3 |
| 35 | 15.5 ± 3.8 | 14.2 ± 3.8 | 21.6 ± 4.3 | 31.4 ± 6.9 | 32.1 ± 5.2 | 26.8 ± 5.4 | 35.4 ± 3.3 |
| 36 | 8.5 ± 0.5 | 8.2 ± 0.5 | 27.8 ± 3.4 | 38.6 ± 4.5 | 38.4 ± 3.2 | >100 | 65.1 ± 6.1 |
| 37 | 3.9 ± 0.3 | 4.8 ± 0.3 | 12.6 ± 3.3 | 28.4 ± 3.8 | 13.3 ± 5.1 | 58.3 ± 6.8 | 11.4 ± 2.2 |
| 38 | 12.1 ± 1.6 | 27.7 ± 2.5 | 96.5 ± 8.6 | >100 | 91.2 ± 9.9 | >100 | >100 |
| 39 | 12.2 ± 2.3 | 35.1 ± 4.7 | 98.4 ± 9.1 | >100 | 99.1 ± 8.1 | >100 | >100 |
| 40 | 17.4 ± 0.9 | 41.8 ± 3.9 | 96.5 ± 6.4 | >100 | 98.1 ± 6.7 | >100 | 78.5 ± 5.8 |

Cells were treated with various concentrations ranging from 0.1 $\mu$M to 100 $\mu$M of oxovanadium(IV) complexes for 48 hr and the cell survival was measured with MTT assays and EC$_{50}$s were calculated with non-linear regression analysis.

TABLE 8

Cytotoxic Activity of Oxovanadium (IV) Compounds Against Testicular cancer, Brain tumor, Breast Cancer and Prostate Cancer cells

| Compound | 833-K | 64cp5 | TERA-2 | NTD1 | U373 | BT20 | PC3 |
|---|---|---|---|---|---|---|---|
| 26 | 12.8 | 8.5 | >100 | >100 | 7.7 | 6.6 | 11.2 |
| 27 | 7.5 | 18.5 | 37.6 | >100 | 6.8 | 7.2 | 10.8 |
| 28 | 6 | 15.2 | 57.6 | 12.8 | 2.2 | 2.1 | 5.8 |
| 29 | 0.85 | 0.75 | 19.5 | 10.8 | 1.8 | 1.5 | 1.7 |
| 30 | 12.8 | 10.9 | 18.1 | >100 | 22.4 | 18.2 | 12.4 |
| 31 | 4.6 | >100 | 24.2 | 50.1 | 6.3 | 5.4 | 4.6 |
| 32 | 11.5 | 25.4 | 7.2 | 20.2 | 20.5 | 13.7 | 12.9 |
| 33 | 1.1 | 5.9 | 2.6 | 9.1 | 7.2 | 5.6 | 6.1 |
| 34 | >100 | >100 | >100 | >100 | 58.4 | 51.2 | 55.8 |
| 35 | 96.2 | >100 | >100 | >100 | >100 | 70.8 | 56.2 |
| 36 | >100 | >100 | >100 | >100 | >100 | >100 | N.D. |
| 37 | 34.9 | >100 | >100 | >100 | 25.6 | 15.7 | N.D. |
| 38 | >100 | >100 | 74.3 | >100 | >100 | >100 | N.D. |
| 39 | >100 | >100 | >100 | >100 | >100 | >100 | N.D. |
| 40 | >100 | >100 | 35.4 | >100 | >100 | >100 | N.D. |

Synthetic Scheme 1:
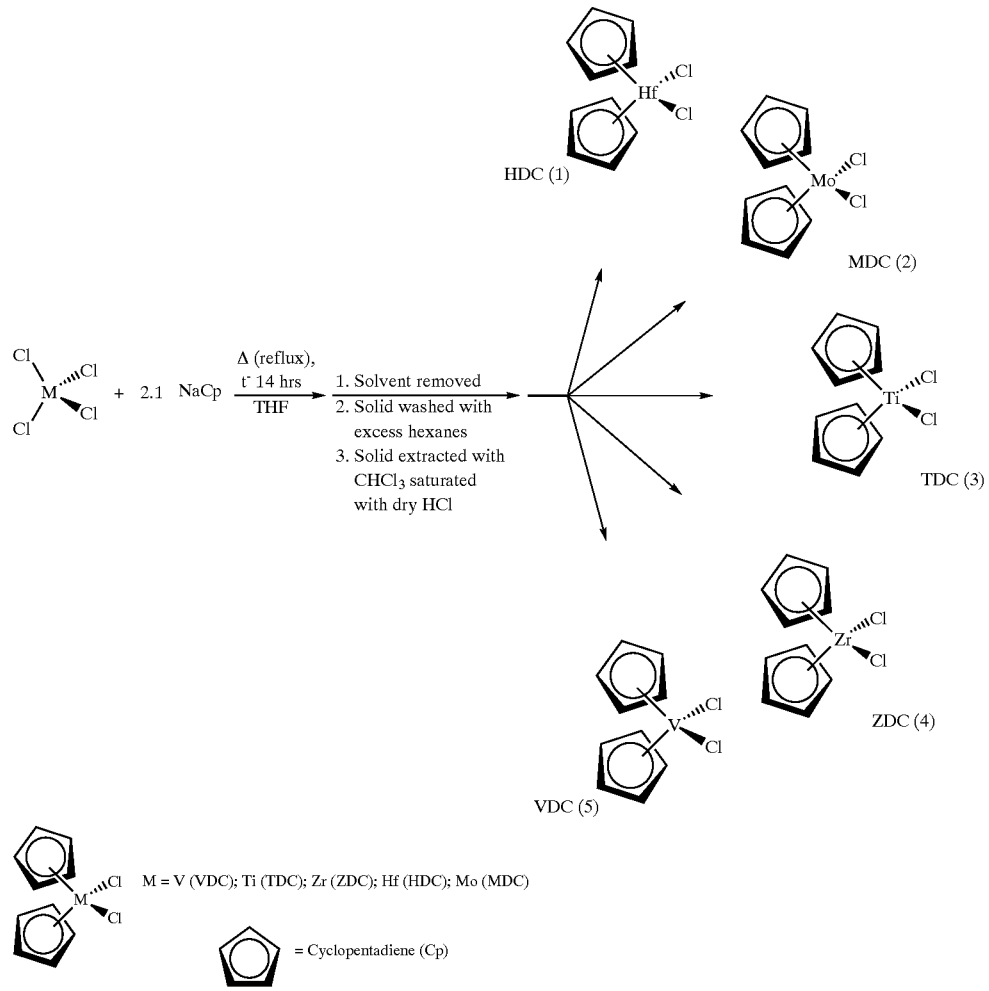
Synthetic Scheme 2:
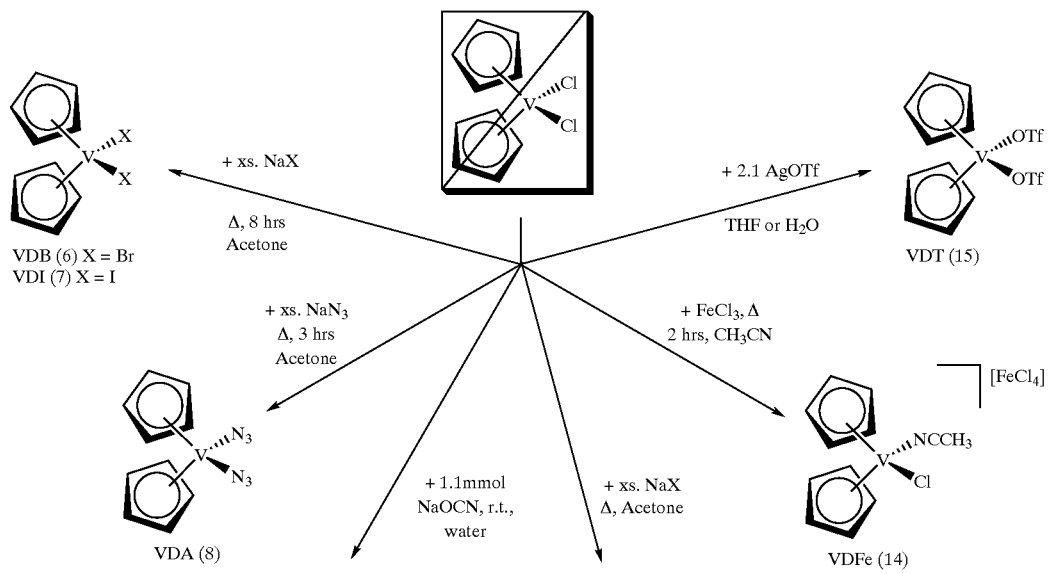

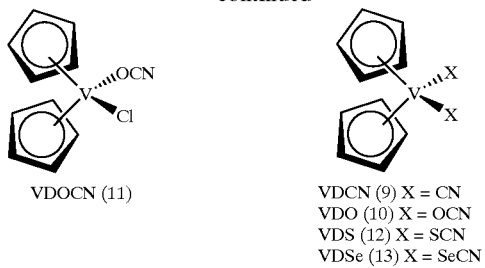
VDOCN (11)
VDCN (9) X = CN
VDO (10) X = OCN
VDS (12) X = SCN
VDSe (13) X = SeCN
Synthetic Scheme 3:
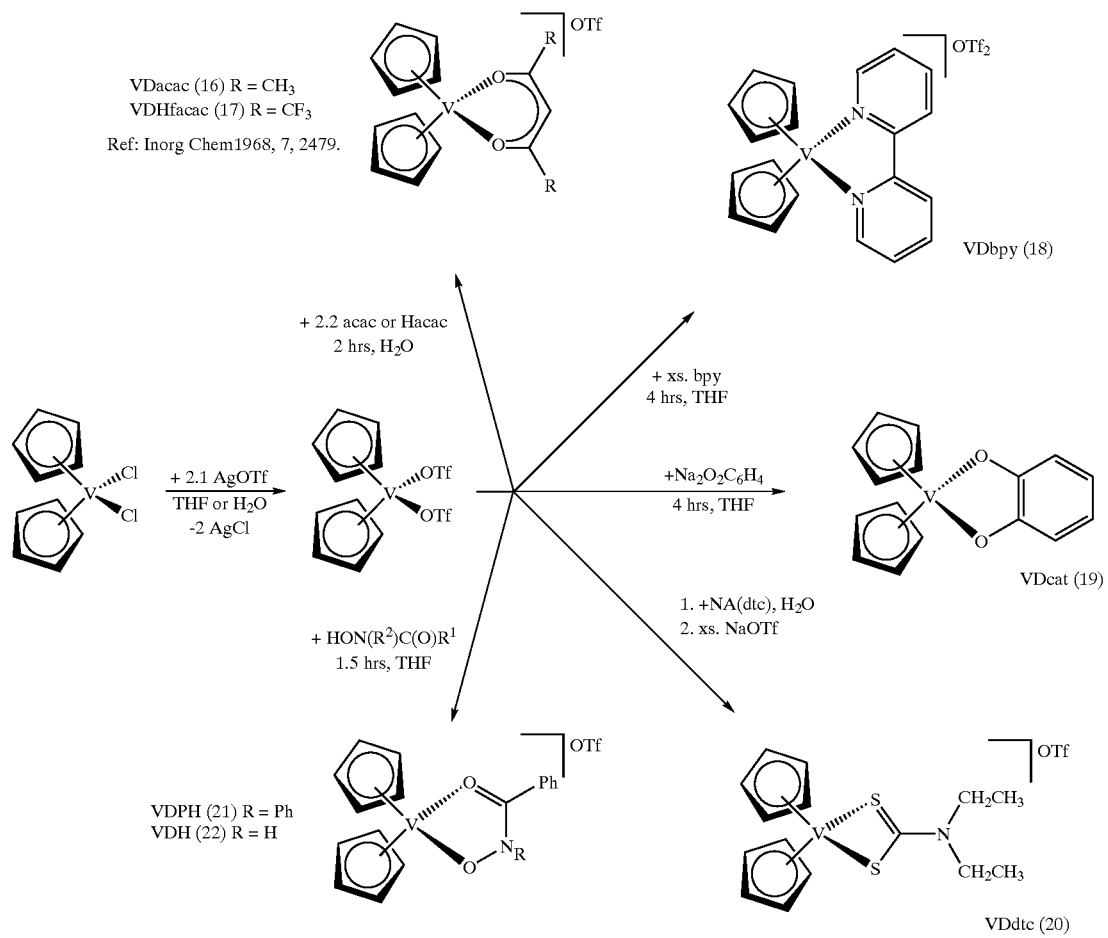
Synthetic Scheme 4:
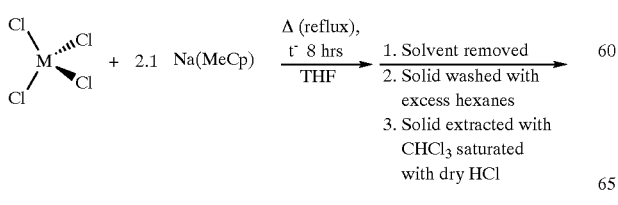
-continued
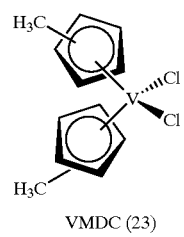
VMDC (23)

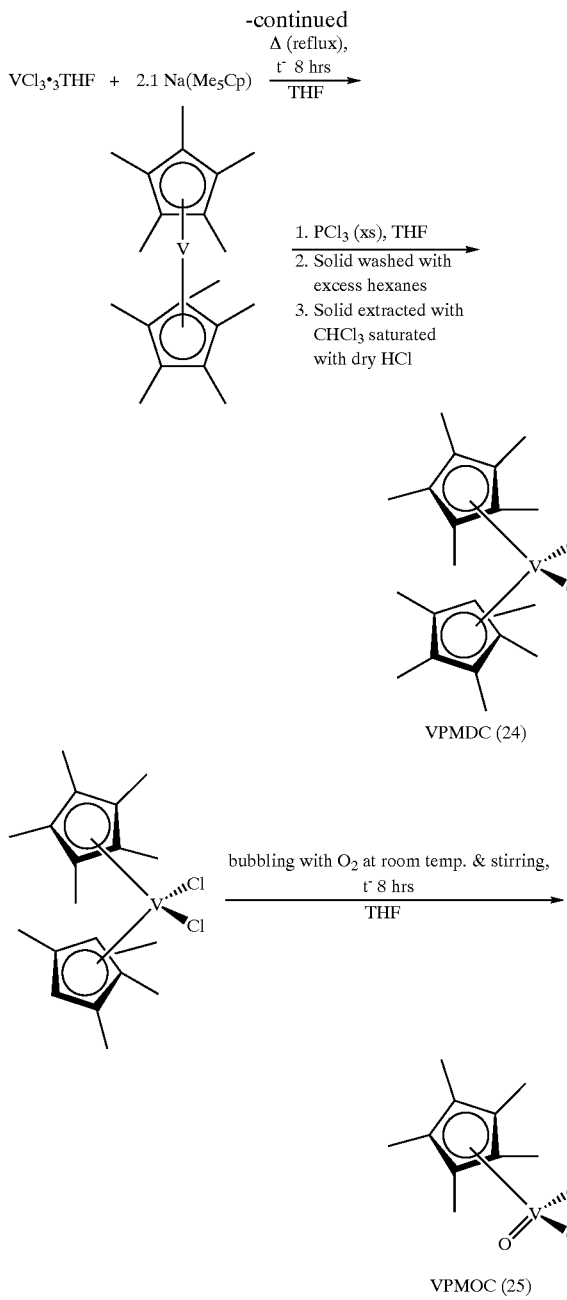

Example 3

The following illustrate representative pharmaceutical dosage forms, containing a compound of formula I ('Compound X'), for therapeutic or prophylactic use in humans.

| (I) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |
| (ii) Tablet 2 | mg/tablet |
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |
| (iii) Capsule | mg/capsule |
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |
| (iv) Injection 1 (1 mg/ml) | mg/ml |
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |
| (v) Injection 2 (10 mg/ml) | mg/ml |
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |
| (vi) Aerosol | mg/can |
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula II:
wherein

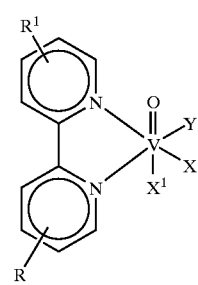

(II)

R and $R^1$ are each independently H (C1–C3)alkyl, halogen, (C1–C3)alkoxy, halo(C1–C3)alkyl, cyano, (C2–C6)alkanoyloxy or nitro;

X and $X^1$ are each $OH_2$; or taken together X and $X^1$ form a N,N-bidentate selected from the group consisting of N,N-bipyridine, N,N-bipyrimidine, and N,N-phenanthroline, wherein the N,N-bidentate can be substituted with up to two groups that are independently (C1–C3) alkyl, halogen, (C1–C3) alkoxy, halo (C1–C3) alkyl, cyano, (C2–C6) alkanoyloxy or nitro; and Y is $OSO_3$;

or a pharmaceutically acceptable salt thereof.

2. The compound of claim 1, wherein R and $R^1$ are methyl.

3. The compound of claim 1, wherein the compound is

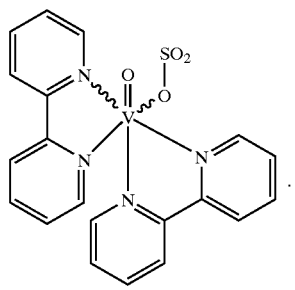

4. The compound of claim 1, wherein the compound is

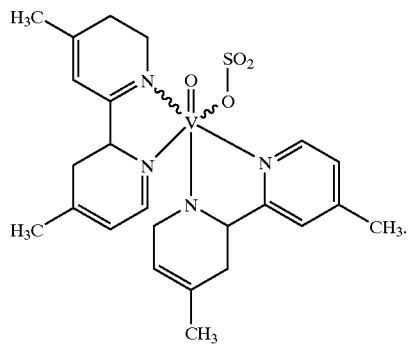

5. A compound of formula

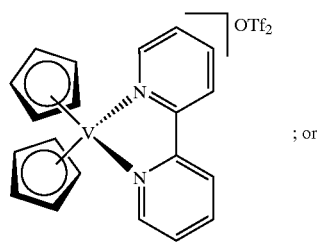

a pharmaceutically acceptable salt thereof.

6. A compound of formula

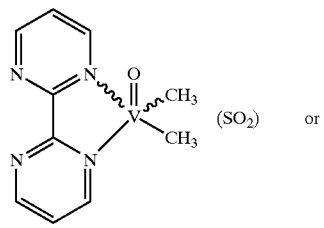

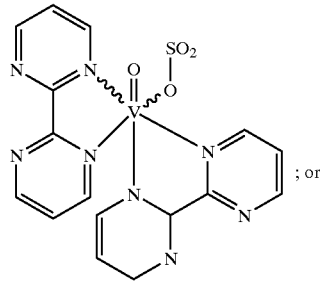

a pharmaceutically acceptable salt thereof.

7. A method for treating leukemia, Hodgkin's lymphoma, non-Hodgkin's lymphoma, multiple myeloma, testicular cancer, brain tumor, breast cancer, or prostate cancer, in a mammal comprising administering to said mammal an effective amount of

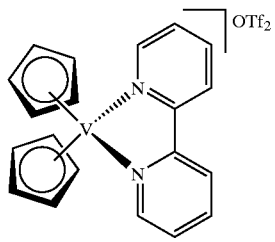

8. A method for treating leukemia, Hodgkin's lymphoma, non-Hodgkin's lymphoma, multiple myeloma, testicular cancer, brain tumor, breast cancer, or prostate cancer, in a mammal comprising administering to said mammal an effective amount of a compound of formula II:

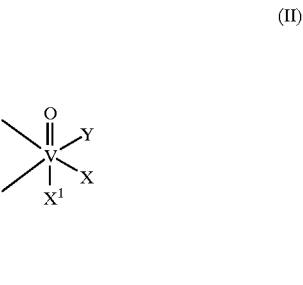

(II)

wherein

R and $R^1$ are each independently H, (C1–C3)alkyl, halogen, (C1–C3)alkoxy, halo(C1–C3)alkyl, cyano, (C2–C6)alkanoyloxy or nitro;

X and $X^1$ are each independently $OH_2$; X is $OH_2$ and no ligand is present on $X^1$; or taken together X and $X^1$ form a N,N-bidentate selected from the group consisting of N,N-bipyridine, N,N-bipyrimidine, and N,N-phenanthroline, wherein the N,N-bidentate can be substituted with up to two groups that are independently (C1–C3) alkyl, halogen (C1–C3) alkoxy, halo (C1–C3) alkyl, cyano, (C2–C6) alkanoyloxy or nitro; and Y is $OH_2$ or $OSO_3$; or a pharmaceutically acceptable salt thereof.

9. The method of claim 8, wherein the compound is

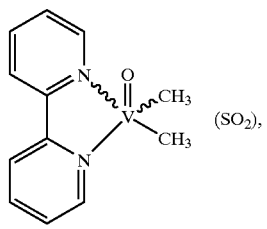 ($SO_2$),

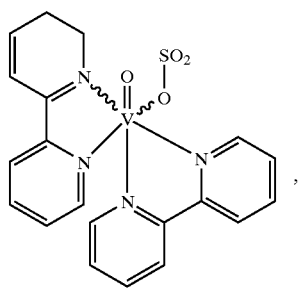,

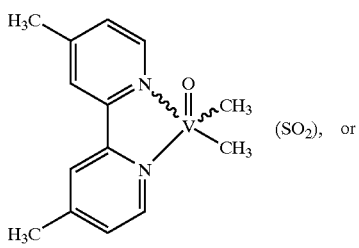 ($SO_2$), or

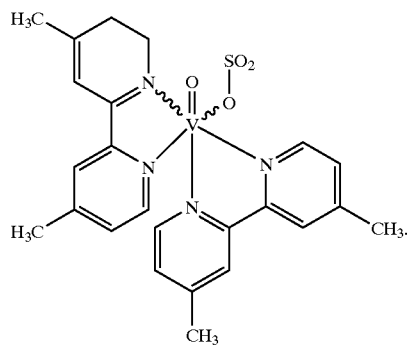

10. A method for treating leukemia, Hodgkin's lymphoma, non-Hodgkin's lymphoma, multiple myeloma, testicular cancer, brain tumor, breast cancer, or prostate cancer, in a mammal comprising administering to said mammal an effective amount of a compound of formula

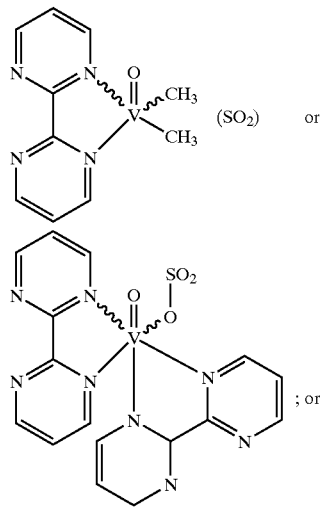

a pharmaceutically acceptable salt thereof.

11. A pharmaceutical composition comprising a compound of formula II:

(II)

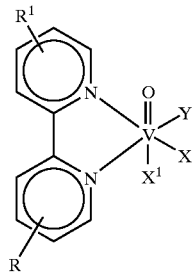

wherein

R and $R^1$ are each independently H, (C1–C3)alkyl, halogen, (C1–C3)alkoxy, halo(C1–C3)alkyl, cyano, (C2–C6)alkanoyloxy or nitro;

X and $X^1$ are each independently $OH_2$, X is $OH_2$ and no ligand is present on $X^1$; or taken together X and $X^1$ form a N,N-bidentate selected from the group consisting of N,N-bipyridine, N,N-bipyrimidine, and N,N-phenanthroline, wherein the N,N-bidentate can be substituted with up to two groups that are independently (C1–C3) alkyl, halogen, (C1–C3) alkoxy, halo (C1–C3) alkyl, cyano, (C2–C6) alkanoyloxy or nitro; and Y is $OH_2$ or $OSO_3$; or a pharmaceutically acceptable salt thereof; and a pharmaceutically acceptable carrier.

12. The pharmaceutical composition of claim 11, wherein the compound is

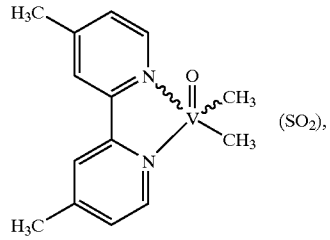 ($SO_2$),

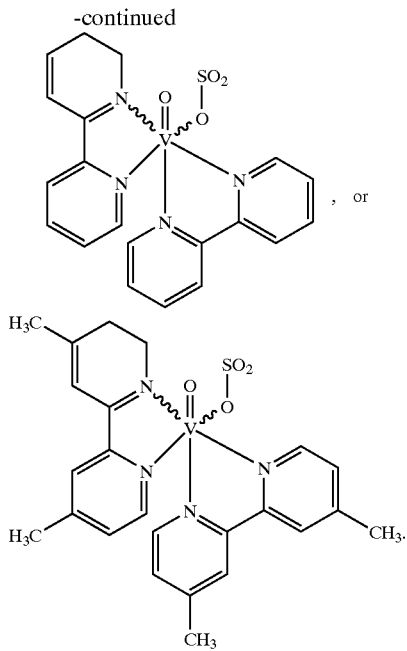, or

13. A pharmaceutical composition comprising a compound of formula

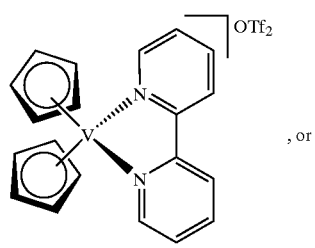, or a pharmaceutically acceptable salt thereof; and
a pharmaceutically acceptable carrier.

14. A pharmaceutical composition comprising a compound of formula

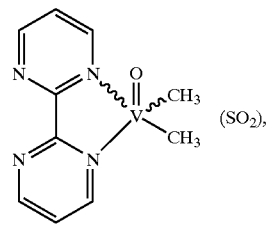 (SO₂),

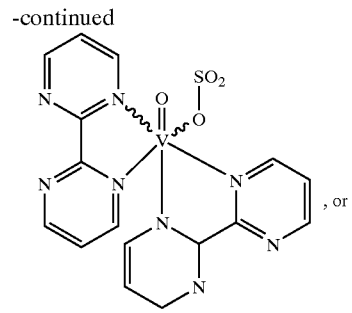, or a pharmaceutically acceptable salt thereof; and
a pharmaceutically acceptable carrier.

15. The compound of claim 1, wherein the N,N-bidentate ligand is substituted with at least one methyl.

16. A compound of formula II:
wherein

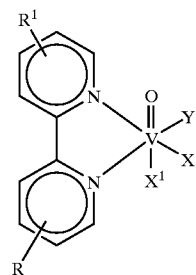

(II)

R and R¹ are each independently H, (C1–C3)alkyl, halogen, (C1–C3)alkoxy, halo(C1–C3)alkyl, cyano, (C2–C6)alkanoyloxy or nitro;
X is $OH_2$ and no ligand is present on $X^1$; and
Y is $OH_2$;
or a pharmaceutically acceptable salt thereof.

17. The compound of claim 16, wherein R and R¹ are methyl.

18. The compound of claim 16, wherein the compound is

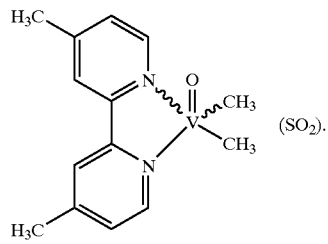 (SO₂).

* * * * *

UNITED STATES PATENT AND TRADEMARK OFFICE
CERTIFICATE OF CORRECTION

PATENT NO. : 6,743,786 B2
DATED : June 1, 2004
INVENTOR(S) : Uckun et al.

It is certified that error appears in the above-identified patent and that said Letters Patent is hereby corrected as shown below:

Title page,
Item [56], References Cited, OTHER PUBLICATIONS, insert line break before
-- Roschin, et al. 1980, *Gig. Tr. Prof. Zabol.*, 5:49-51 (Abstract only) "Effect of
*vanadium* on the generative function of laboratory animals". -- in appropriate order.

Column 30,
Lines 52-53, "Environ. Contain. Toxicol" should read -- Environ. Contam. Toxicol --

Column 51,
Lines 21-22, "calorimetric assays were used" should read -- colorimetric assays were used --

Column 63,
Lines 23-32, the compound should read
--
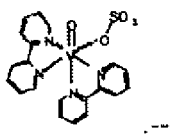
--

Lines 38-50, the compound should read
--
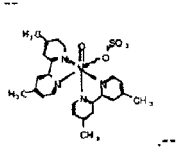
--

Lines 55-63, the compound should read
--
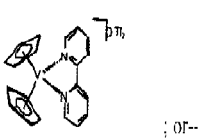
; or --

UNITED STATES PATENT AND TRADEMARK OFFICE
CERTIFICATE OF CORRECTION

PATENT NO. : 6,743,786 B2
DATED : June 1, 2004
INVENTOR(S) : Uckun et al.

It is certified that error appears in the above-identified patent and that said Letters Patent is hereby corrected as shown below:

Column 64,
Lines 2-22, the compound should read
--

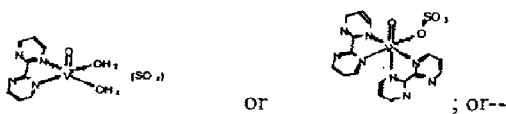

; or--

Column 65,
Lines 16-24, the compound should read
--

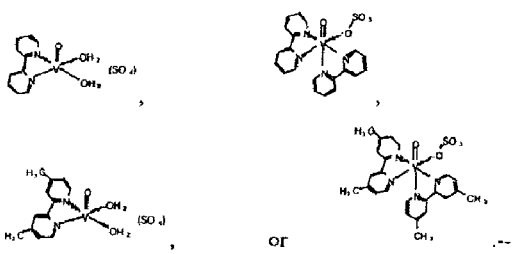

--

Column 66,
Lines 2-20, the compound should read
--

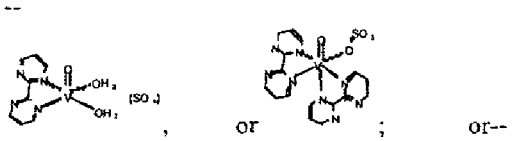

or--

Lines 57-66, the compound should read
--

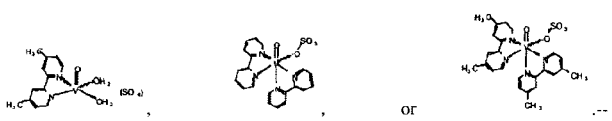

--

UNITED STATES PATENT AND TRADEMARK OFFICE
CERTIFICATE OF CORRECTION

PATENT NO.   : 6,743,786 B2  
DATED        : June 1, 2004  
INVENTOR(S)  : Uckun et al.

It is certified that error appears in the above-identified patent and that said Letters Patent is hereby corrected as shown below:

Column 67,  
Lines 46-55, the compound should read

--

, or--

Column 68,  
Lines 43-53, the compound should read

--

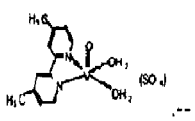  --

Signed and Sealed this

Twenty-third Day of November, 2004

JON W. DUDAS  
*Director of the United States Patent and Trademark Office*